(12) United States Patent
Etinger et al.

(10) Patent No.: US 7,692,023 B2
(45) Date of Patent: Apr. 6, 2010

(54) CANDESARTAN CILEXETIL POLYMORPHS

(75) Inventors: Marina Yu Etinger, Nesher (IL); Boris Fedotev, Haifa (IL); Tamas Koltai, Petah Tiqva (IL); Ziv Kurgan, Beer-Sheva (IL); Omer Malachi, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 662 days.

(21) Appl. No.: 11/056,895

(22) Filed: Feb. 11, 2005

(65) Prior Publication Data

US 2005/0250828 A1 Nov. 10, 2005

Related U.S. Application Data

(60) Provisional application No. 60/544,131, filed on Feb. 11, 2004, provisional application No. 60/572,672, filed on May 19, 2004, provisional application No. 60/607,180, filed on Sep. 3, 2004, provisional application No. 60/613,689, filed on Sep. 28, 2004.

(51) Int. Cl.
C07D 403/00 (2006.01)
(52) U.S. Cl. .................................................... 548/250
(58) Field of Classification Search ................ 548/250, 548/252
See application file for complete search history.

(56) References Cited

U.S. PATENT DOCUMENTS

| | | | |
|---|---|---|---|
| 4,151,273 A | 4/1979 | Riegelman et al. | |
| 4,196,188 A | 4/1980 | Besins | |
| 4,302,446 A | 11/1981 | Kaplan et al. | |
| 4,840,799 A | 6/1989 | Appelgren et al. | |
| 5,145,684 A | 9/1992 | Liversidge et al. | |
| 5,196,444 A | 3/1993 | Naka et al. | |
| 5,210,206 A | 5/1993 | Morton et al. | |
| 5,271,944 A | 12/1993 | Lee | |
| 5,281,604 A | 1/1994 | Levin et al. | |
| 5,298,517 A | 3/1994 | Levin | |
| 5,328,919 A | 7/1994 | Naka et al. | |
| 5,371,233 A | 12/1994 | Daumas et al. | |
| 5,385,925 A | 1/1995 | Narr et al. | |
| 5,401,764 A | 3/1995 | Naka et al. | |
| 5,534,534 A | 7/1996 | Makino et al. | |
| 5,578,733 A | 11/1996 | Shida et al. | |
| 5,587,393 A | 12/1996 | Narr et al. | |
| 5,684,029 A | 11/1997 | Narr et al. | |
| 5,703,110 A | 12/1997 | Naka et al. | |
| 5,705,517 A | 1/1998 | Naka et al. | |
| 5,721,263 A | 2/1998 | Inada et al. | |
| 5,763,619 A | 6/1998 | Shida et al. | |
| 5,958,961 A | 9/1999 | Inada et al. | |
| 5,962,491 A | 10/1999 | Naka et al. | |
| 6,004,989 A | 12/1999 | Naka et al. | |
| 6,177,587 B1 | 1/2001 | Hashimoto et al. | |
| 6,551,532 B1 | 4/2003 | Boissier et al. | |
| 7,098,342 B2 * | 8/2006 | Etinger et al. ............... 548/250 |
| 2002/0151723 A1 | 10/2002 | Naka et al. | |
| 2004/0215023 A1 | 10/2004 | Hashimoto et al. | |
| 2006/0165806 A1 | 7/2006 | Liversidge et al. | |

FOREIGN PATENT DOCUMENTS

| | | |
|---|---|---|
| CN | 1 361 101 | 7/2002 |
| DE | 4 212 748 | 10/1993 |
| EP | 0 425 921 A | 5/1991 |
| EP | 0 459 136 A | 12/1991 |
| EP | 0 545 912 | 6/1993 |
| EP | 0 668 272 | 8/1995 |
| EP | 0 881 212 A | 12/1998 |
| EP | 1 420 016 A | 5/2004 |
| JP | 5-271205 | 10/1993 |
| JP | 7-121918 | 5/1995 |
| JP | 8-183701 | 7/1996 |
| JP | 10-101615 | 4/1998 |
| JP | 3461863 | 10/2003 |
| JP | 2005-206603 | 8/2005 |
| JP | 2009-102438 | 5/2009 |
| WO | WO 93/04059 | 3/1993 |
| WO | WO 96/00610 | 1/1996 |
| WO | WO 97/14407 | 4/1997 |
| WO | WO 02/094816 | 11/2002 |
| WO | WO 03/014112 | 2/2003 |
| WO | WO 03/037876 | 3/2003 |
| WO | WO 03/048135 | 6/2003 |
| WO | WO 2004/085426 A | 10/2004 |
| WO | WO 2005/021535 | 3/2005 |

(Continued)

OTHER PUBLICATIONS

Black, et al., "Laser-Based Techniques for Particle-Size Measurement: A Review of Sizing Methods and Their Industrial Applications", Prog. Energy Combust. Sci., 1996, pp. 267-306, vol. 22.

Riddik, J.A. et al. "Organic Solvents, Physical Properties and Methods of Purification" pp. 868-871, Section 78: Methanol, 1986, John Wiley & Son, New York.

Hirokazu Matsunaga, et al. "Solid-state characterization of candesartan cilexetil (TCV-116): crystal structure and molecular mobility", Feb. 1999, Chemical and Pharmaceutical Bulletin, Pharmaceutical Society of Japan, Tokyo, JP, pp. 182-186.

Kubo, K. et al., "Nonpeptide Angiotensin II Receptor Antagonists, Synthesis and Biological Activity of Potential Prodrugs of Benzimidazole-7-carboxylic Acids", J Med Chem, 1993, 36: 2343-2349.

(Continued)

Primary Examiner—Golam M. M. Shameem
Assistant Examiner—Susannah Chung
(74) Attorney, Agent, or Firm—Kenyon & Kenyon LLP

(57) ABSTRACT

Provided are candesartan cilexetil forms and methods of their preparation. Also provided are pharmaceutical compositions prepared by combining at least one pharmaceutically-acceptable execipient with at least one candesartan cilexetil form of the invention.

5 Claims, 28 Drawing Sheets

FOREIGN PATENT DOCUMENTS

| | | |
|---|---|---|
| WO | WO 2005/037821 A2 | 4/2005 |
| WO | WO 2005/051928 A1 | 6/2005 |
| WO | WO 2005/077941 A2 | 8/2005 |
| WO | WO 2005/111021 A1 | 11/2005 |
| WO | WO 2005/123720 | 12/2005 |
| WO | WO 2005/123721 | 12/2005 |
| WO | WO 2006/048237 | 5/2006 |
| WO | WO 2008/012371 | 1/2008 |
| WO | WO 2008/035360 | 3/2008 |

OTHER PUBLICATIONS

Office Action from related U.S. Appl. No. 10/966,418, mailed Sep. 23, 2008.

Office Action from related U.S. Appl. No. 10/432,108, mailed Sep. 10, 2008.

Third Party Observation received for Third Party Observation filed for European Application No. 05713277.1-1521, dated Mar. 13, 2009.

Organikum, Veb-Verlag Berlin 1965, p. 35-38.

The Chemistry Society of Japan, Handbook of Chemistry, Applied 6$^{th}$ ed, Maruzen Co. Ltd. published Jan. 30, 2003, Chapter 4: Chemical Synthesis Technology, p. 178.

Harmat et al. "4-Diazinyl-and 4-Pyridinylimidazoles: Potent Angiotensin II Antagonists. A Study of Their Activity and Computational Characterization," Journal of Med. Chemistry, 38: 2925-2937 (1995).

Lu et al., "Detritylation with Ytterbium Triflate", Tetrahedron letters, 41, 2817-2819 (2000).

Wahlstrom et al. "Detritylation of Ethers Using Iodine-Alcohol Reagents: An Acid-Catalyzed Reaction", *J. Org. Chem.*, 63(17): 6021-6022 (1998).

Greene et al, "Protective Groups in Organic Synthesis" 3 ed., John Wiley and Sons Inc., 1999, 103-104.

Greene et al, "Protective Groups in Organic Synthesis" John Wiley and Sons Inc., Oct. 2, 1998, p. 391.

Cao et al, "Synthesis of Candesartan Cilexetil", Chinese Journal of Pharmaceuticals: 34(9) 425-428 (2003).

Submission of Takeda dated Jul. 9, 1999.

Falbe et al, "Basen", Römpp, Chemie Lexikon, 9th Edition: 350-351.

Falbe et al, "Phasen-Transfer-Katalyse", Römpp, Chemie Lexikon, 9th Edition: 3342-3343.

"Phase transfer catalyst", www.en.wikipedia.org.

Kocienski, "Protecting Groups" (1994): 55-56, Georg Thieme Verlag: New York.

The Chemical Society of Japan, ed., Jikken-Kakaku-Koza 27, Bioorganic, Maruzen Co., Ltd., published on May 5, 1991, pp. 251-252.

Buckus, "Detritylation and Transtritylation Reactions," Russian Chemical Review, 39(1): 58-69 (1970).

Ogata, Kagaku-Jikken Sosa-Ho, vol. 1, Nankodo Co., Ltd., Nov. 20, 1963, 27$^{th}$ edition, pp. 366-399.

Ghislandi et al., Chirality, vol. II, 1999, pp. 21-28.

Asakura et al.,"Removal of Acetyl, Silyl, and 4, 4'-Dimethoxytrityl Protecting Groups from Hydroxyl Functions of Carbohydrates and Nucleosides with Clay in Aqueous Methanol," *J. Org. Chem.* 61(25): 9026-9027 (1996).

Kim et al., "Preparation of N($\pi$)-alkyl-histamine and histidine derivatives through efficient alkylation followed by deprotection using activated silica gel," Tetrahedron Letters, 41(51): 10031-10034 (2000).

Rote Liste GmbH®, Rote Liste 2004®, entries 17154 (Atacand® Tabletten) and 17155 (Blopress® tabletten).

Da Silva, Livrarie Lopes, "Analise Quantitativa", 3rd ed. 1983, pp. 97-98.

Lieberman et al., Pharmaceutical Dosage Forms, pp. 80-81, vol. 2, Marcel Dekker, Inc., New York, 1989.

Byrn et al., Solid-State Chemistry of Drugs, 2nd ed., pp. 82-85.

Rawle et al., Basic Principles of Particle Size Analysis, Technical Paper. <http://www.nbtc.cornell.edu/facilities/downloads/Basic%20principles%20of%20particle%20size%20analysis.pdf>.

Technical information re. Malvern Mastersizer S. <http://www.malvern.com/LabEng/products/Mastersizer/mss/mastersizer_s.htm>.

Allen, Particle Size Measurement, vol. 1, 5th ed., Chapman & Hall, London, 1997, pp. 404-415.

Havlicek et al., "Identification, Synthesis and Structural Determination of Some Impurities of Candesartan Cilexetil," *Collect. Czech. Chem. Commun.*, 74(2): 347-362 (2009).

Offer of Information received in Japanese Application No. 2005-013916, received Oct. 27, 2009.

* cited by examiner

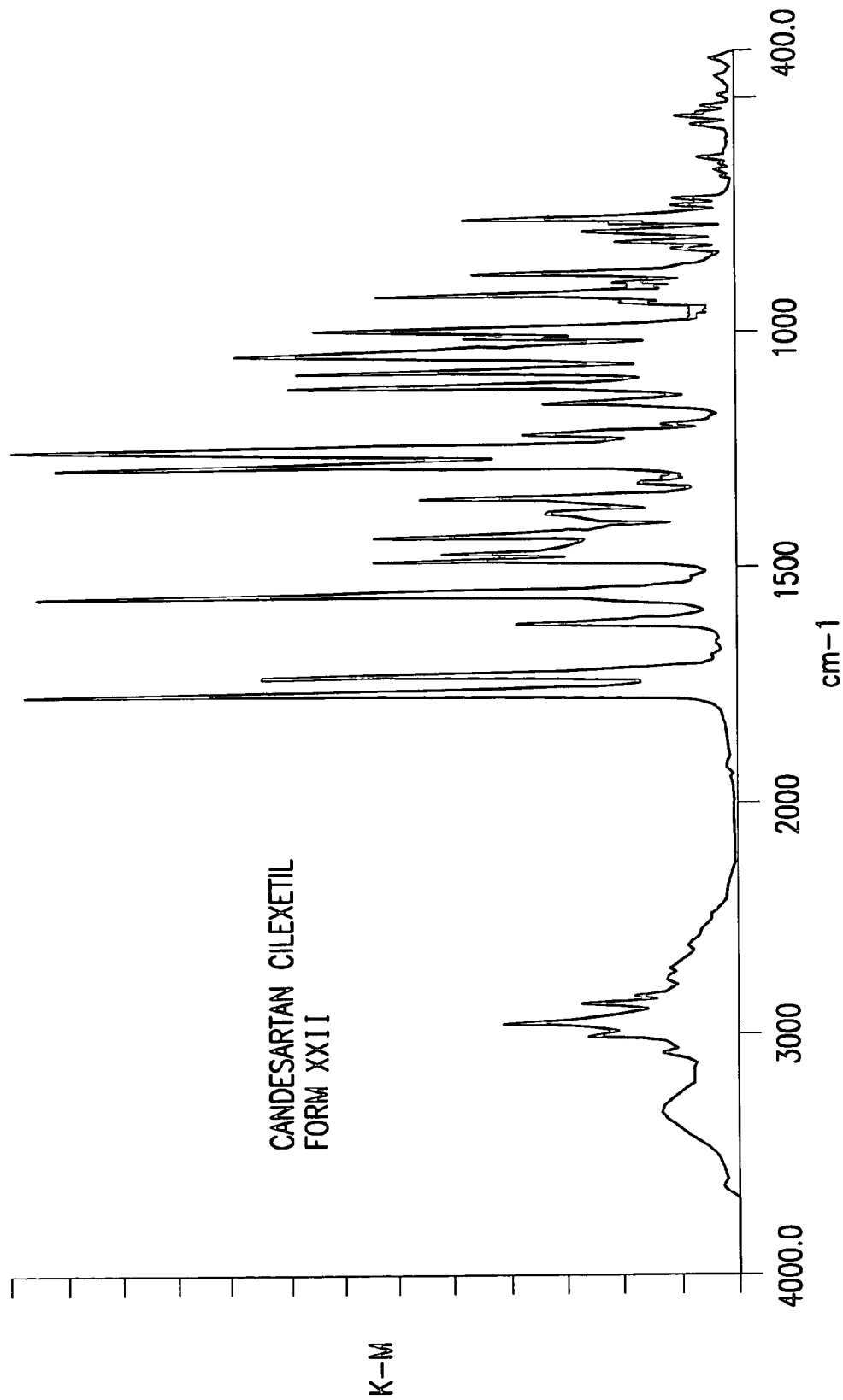

CANDESARTAN CILEXETIL POLYMORPHS

RELATED APPLICATIONS

This application claims the benefit of U.S. provisional application Nos. 60/544,131, filed Feb. 11, 2004; 60/572,672, filed May 19, 2004; 60/607,180, filed Sep. 3, 2004; and 60/613,689, filed Sep. 28, 2004; the contents of all of which are hereby incorporated herein by reference.

FIELD OF INVENTION

The present invention is directed to polymorphs of candesartan cilexetil and processes for their preparation. The invention is also directed to pharmaceutical compositions prepared by combining at least one pharmaceutically-acceptable excipient with at least one candesartan cilexetil form of the invention.

BACKGROUND OF THE INVENTION

Candesartan is a potent, long-acting, selective $AT_1$ subtype angiotensin II receptor antagonist. Candesartan is a useful therapeutic agent for treating circulatory system diseases such as hypertensive diseases, heart diseases (e.g. hypercardia, heart failure, cardiac infarction, etc.), strokes, cerebral apoplexy, and nephritis, among others. Candesartan meets the requirement of high potency but it is poorly absorbed when administered orally. Therefore, the prodrug candesartan cilexetil was developed. During absorption from the gastrointestinal tract candesartan cilexetil is rapidly and completely hydrolyzed to candesartan. The chemical name for candesartan is: 2-ethoxy-1-[[2'-(1H-tetrazol-5-yl)biphenyl-4-yl]methyl]-1H-benzimidazole-7-carboxylic acid. The chemical name for candesartan cilexetil is (±)-1-[[(cyclohexyloxy)carbonyl]oxy]ethyl-2-ethoxy-1-[[2'-(1H-tetrazol-5-yl)[1,1'biphenyl]-4-yl]methyl]-1H-benzimidazole-7-carboxylate. Candesartan cilexetil is a white to off-white powder and is sparingly soluble in water and in methanol. Although candesartan cilexetil contains an asymmetric center in the ester portion of the molecule, it is sold as the racemic mixture.

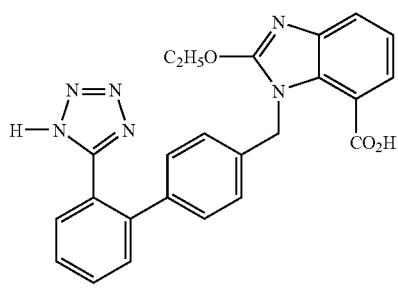

Candesartan $C_{24}H_{20}N_6O_3$
440.46
440.159688
C 65.45% H 4.58% N 19.08% O 10.90%

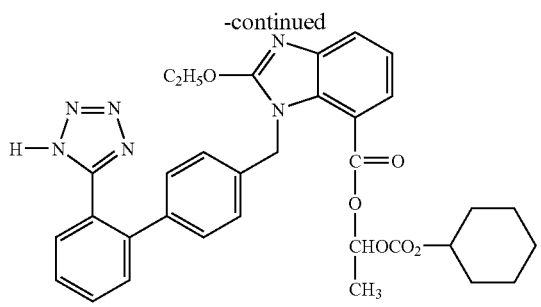

Candesartan Cilexetil $C_{33}H_{34}N_6O_6$
610.66
610.253983
C 64.91% H 5.61% N 13.76% O 15.72%

Angiotensin II is formed from angiotensin I in a reaction catalyzed by angiotensin-converting enzyme (ACE, kininase II). Angiotensin II is the principal pressor agent of the renin-angiotensin system, with effects that include vasoconstriction, stimulation of synthesis and release of aldosterone, cardiac stimulation, and renal reabsorption of sodium. Angiotensin II help maintain constant blood pressure despite fluctuations in a person's state of hydration, sodium intake and other physiological variables. Angiotensin II also performs the regulatory tasks of inhibiting excretion of sodium by the kidneys, inhibiting norephedrin reuptake and stimulating aldosterone biosynthesis. Candesartan blocks the vasoconstrictor and aldosterone secreting effects of angiotensin II by selectively blocking the binding of angiotensin II to the $AT_1$ receptor in many tissues, such as vascular smooth muscle and the adrenal gland. By inhibiting angiotensin II binding to $AT_1$ receptors, candesartan disrupts the vasoconstriction mediated by $AT_1$ receptors. Blocking vasoconstriction by angiotensin II has been found to be beneficial to patients with hypertension. The United States Food and Drug Administration has approved candesartan for the treatment of hypertension alone or in combination with other antihypertensive agents.

U.S. Pat. No. 5,196,444 relates to one crystal form of candesartan cilexetil, the C-type crystal (Form I). The patent also relates to methods for producing Form I under acidic conditions that permit esterification.

The therapeutic effectiveness of candesartan cilexetil has created a need for more efficient synthetic routes to the product, as well as purification methods that provide candesartan cilexetil forms in high yields and purity without further loss of compound or excessive purification steps that may add cost or time to the purification process. Therefore, to address this need, the present invention provides novel candesartan cilexetil polymorphs and processes for preparing candesartan cilexetil.

SUMMARY OF THE INVENTION

The invention encompasses crystalline candesartan cilexetil solvate.

The candesartan cilexetil may be a solvate of acetone, tetrahydrofuran, dichloromethane/heptane, toluene, methyl ethyl ketone, dioxane/water, chloroform/heptane, dichloromethane/isoamyl acetate, dichloromethane, tetrahydrofuran/water, acetonitrile/water, chloroform/acetonitrile, methanol or toluene/methanol.

One embodiment of the invention is directed towards a process for preparing candesartan cilexetil Form I, the process comprising dissolving candesartan cilexetil in a solvent to form a solution; heating the solution at a temperature of at least about 45° C.; and precipitating candesartan cilexetil Form I, wherein the solvent is at least one of a $C_1$-$C_4$ alcohol, a $C_3$-$C_8$ ester, or acetonitrile.

The preferred solvent is at least one of butanol, methanol, isopropanol, ethanol, ethyl acetate or acetonitrile. Preferably, the solution of step (b) is heated at a temperature of from about 45° C. to about 70° C., and more preferably at reflux. The process may further comprise drying the candesartan cilexetil at a temperature of from about 35° C. to about 60° C.

Another process for preparing candesartan cilexetil Form I comprises dissolving candesartan cilexetil in a solvent to form a solution; combining water with the solution to form a mixture; and precipitating from the mixture candesartan cilexetil Form I, wherein the solvent is at least one of a $C_1$-$C_4$ alcohol, a ketone, an alkyl amide, or acetonitrile.

The preferred solvent is at least one of methanol, isopropanol, ethanol, butanol, acetone, dimethylformamide, or acetonitrile. Preferably, the water is added dropwise to the solution. The process may further comprise heating the solution at a temperature of at least about 45° C. before water is combined.

Another process for preparing candesartan cilexetil Form I comprises heating candesartan cilexetil Form VII or Form VIII at a temperature of about 90° C. to about 120° C. for at least about 10 hours.

Another process for preparing candesartan cilexetil Form I comprises dissolving at least one of candesartan cilexetil Form XIV, XIV-1, XXII, or XXIII in a $C_1$-$C_4$ alcohol to form a solution and precipitating from the solution candesartan cilexetil Form I.

The preferred alcohol is ethanol. Preferably, the solution is cooled at a temperature of from about 0° C. to about 10° C. to precipitate candesartan cilexetil Form I.

Another process for preparing candesartan cilexetil Form I comprises preparing a slurry of candesartan cilexetil Form XIV, XIV-I, XXII, or XXIII in a $C_1$-$C_4$ alcohol; and isolating from the slurry candesartan cilexetil Form I. The slurry is preferably cooled at a temperature of from about −20° C. to about 20° C.

One embodiment of the invention encompasses a candesartan cilexetil crystalline form characterized by X-ray powder diffraction peaks at about 6.1, 7.3, 14.2, 17.5, and 22.4 degrees two-theta, ±0.2 degrees two-theta (Form XIV). Form XIV may be identified further by X-ray powder diffraction peaks at about 8.1, 10.4, 15.3, 20.5, and 25.3 degrees two-theta, ±0.2 degrees two-theta. Form XIV may be a solvate of dichloromethane; with a L.O.D. by TGA of about 16% by weight.

Another embodiment of the invention encompasses candesartan cilexetil Form XIV prepared by a process comprising dissolving candesartan cilexetil in dichloromethane to form a solution; combining toluene with the solution to form a mixture; and precipitating from the mixture candesartan cilexetil Form XIV.

One embodiment of the invention encompasses a candesartan cilexetil crystalline form characterized by at least one of an X-ray powder diffraction with peaks at about 7.3, 8.2, 14.3, 20.5, and 23.8 degrees two-theta, ±0.2 degrees two-theta, or an FTIR spectrum with characteristic absorption bands at about 1733, 1479, 1359, 1288, 1253, and 1085 cm$^{-1}$ (Form XIV-1). Form XIV-1 may be identified further by X-ray powder diffraction peaks at about 6.4, 9.3, 16.7, 25.3, and 28.0 degrees two-theta, ±0.2 degrees two-theta.

Another embodiment of the invention encompasses candesartan cilexetil Form XIV-1 prepared by a process comprising preparing a solution of trityl candesartan cilexetil in a first portion of toluene or dichloromethane, and a first $C_1$-$C_4$ alcohol, acid, or both to deprotect the trityl candesartan cilexetil and obtain candesartan cilexetil; concentrating the solution into a residue; combining a second portion of toluene or dichloromethane, and a second $C_1$-$C_4$ alcohol with the residue to form a mixture; and precipitating from the mixture candesartan cilexetil Form XIV-1.

Preferably, the first or second $C_1$-$C_4$ alcohol is methanol. The preferred acid is formic acid. The process may further comprise combining water with the solution of trityl candesartan cilexetil.

One embodiment of the invention encompasses a candesartan cilexetil crystalline form characterized by at least one of an X-ray powder diffraction pattern with peaks at about 10.6, 12.1, 17.8, 19.4 and 21.7 degrees two-theta, ±0.2 degrees two-theta, or an FTIR spectrum with characteristic absorption bands at about 1759, 1723, 1429, 1351, 1279, and 1082 cm$^{-1}$ (Form XXII). Form XXII may be identified further by X-ray powder diffraction peaks at about 7.1, 8.9, 16.3, 20.5 and 24.0 degrees two-theta, ±0.2 degrees two-theta. Form XXII may be a solvate of methanol; with a L.O.D. by TGA of about 4% to about 20% by weight.

Another embodiment of the invention encompasses candesartan cilexetil Form XXII prepared by a process comprising dissolving crude candesartan in a $C_1$-$C_4$ alcohol to form a solution; heating the solution at a temperature of at least about 45° C.; and precipitating from the solution candesartan cilexetil Form XXII. The preferred alcohol is methanol.

One embodiment of the invention encompasses a candesartan cilexetil crystalline form characterized by at least one of an X-ray powder diffraction pattern with peaks at about 6.0, 12.0, 18.0, 21.0, and 22.4 degrees two-theta, ±0.2 degrees two-theta, or an FTIR spectrum with characteristic absorption bands at about 1759, 1727, 1464, 1438 and 1071 cm$^{-1}$ (Form XXIII). Form XXIII may be identified further by X-ray powder diffraction peaks at about 10.3, 16.3, 19.8, 21.6, and 23.1 degrees two-theta, ±0.2 degrees two-theta. Form XXIII may be a toluene/methanol solvate; with a L.O.D. by TGA of about 5% to about 45% by weight.

Another embodiment of the invention encompasses candesartan cilexetil Form XXIII prepared by a process comprising preparing a solution of trityl candesartan cilexetil in a first portion of toluene or dichloromethane, a first $C_1$-$C_4$ alcohol, and water to deprotect the trityl candesartan cilexetil and obtain candesartan cilexetil; concentrating the solution into a residue; combining second portion of toluene or dichloromethane, and a second $C_1$-$C_4$ alcohol a with the residue to form a mixture; and precipitating from the mixture candesartan cilexetil Form XXIII.

Preferably, the first or second $C_1$-$C_4$ alcohol is methanol. The mixture may be seeded with candesartan cilexetil Form XXII to precipitate candesartan cilexetil Form XXIII.

The invention also encompasses candesartan cilexetil characterized by an X-ray powder diffraction pattern having peaks at about 6.5, 18.8, 20.3, 21.9, and 23.6±0.2 degrees two-theta; 6.1, 10.8, 18.4, 20.0, and 21.6±0.2 degrees two-theta; 6.2, 6.5, 7.3, 12.0, and 18.3±0.2 degrees two-theta; 6.5, 7.3, 9.3, 17.6, and 19.8±0.2 degrees two-theta; 7.4, 10.1, 17.5, 20.5, and 23.4±0.2 degrees two-theta; 6.4, 10.2, 17.5, 20.5, and 23.5±0.2 degrees two-theta; 6.5, 7.4, 8.4, 15.9, and 25.3±0.2 degrees two-theta; 6.0, 12.1, 18.1, 19.7, and 21.3±0.2 degrees two-theta; 6.5, 8.5, 18.0, 21.1, and 24.9±0.2 degrees two-theta; 6.2, 11.8, 16.5, 20.1, and 25.7±0.2 degrees two-theta; 6.3, 7.3, 20.0, 21.4, and 24.3±0.2 degrees two-theta; 7.0, 8.9, 16.7, 17.4, and 19.4±0.2 degrees two-theta; 3.6±0.2 degrees two-theta; 6.2, 10.8, 20.1, 20.7, and 21.6±0.2 degrees two-theta; 6.4, 7.3, 8.2, 14.7, and 15.7±0.2 degrees two-theta; 6.3, 12.5, 18.7, 20.3, and 23.3±0.2 degrees two-theta; and 6.1, 7.3, 20.0, 21.6, and 24.3±0.2 degrees two-theta.

The invention further encompasses candesartan cilexetil Form III, IV, V, VI, VII, VIII, IX, X, XI, XIII, XIV, XIV-1, XV, XVI, XVII, XVIII, XIX, XX, XXI, XXII, or XXIII, having less than about 5% by weight of other polymorphic forms.

In one embodiment, the candesartan cilexetil forms of the invention have an average particle size of up to about 500 microns, preferably up to about 200 microns, and more preferably up to about 50 microns.

In another embodiment, the invention encompasses a pharmaceutical composition prepared by combining at least one pharmaceutically-acceptable excipient with at least one candesartan cilexetil form of the invention.

BRIEF DESCRIPTION OF THE FIGURES

FIG. 23 illustrates the FTIR spectrum for candesartan cilexetil Form XXII.

DETAILED DESCRIPTION OF THE INVENTION

The invention encompasses candesartan cilexetil solvate.

The candesartan cilexetil may be a solvate of acetone, tetrahydrofuran, dichloromethane/heptane, toluene, methyl ethyl ketone, dioxane/water, chloroform/heptane, dichloromethane/isoamyl acetate, dichloromethane, tetrahydrofuran/water, acetonitrile/water, chloroform/acetonitrile, methanol or toluene/methanol.

The invention encompasses candesartan cilexetil forms and processes for preparing them. The invention also encompasses a pharmaceutical composition comprising the candesartan cilexetil forms of the invention, which may be in the form of particles, and methods of treating circulatory system diseases using the pharmaceutical composition. In addition, the invention encompasses a method of preparing a pharmaceutical composition comprising combining at least one of the candesartan cilexetil forms of the invention with at least one pharmaceutically-acceptable excipient.

Figure 1:
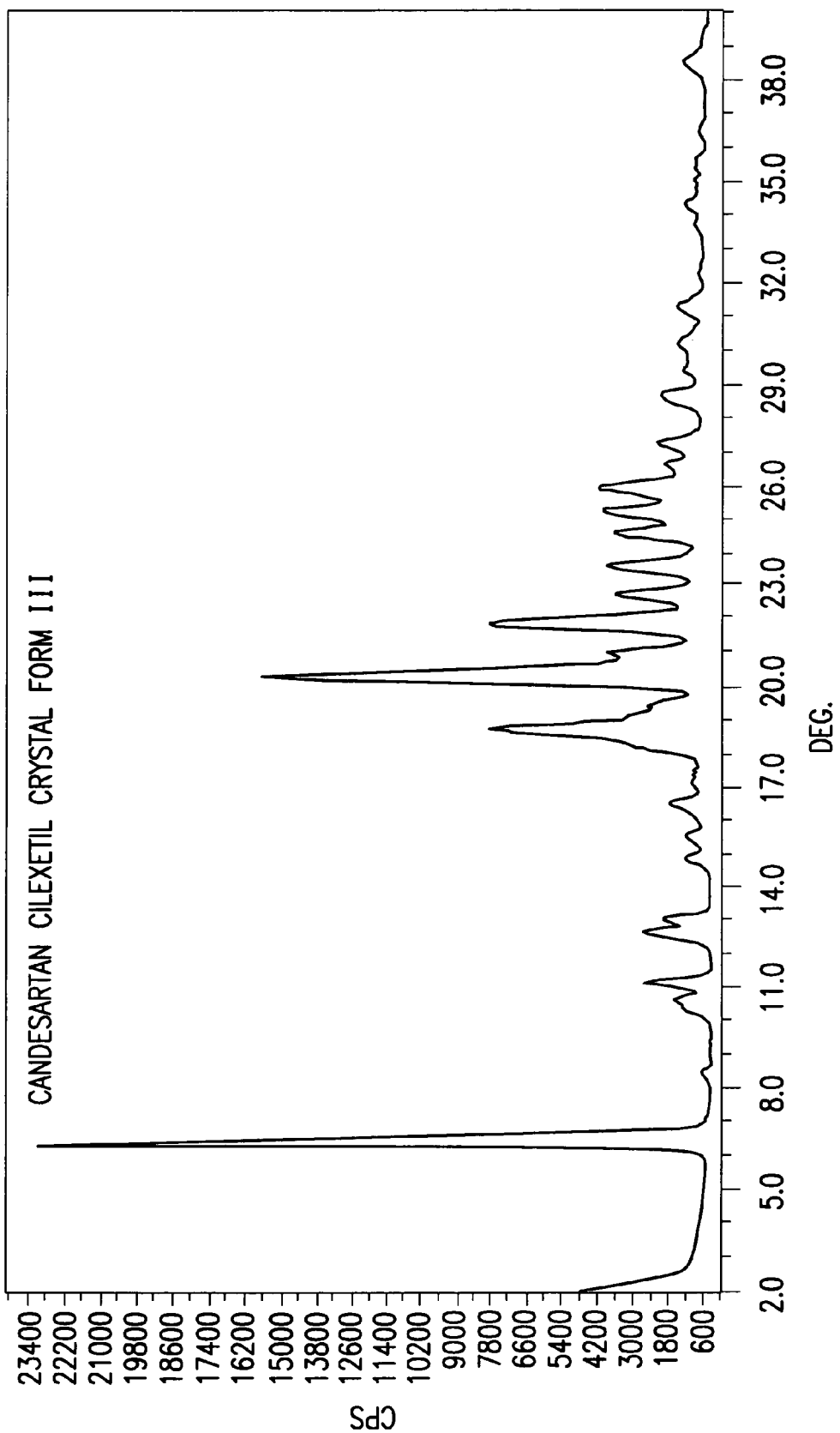
FIG. 1 illustrates the powder X-ray diffraction pattern for candesartan cilexetil Form III.

One embodiment of the invention encompasses a candesartan cilexetil form, herein defined as Form III, which has about 0.1% water by weight, and the weight loss as measured by TGA is about 6 to about 8% by weight. Form III may be a solvate of acetone with a Loss on Drying (L.O.D.) by TGA of about 8.6% by weight. Form III may also be a solvate of tetrahydrofuran; with a L.O.D. by TGA of about 6% by weight. Form III may be identified by an X-ray powder diffraction pattern with peaks at about 6.5, 18.8, 20.3, 21.9, and 23.6 degrees two-theta, ±0.2 degrees two-theta. Form III may be identified further by X-ray powder diffraction peaks at about 12.6, 22.7, 24.6, 25.3, and 25.9 degrees two-theta, ±0.2 degrees two-theta. See FIG. 1.

Figure 2:
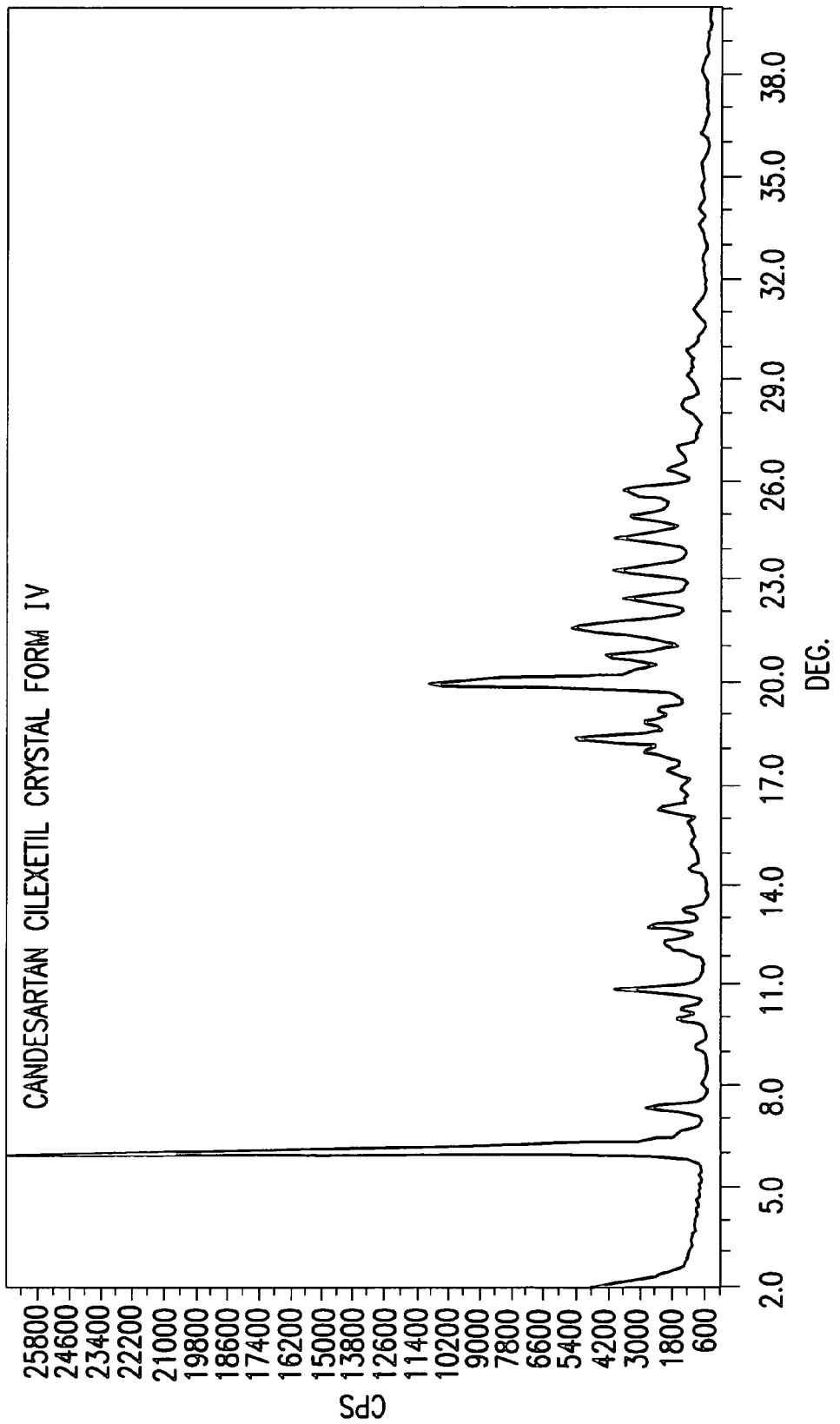
FIG. 2 illustrates the powder X-ray diffraction pattern for candesartan cilexetil Form IV.

Another embodiment of the invention encompasses another candesartan cilexetil form, herein defined as Form IV, which has about 0.2% to 0.3% water by weight and the weight loss measured by TGA is about 6% by weight. Form IV may be a solvate of tetrahydrofuran; with a L.O.D. by TGA of about 7% by weight. Form IV may be identified by an X-ray powder diffraction pattern with peaks at about 6.1, 10.8, 18.4, 20.0, and 21.6 degrees two-theta, ±0.2 degrees two-theta. Form IV may be identified further by X-ray powder diffraction peaks at about 7.3, 12.7, 22.5, 23.4, and 25.8 degrees two-theta, ±0.2 degrees two-theta. See FIG. 2.

Figure 3:
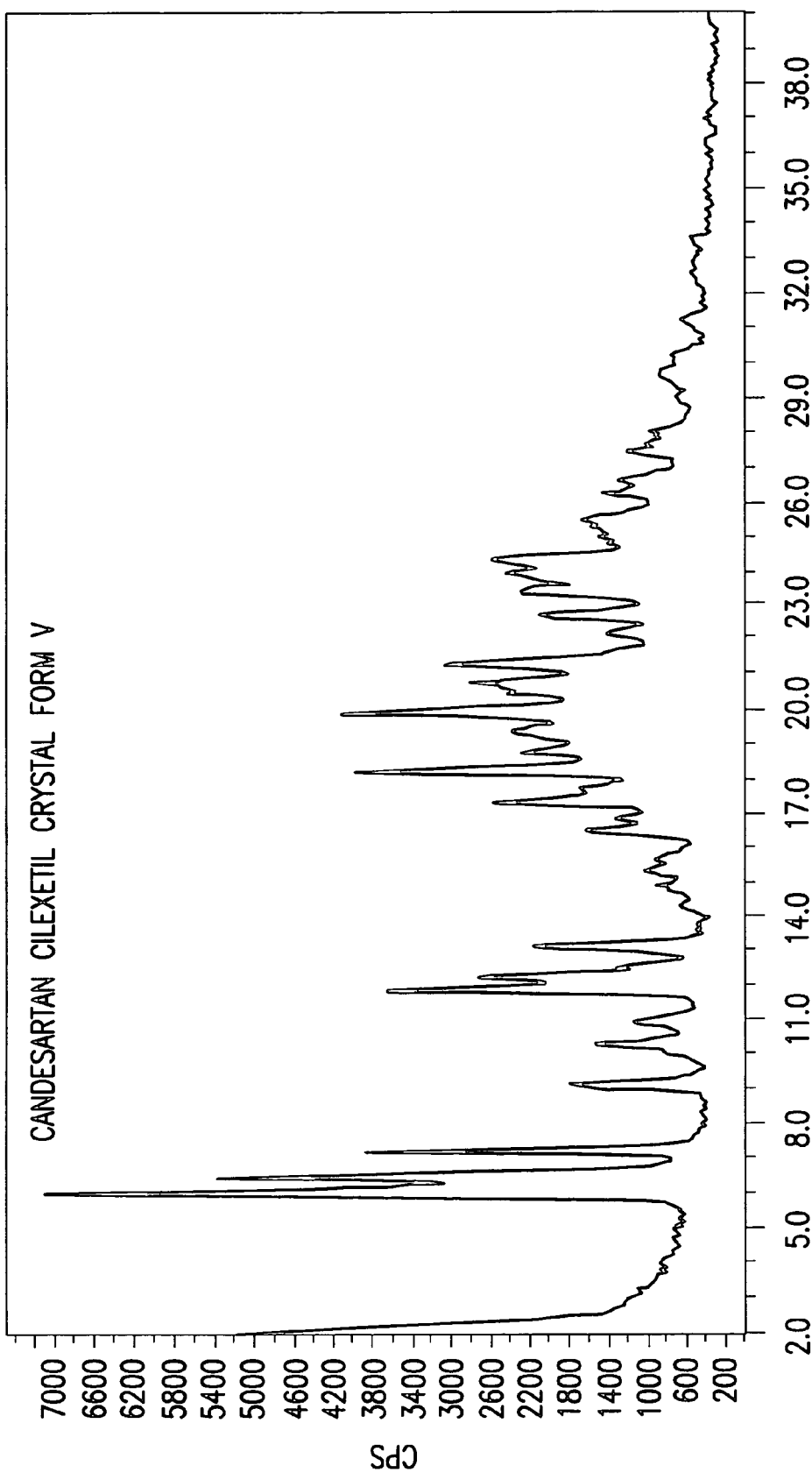
FIG. 3 illustrates the powder X-ray diffraction pattern for candesartan cilexetil Form V.

Yet another embodiment of the invention encompasses another candesartan cilexetil form, herein defined as Form V, which has about 0.1% water by weight, and the weight loss measured by TGA is about 6% by weight. Form V may be a solvate of acetone; with a L.O.D. by TGA of about 6% by weight. Form V may be identified by an X-ray powder diffraction pattern with peaks at about 6.2, 6.5, 7.3, 12.0, and 18.3 degrees two-theta, ±0.2 degrees two-theta. Form V may be identified further by X-ray powder diffraction peaks at about 9.2, 13.2, 17.4, 20.0 and 22.8 degrees two-theta, ±0.2 degrees two-theta. See FIG. 3.

Figure 4:
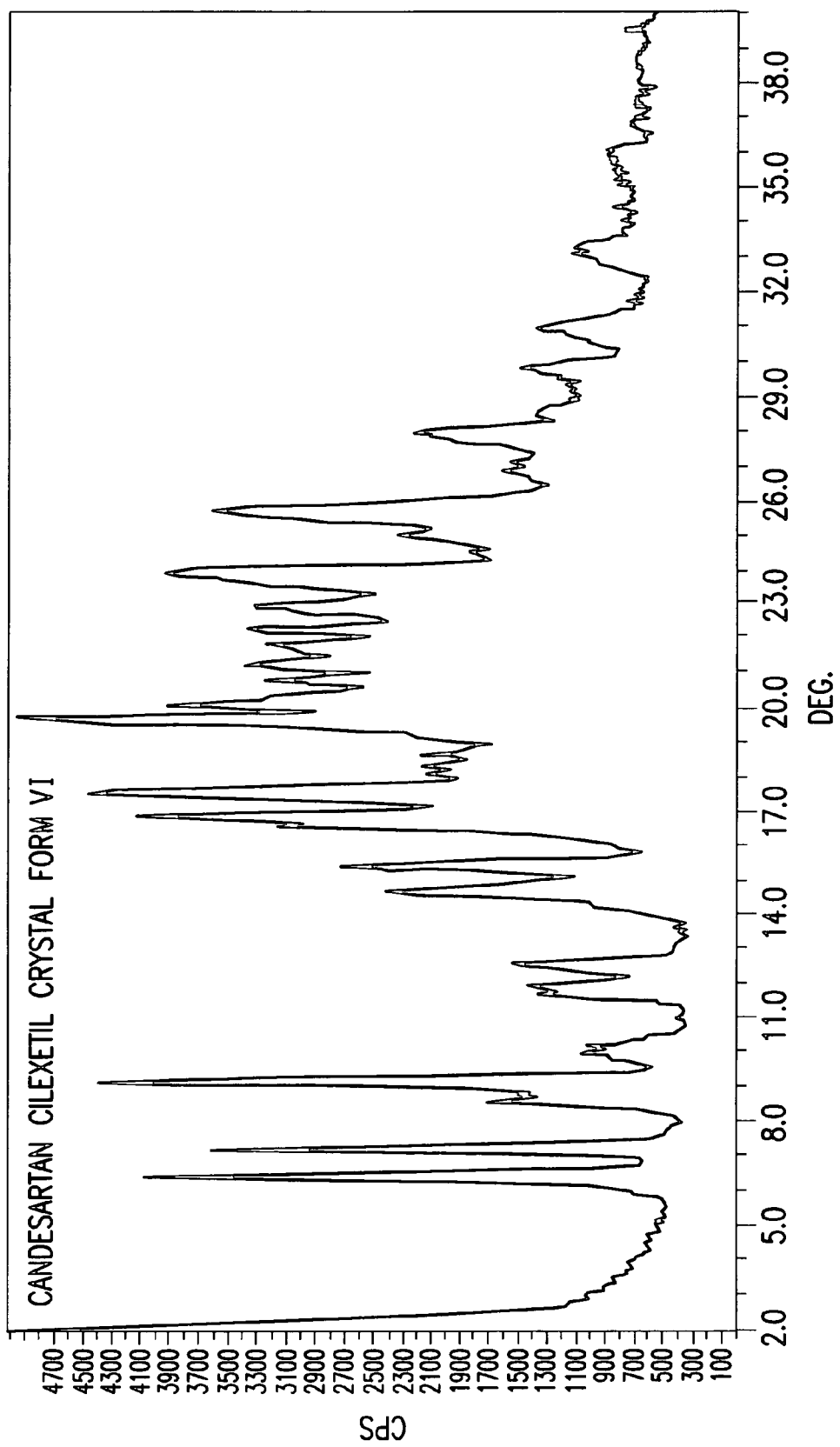
FIG. 4 illustrates the powder X-ray diffraction pattern for candesartan cilexetil Form VI.

Another embodiment of the invention encompasses another candesartan cilexetil form, herein defined as Form VI, which has about 0.4% water by weight, and the weight loss measured by TGA is about 17% by weight. Form VI may be a dichloromethane/heptane solvate; with a L.O.D. by TGA of about 17% by weight. Form VI may be identified by an X-ray powder diffraction pattern with peaks at about 6.5, 7.3, 9.3, 17.6, and 19.8 degrees two-theta, ±0.2 degrees two-theta. Form VI may be identified further by X-ray powder diffraction peaks at about 12.6, 14.8, 15.5, 24.0, and 25.7 degrees two-theta, ±0.2 degrees two-theta. See FIG. 4.

Figure 5:
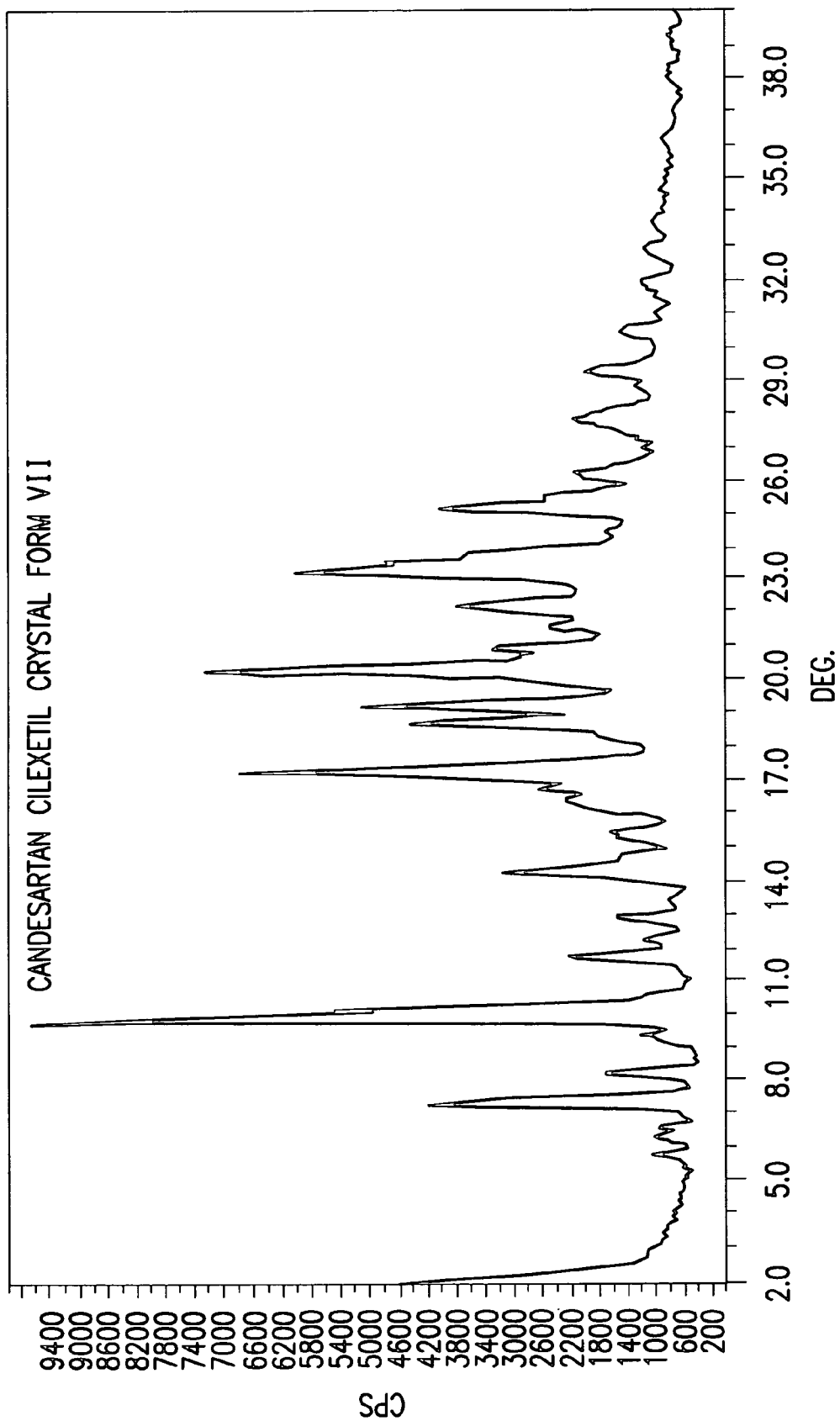
FIG. 5 illustrates the powder X-ray diffraction pattern for candesartan cilexetil Form VII.

Yet another embodiment of the invention encompasses another candesartan cilexetil form, herein defined as Form VII, which has about 0.1% water by weight, and the weight loss measured by TGA is about 3% to about 7% by weight. Form VII may be a solvate of toluene; with a L.O.D. by TGA of about 7% by weight. Form VII may also be a dichloromethane/heptane solvate; with a L.O.D. by TGA of about 3% by weight. Form VII may be identified by an X-ray powder diffraction pattern with peaks at about 7.4, 10.1, 17.5, 20.5, and 23.4 degrees two-theta, ±0.2 degrees two-theta. Form VII may be identified further by X-ray powder diffraction peaks at about 8.3, 14.4, 18.8, 19.4, and 25.3 degrees two-theta, ±0.2 degrees two-theta. See FIG. 5.

Figure 6:
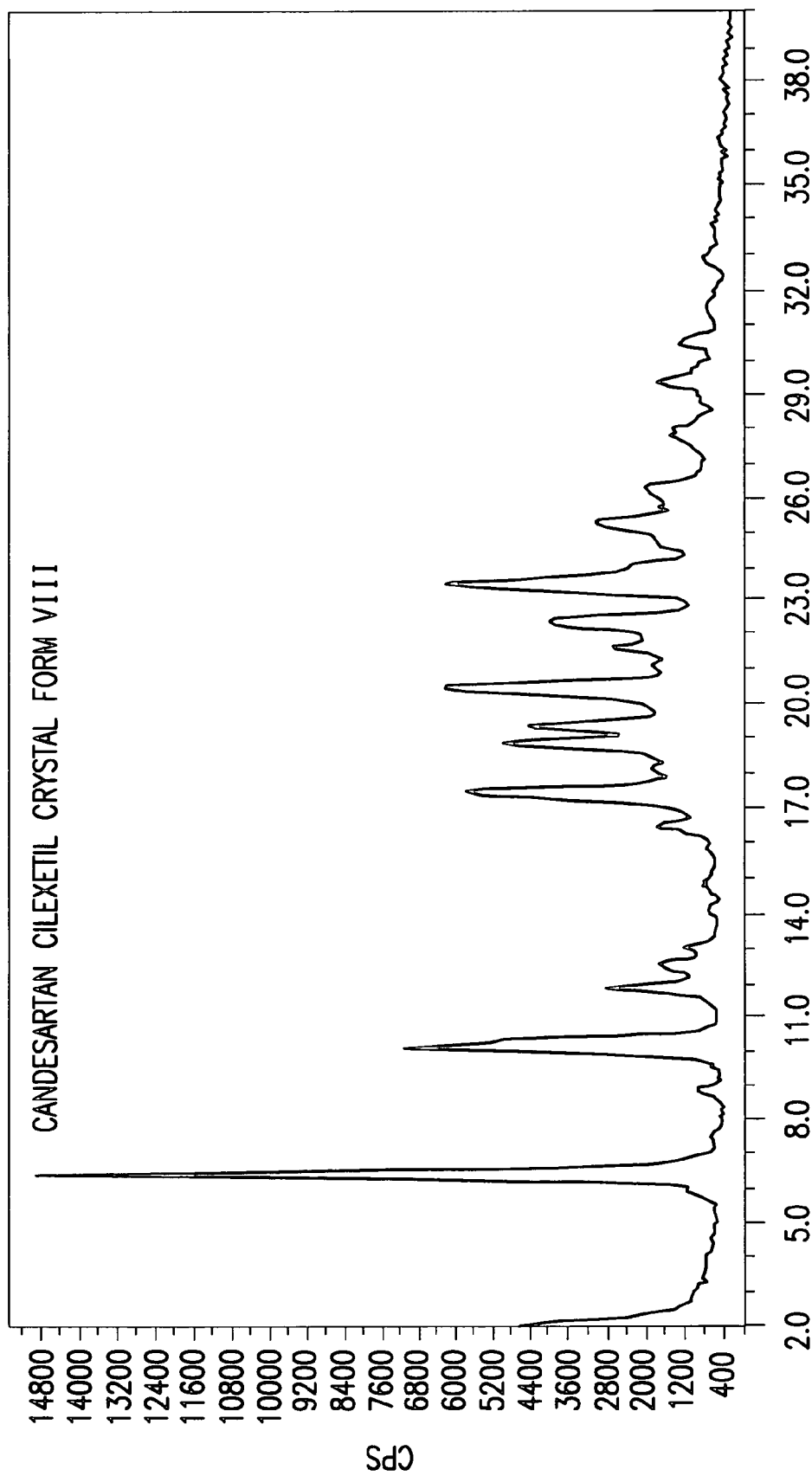
FIG. 6 illustrates the powder X-ray diffraction pattern for candesartan cilexetil Form VIII.

Another embodiment of the invention encompasses another candesartan cilexetil form, herein defined as Form VIII, which has about 0.2% water by weight, and the weight loss measured by TGA is about 3% to about 4% by weight. Form VIII may be a solvate of methyl ethyl ketone; with a L.O.D. by TGA of about 4% by weight. Form VIII may be identified by an X-ray powder diffraction pattern with peaks at about 6.4, 10.2, 17.5, 20.5, and 23.5 degrees two-theta, ±0.2 degrees two-theta. Form VIII may be identified further by X-ray powder diffraction peaks at about 11.9, 18.9, 19.4, 22.5, and 25.3 degrees two-theta, ±0.2 degrees two-theta. See FIG. 6.

Figure 7:
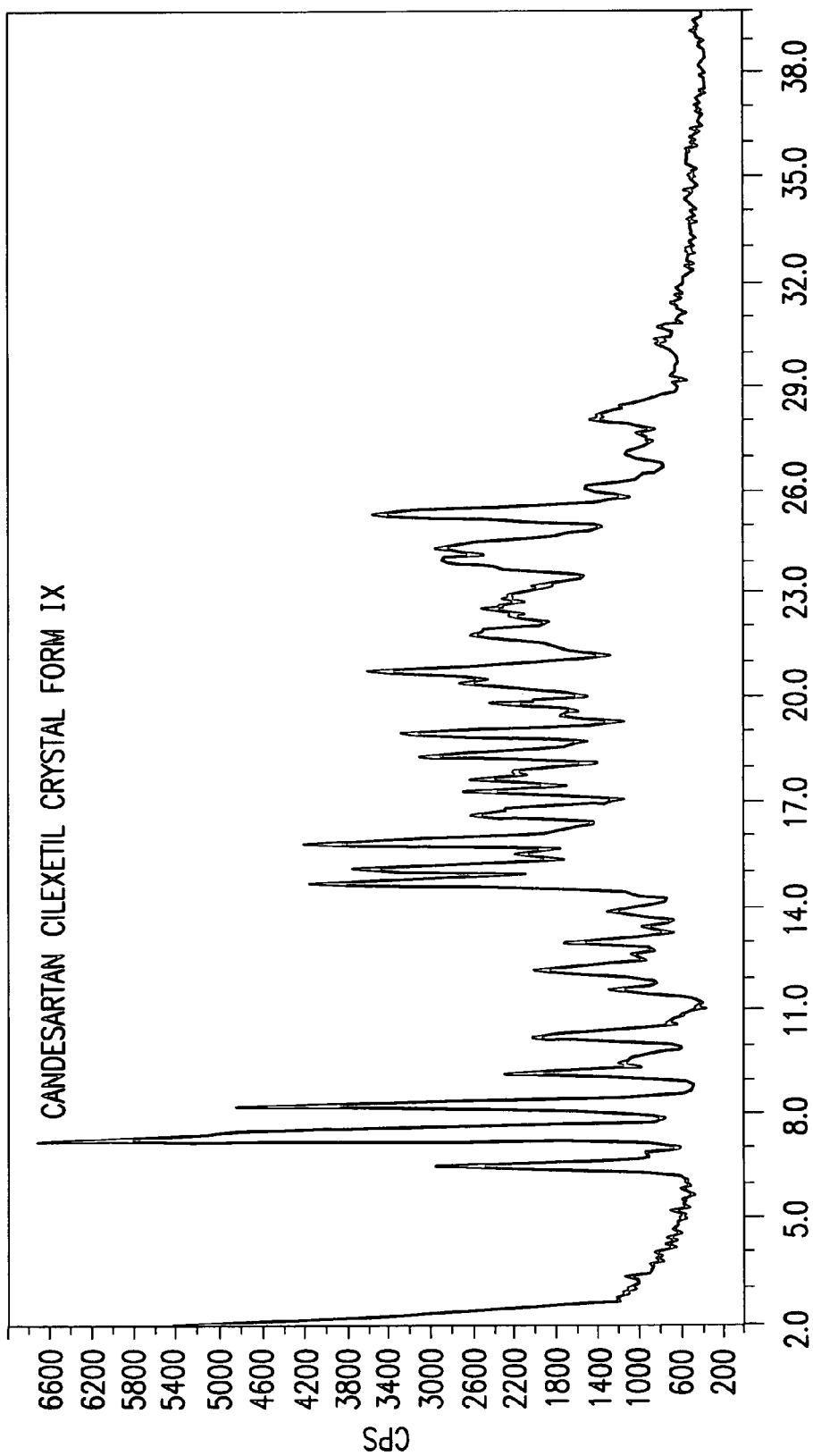
FIG. 7 illustrates the powder X-ray diffraction pattern for candesartan cilexetil Form IX.

Yet another embodiment of the invention encompasses another candesartan cilexetil form, herein defined as Form IX, which has about 0.4% water by weight. Form IX may be identified by an X-ray powder diffraction pattern with peaks at about 6.5, 7.4, 8.4, 15.9, and 25.3 degrees two-theta, ±0.2 degrees two-theta. Form IX may be identified further by X-ray powder diffraction peaks at about 9.2, 10.2, 14.8, 19.1, and 20.8 degrees two-theta, ±0.2 degrees two-theta. See FIG. 7.

Figure 8:
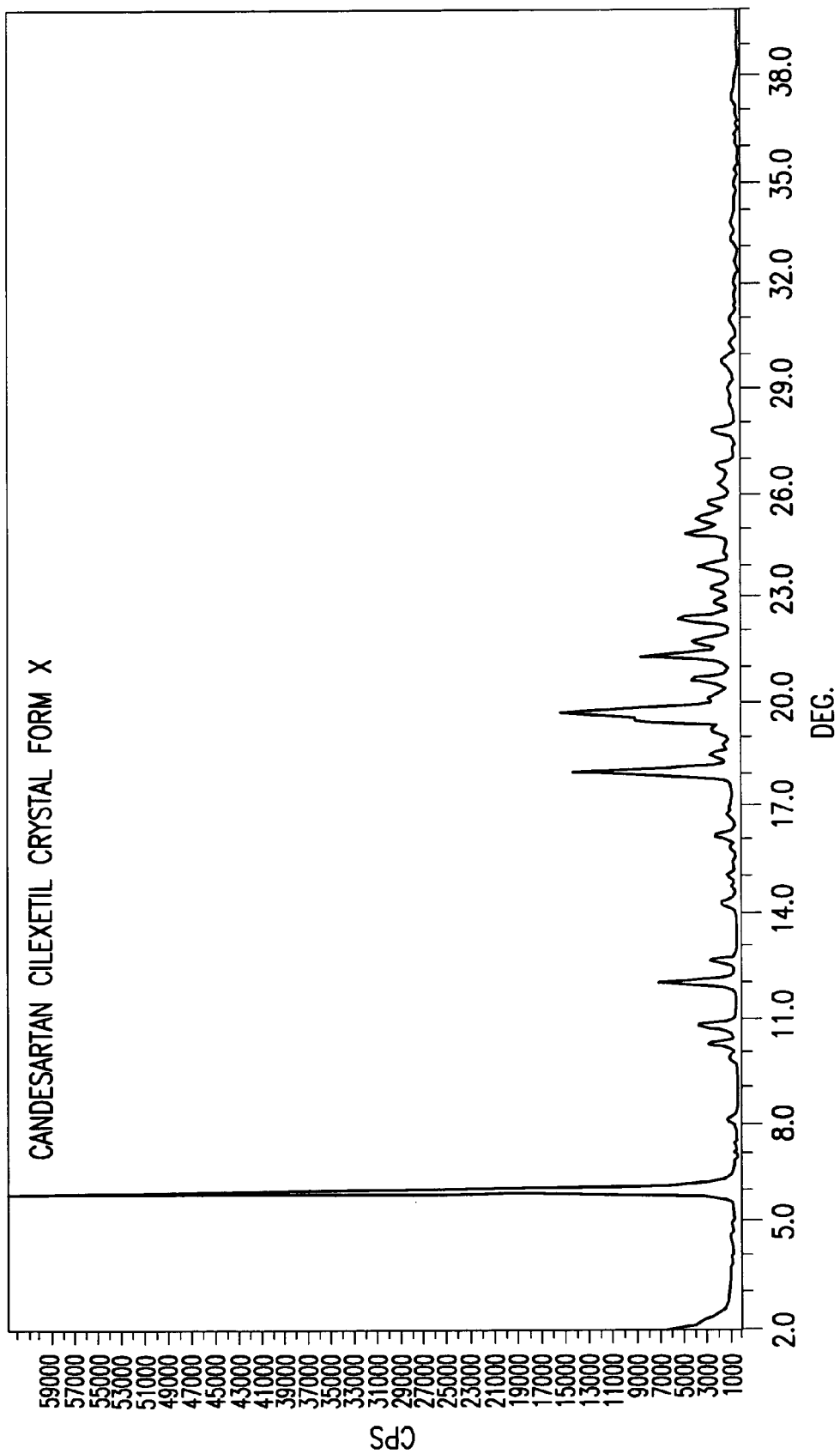
FIG. 8 illustrates the powder X-ray diffraction pattern for candesartan cilexetil Form X.

Another embodiment of the invention encompasses another candesartan cilexetil form, herein defined as Form X, which has about 5% to 11% water by weight, and the weight loss measured by TGA is about 15% to about 17% by weight. Form X may be a dioxane/water solvate; with a L.O.D. by TGA of about 16% by weight. Form X may be identified by an X-ray powder diffraction pattern with peaks at about 6.0, 12.1, 18.1, 19.7, and 21.3 degrees two-theta, ±0.2 degrees two-theta. Form X may be identified further by X-ray powder diffraction peaks at about 10.8, 20.7, 22.4, 24.9, and 27.9 degrees two-theta, ±0.2 degrees two-theta. See FIG. 8.

Figure 9:
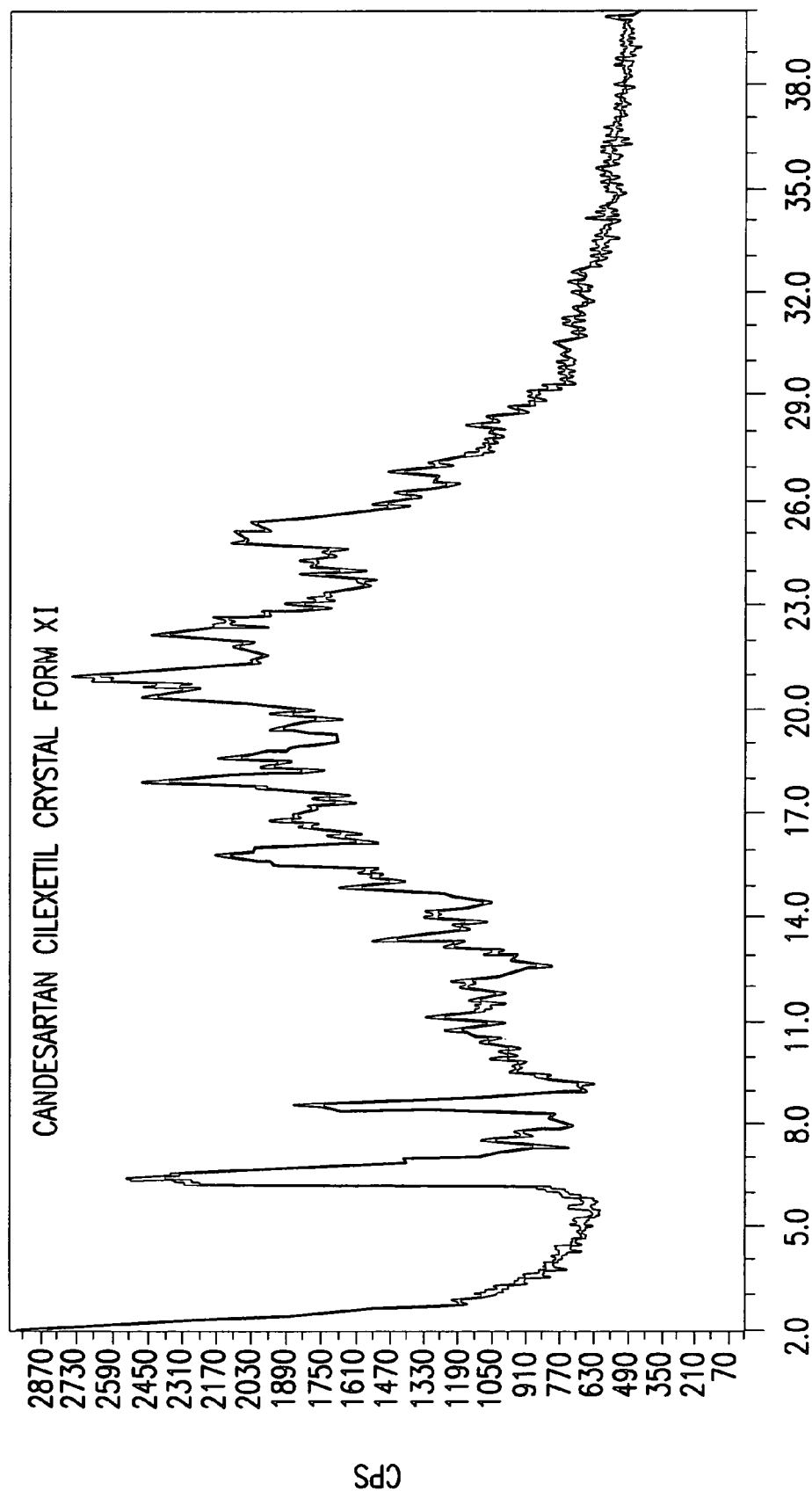
FIG. 9 illustrates the powder X-ray diffraction pattern for candesartan cilexetil Form XI.

Yet another embodiment of the invention encompasses another candesartan cilexetil form, herein defined as Form XI, which has about 0.7% water by weight, and the weight loss measured by TGA is about 6% by weight. Form XI may be a chloroform/heptane solvate; with a L.O.D. by TGA of about 6% by weight. Form XI may be identified by an X-ray powder diffraction pattern with peaks at about 6.5, 8.5, 18.0, 21.1, and 24.9 degrees two-theta, ±0.2 degrees two-theta. Form XI maybe identified further by X-ray powder diffraction peaks at about 7.4, 13.4, 15.8, 18.6, and 22.2 degrees two-theta, ±0.2 degrees two-theta. See FIG. 9.

Figure 10:
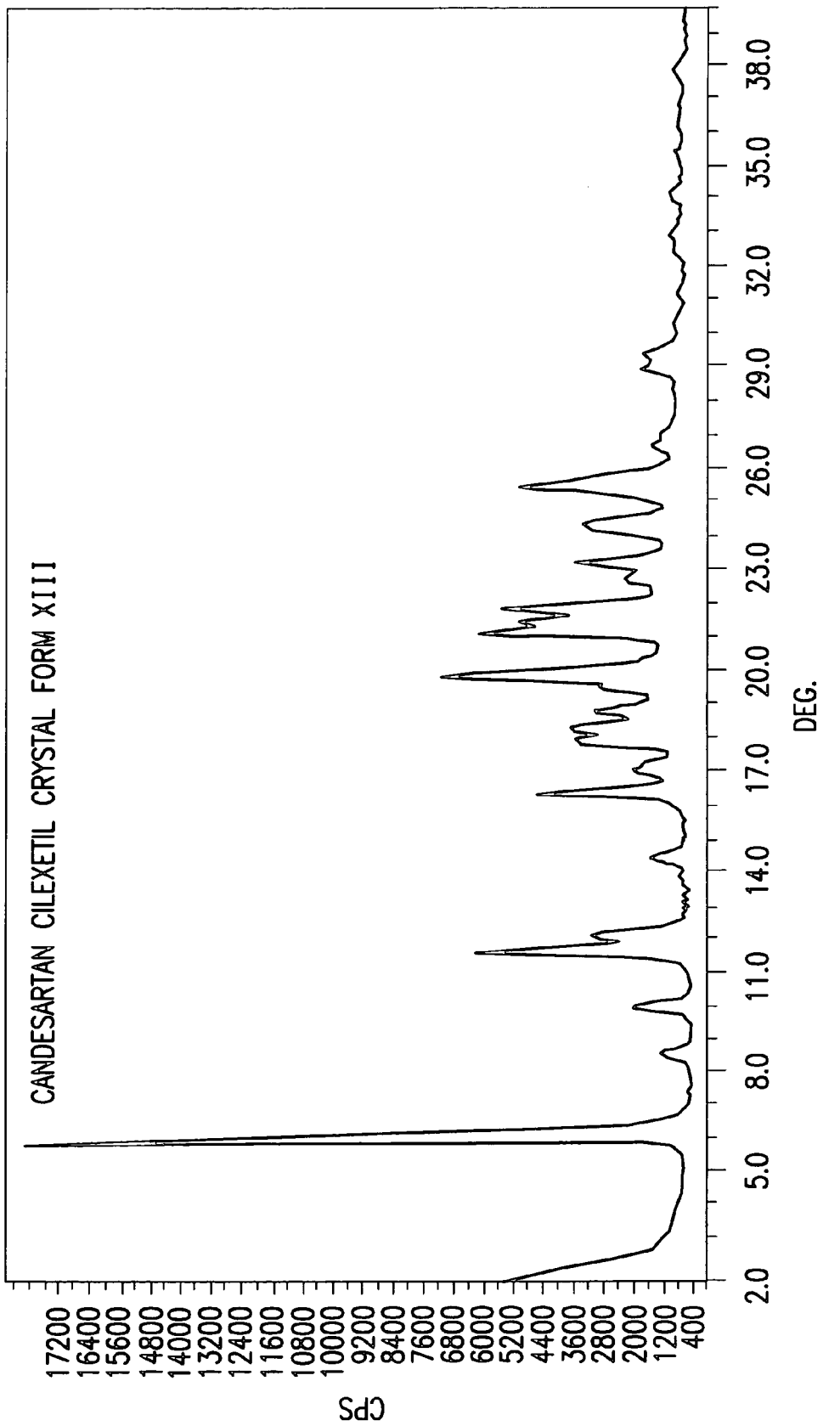
FIG. 10 illustrates the powder X-ray diffraction pattern for candesartan cilexetil Form XIII.

Another embodiment of the invention encompasses another candesartan cilexetil form, herein defined as Form XIII, which has about 0.2% water by weight, and the weight loss measured by TGA is about 8% by weight. Form XIII may be a dichloromethane/isoamyl acetate solvate; with a L.O.D. by TGA of about 8% by weight. Form XIII may be identified by an X-ray powder diffraction pattern with peaks at about 6.2, 11.8, 16.5, 20.1, and 25.7 degrees two-theta, ±0.2 degrees two-theta. Form XIII may be identified further by X-ray powder diffraction peaks at about 10.1, 18.1, 21.3, 23.4, and 24.6 degrees two-theta, ±0.2 degrees two-theta. See FIG. 10.

Figure 11:
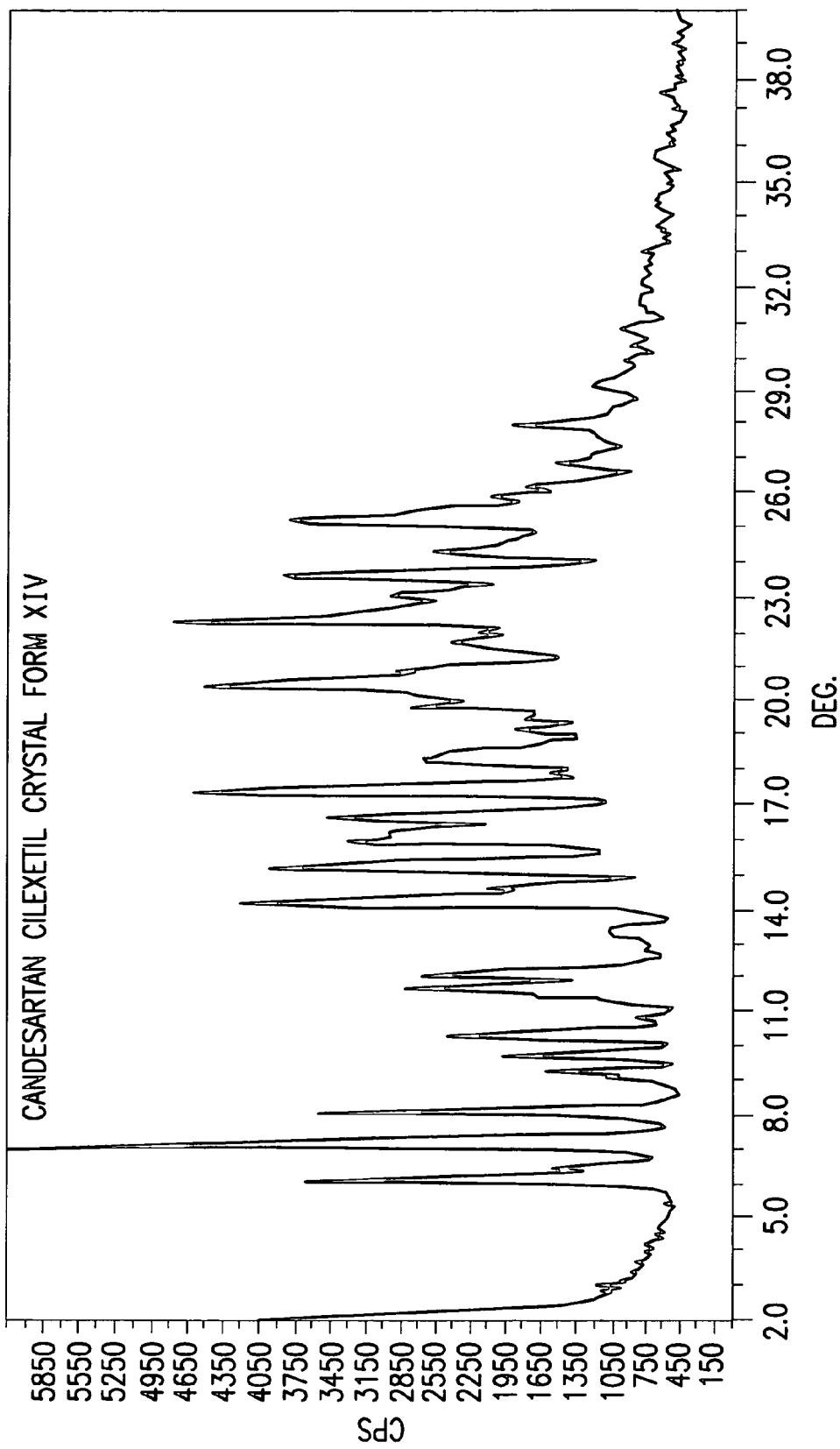
FIG. 11 illustrates the powder X-ray diffraction pattern for candesartan cilexetil Form XIV.

Yet another embodiment of the invention encompasses another candesartan cilexetil form, herein defined as Form XIV, which has about 0.3% water by weight, and the weight loss measured by TGA is about 16% by weight. Form XIV may be a solvate of dichloromethane; with a L.O.D. by TGA of about 16% by weight. Form XIV may be identified by an X-ray powder diffraction pattern with peaks at about 6.1, 7.3, 14.2, 17.5, and 22.4 degrees two-theta, ±0.2 degrees two-theta. Form XIV may be identified further by X-ray powder diffraction peaks at about 8.1, 10.4, 15.3, 20.5, and 25.3 degrees two-theta, ±0.2 degrees two-theta. See FIG. 11.

Figure 12:
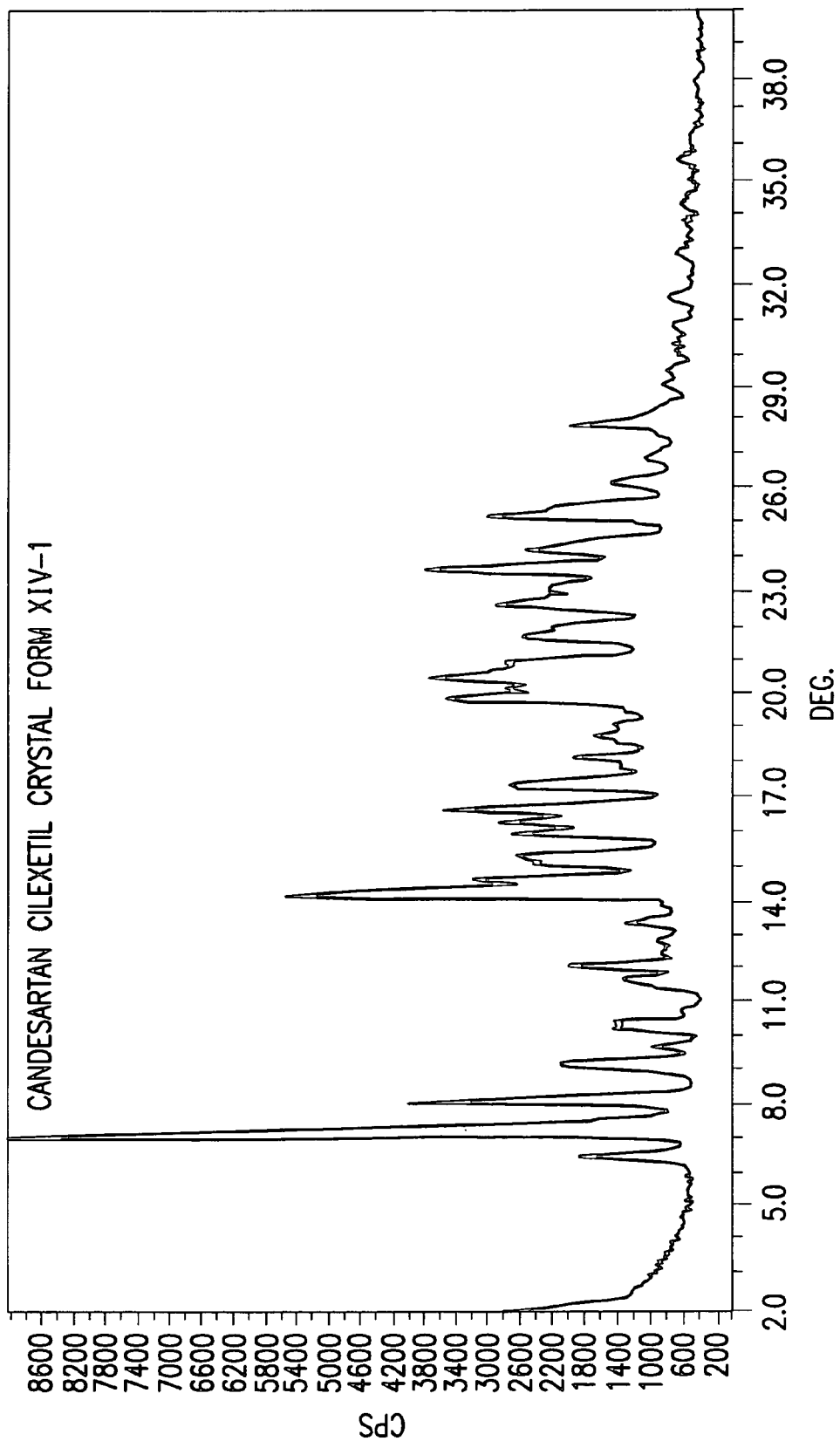
FIG. 12 illustrates the powder X-ray diffraction pattern for candesartan cilexetil Form XIV-1.

Yet another embodiment of the invention encompasses another candesartan cilexetil form, herein defined as Form XIV-1. Form XIV-1 may be characterized by at least one of an X-ray powder diffraction or by an FTIR. The X-ray powder diffraction pattern has peaks at about 7.3, 8.2, 14.3, 20.5, and 23.8 degrees two-theta, ±0.2 degrees two-theta, as substantially depicted in FIG. 12. Form XIV-1 may be further characterized by X-ray powder diffraction peaks at about 6.4, 9.3, 16.7, 25.3, and 28.0. The FTIR spectrum has characteristic absorption bands at about 1733, 1479, 1359, 1288, 1253, and 1085 cm$^{-1}$. See FIG. 20 and FIGS. 21a-c for an expanded view.

Figure 13:
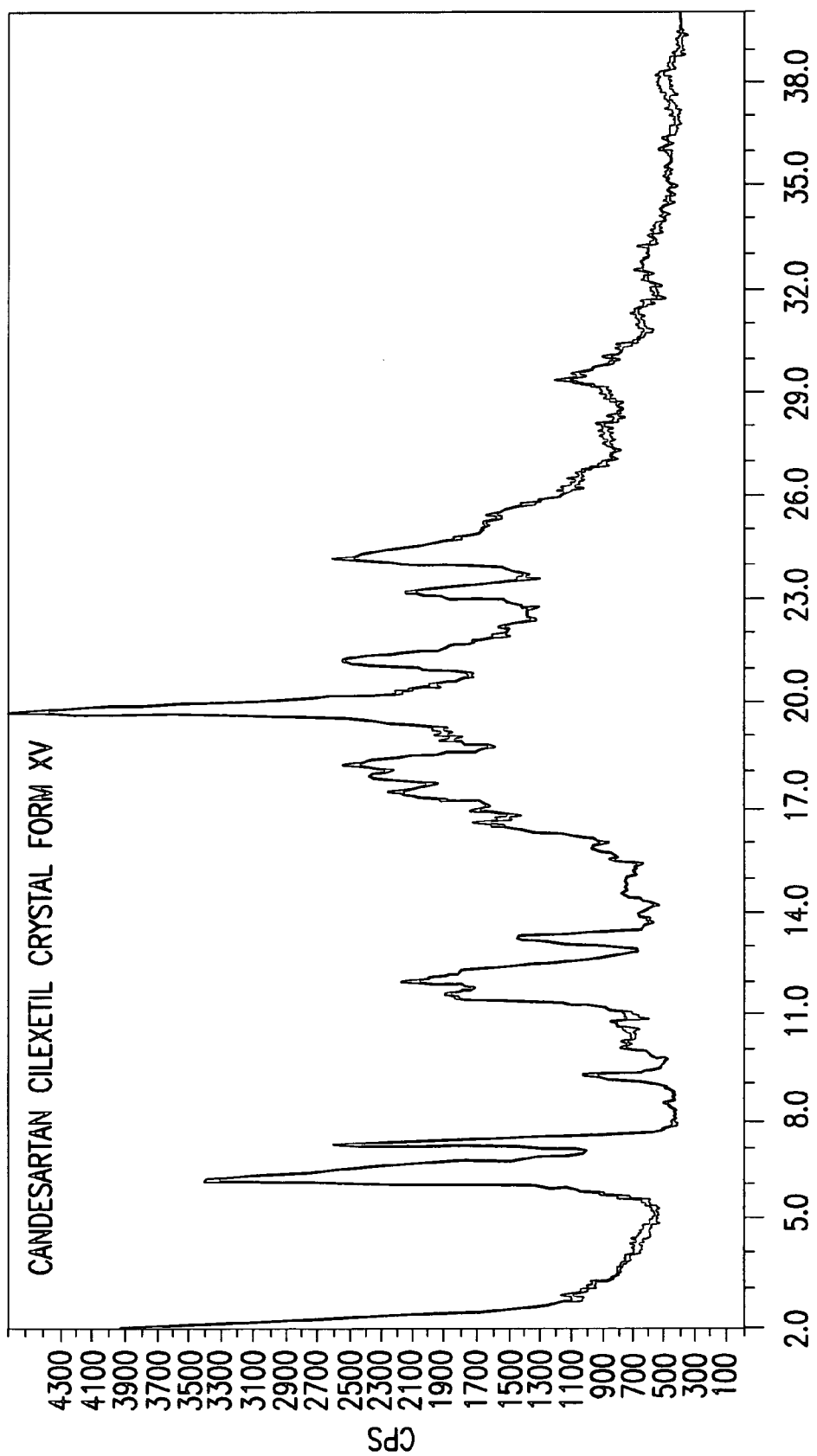
FIG. 13 illustrates the powder X-ray diffraction pattern for candesartan cilexetil Form XV.

Another embodiment of the invention encompasses another candesartan cilexetil form, herein defined as Form XV, which has about 0.5% water by weight, and the weight loss measured by TGA is about 8% by weight. Form XV may be a chloroform/acetonitrile solvate; with a L.O.D. by TGA of about 8% by weight. Form XV may be identified by an X-ray powder diffraction pattern with peaks at about 6.3, 7.3, 20.0, 21.4, and 24.3 degrees two-theta, ±0.2 degrees two-theta. Form XV may be identified further by X-ray powder diffraction peaks at about 9.3, 12.0, 13.3, 18.3, and 23.3 degrees two-theta, ±0.2 degrees two-theta. See FIG. 13.

Figure 14:
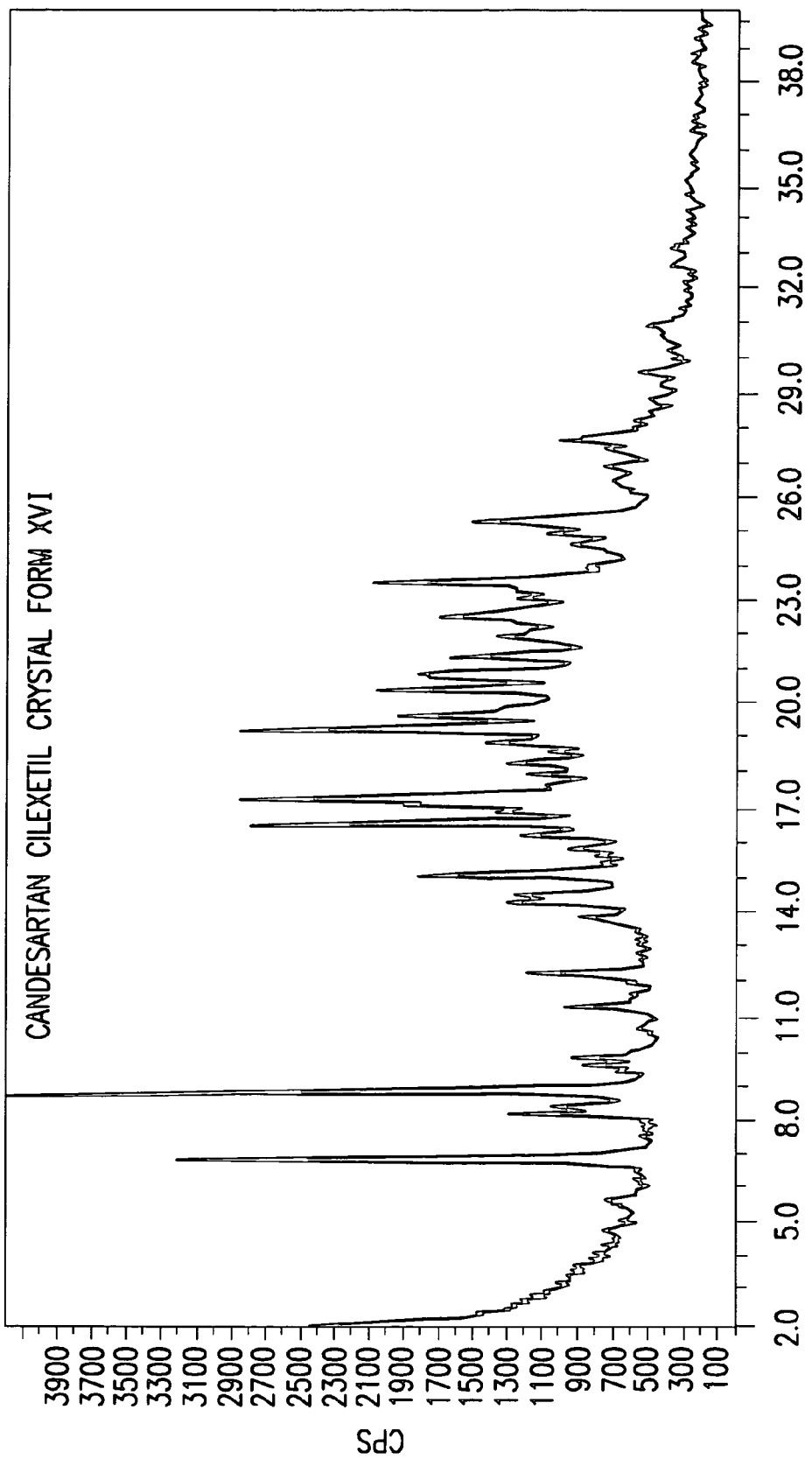
FIG. 14 illustrates the powder X-ray diffraction pattern for candesartan cilexetil Form XVI.

Yet another embodiment of the invention encompasses another candesartan cilexetil form, herein defined as Form XVI, which has about 0.8% water by weight. Form XVI may be identified by an X-ray powder diffraction pattern with peaks at about 7.0, 8.9, 16.7, 17.4, and 19.4 degrees two-theta, ±0.2 degrees two-theta. Form XVI may be identified further by X-ray powder diffraction peaks at about 8.3, 11.3, 15.1, 20.5, and 23.7 degrees two-theta, ±0.2 degrees two-theta. See FIG. 14.

Figure 15:
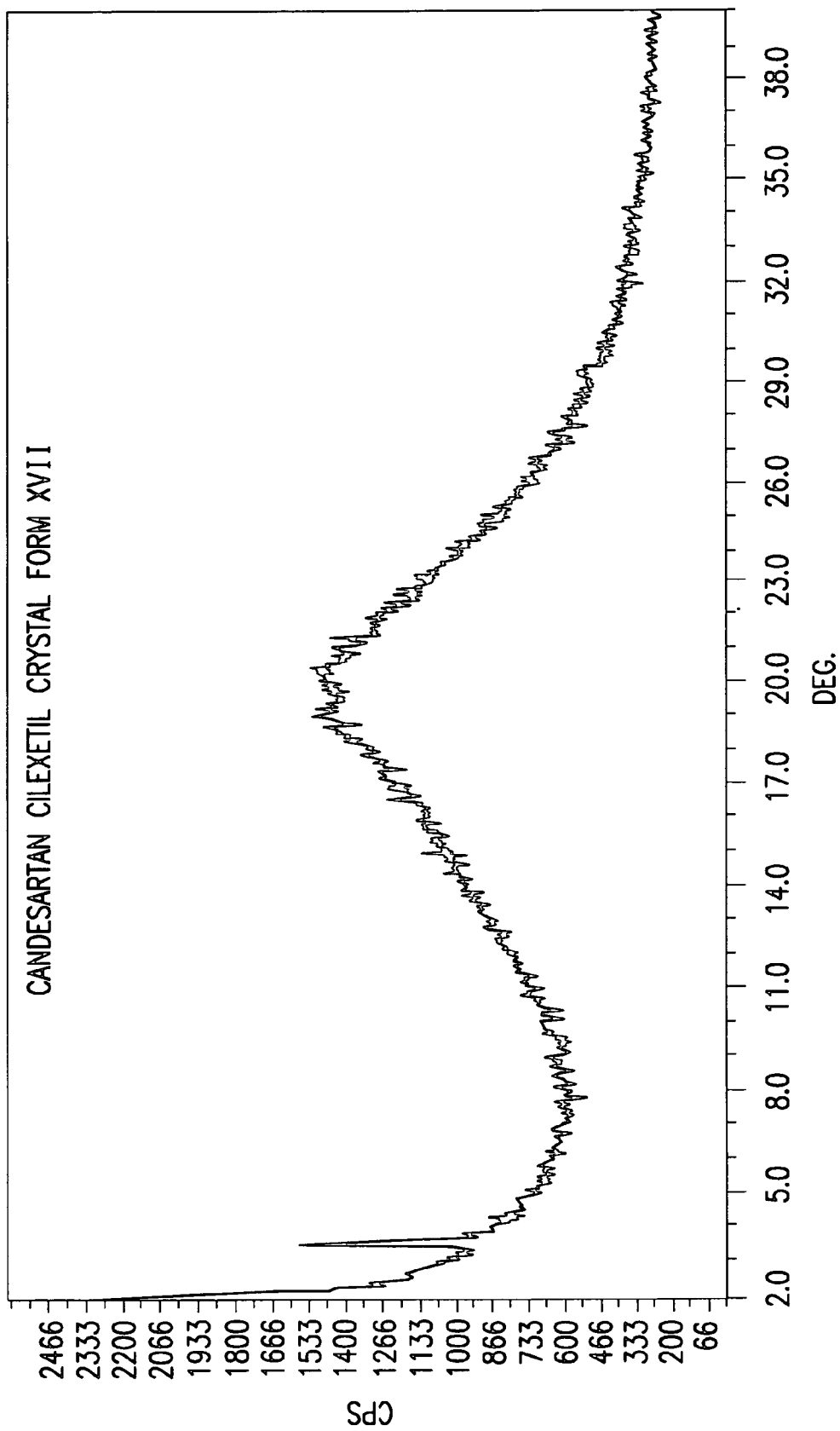
FIG. 15 illustrates the powder X-ray diffraction pattern for candesartan cilexetil Form XVII.

Another embodiment of the invention encompasses another candesartan cilexetil form, herein defined as Form XVII, which has about 1.2% water by weight. Form XVII may be identified by an X-ray powder diffraction pattern with a peak at about 3.6 degrees two-theta, ±0.2 degrees two-theta. Form XVII may be identified further by a broad X-ray powder diffraction peak with a maximum at about 20.0 degrees two-theta, as illustrated by FIG. 15.

Figure 16:
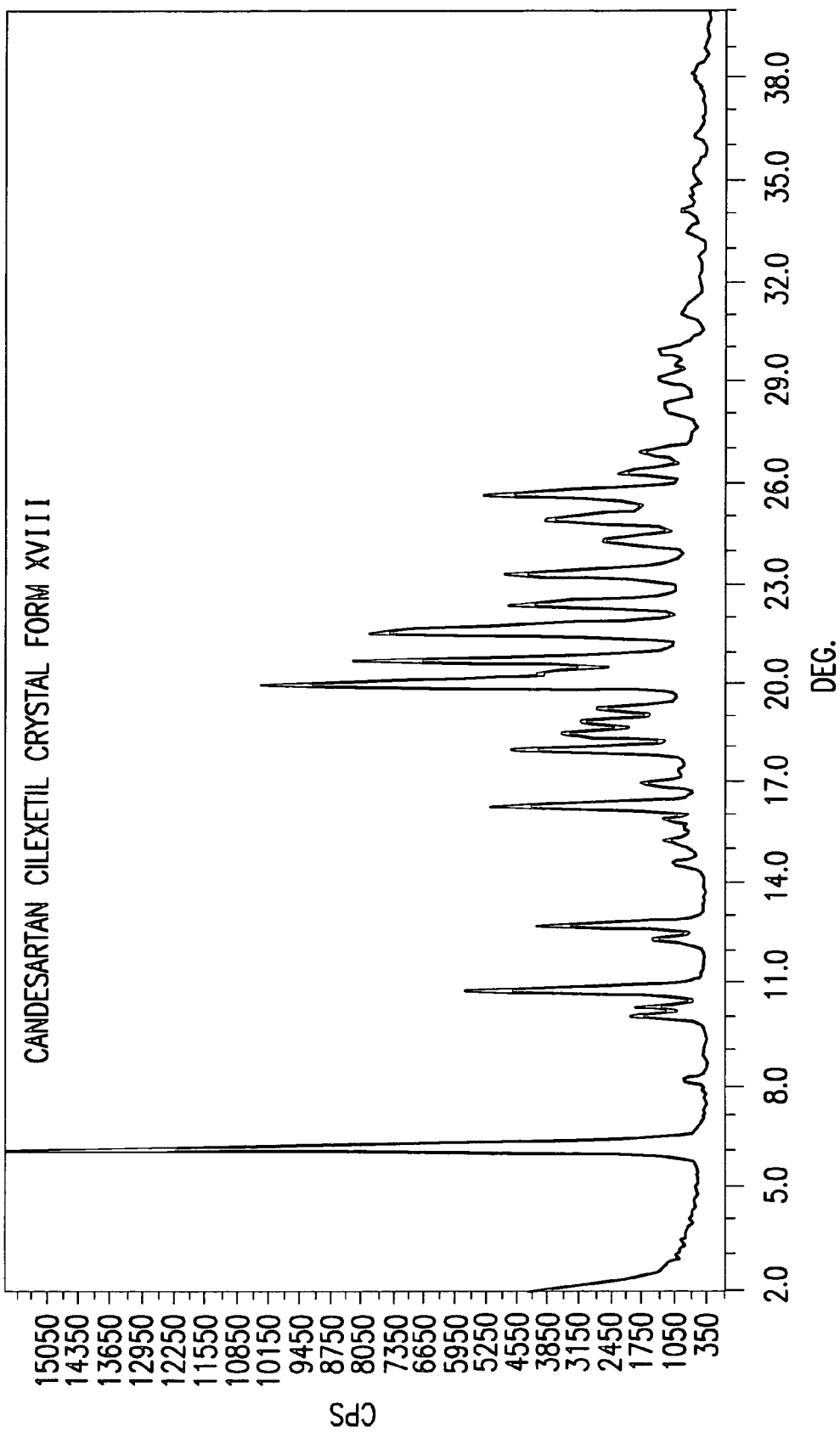
FIG. 16 illustrates the powder X-ray diffraction pattern for candesartan cilexetil Form XVIII.

Another embodiment of the invention encompasses another candesartan cilexetil form, herein defined as Form XVIII, which has about 30% water by weight, and the weight loss measured by TGA is about 35% by weight. Form XVIII may be a dioxane/water solvate; with a L.O.D. by TGA of about 35% by weight. Form XVIII may also be a tetrahydrofuran/water solvate; with a L.O.D. by TGA of about 27% by weight. Form XVIII may be identified by an X-ray powder diffraction pattern with peaks at about 6.2, 10.8, 20.1, 20.7, and 21.6 degrees two-theta, ±0.2 degrees two-theta. Form XVIII may be identified further by X-ray powder diffraction peaks at about 12.8, 16.3, 18.0, 23.3, and 25.7 degrees two-theta, ±0.2 degrees two-theta. See FIG. 16.

Figure 17:
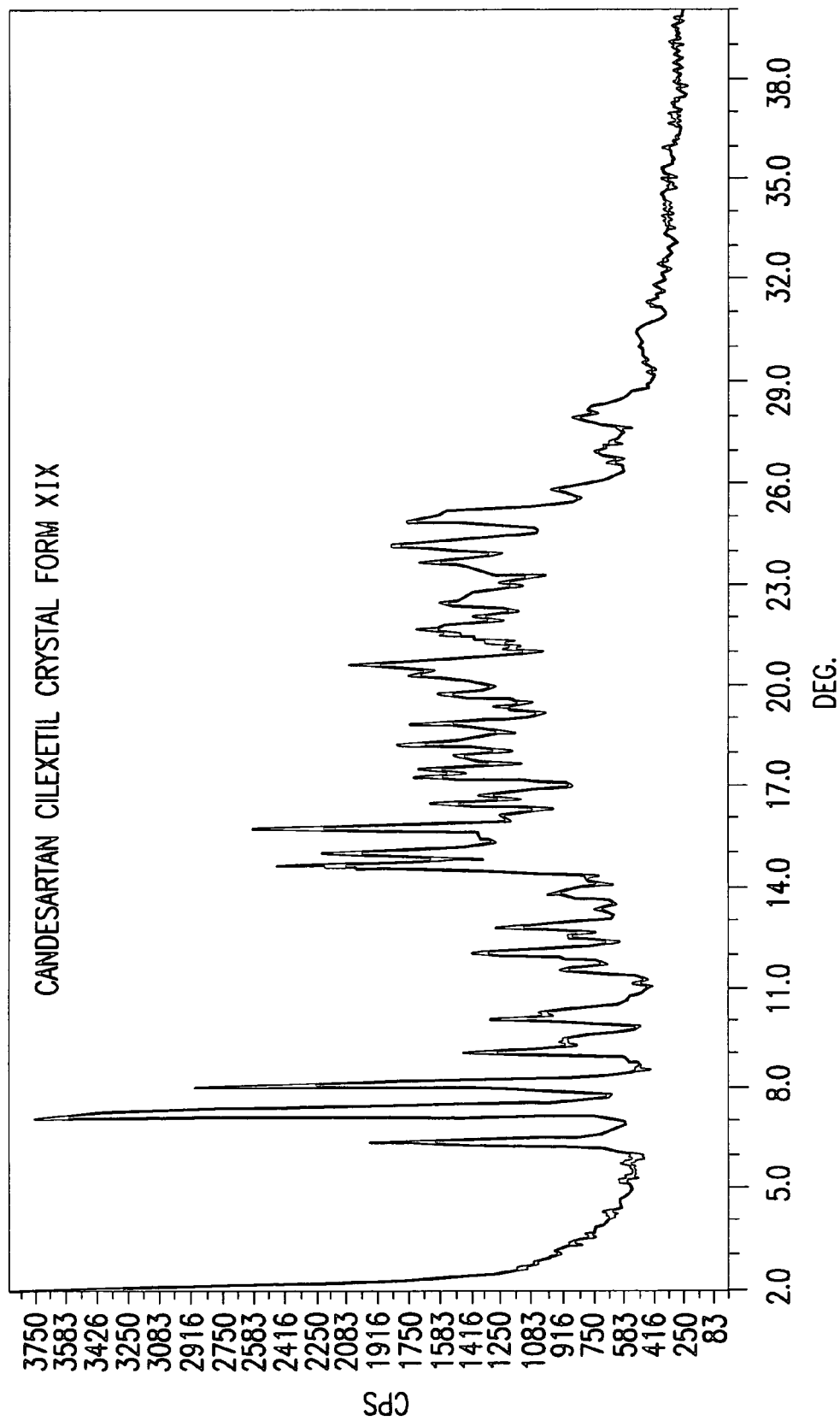
FIG. 17 illustrates the powder X-ray diffraction pattern for candesartan cilexetil Form XIX.

Yet another embodiment of the invention encompasses another candesartan cilexetil form, herein defined as Form XIX, which has about 0.2% water by weight. Form XIX may also have water content of about 11% by weight, and the weight loss measured by TGA is about 16% by weight. Form XIX may be an acetonitrile/water solvate; with a L.O.D. by TGA of about 16% by weight. Form XIX may be identified by an X-ray powder diffraction pattern with peaks at about 6.4, 7.3, 8.2, 14.7, and 15.7 degrees two-theta, ±0.2 degrees two-theta. Form XIX may be identified further by X-ray powder diffraction peaks at about 9.1, 12.0, 15.1, 20.6, and 25.0 degrees two-theta, ±0.2 degrees two-theta. See FIG. 17.

Figure 18:
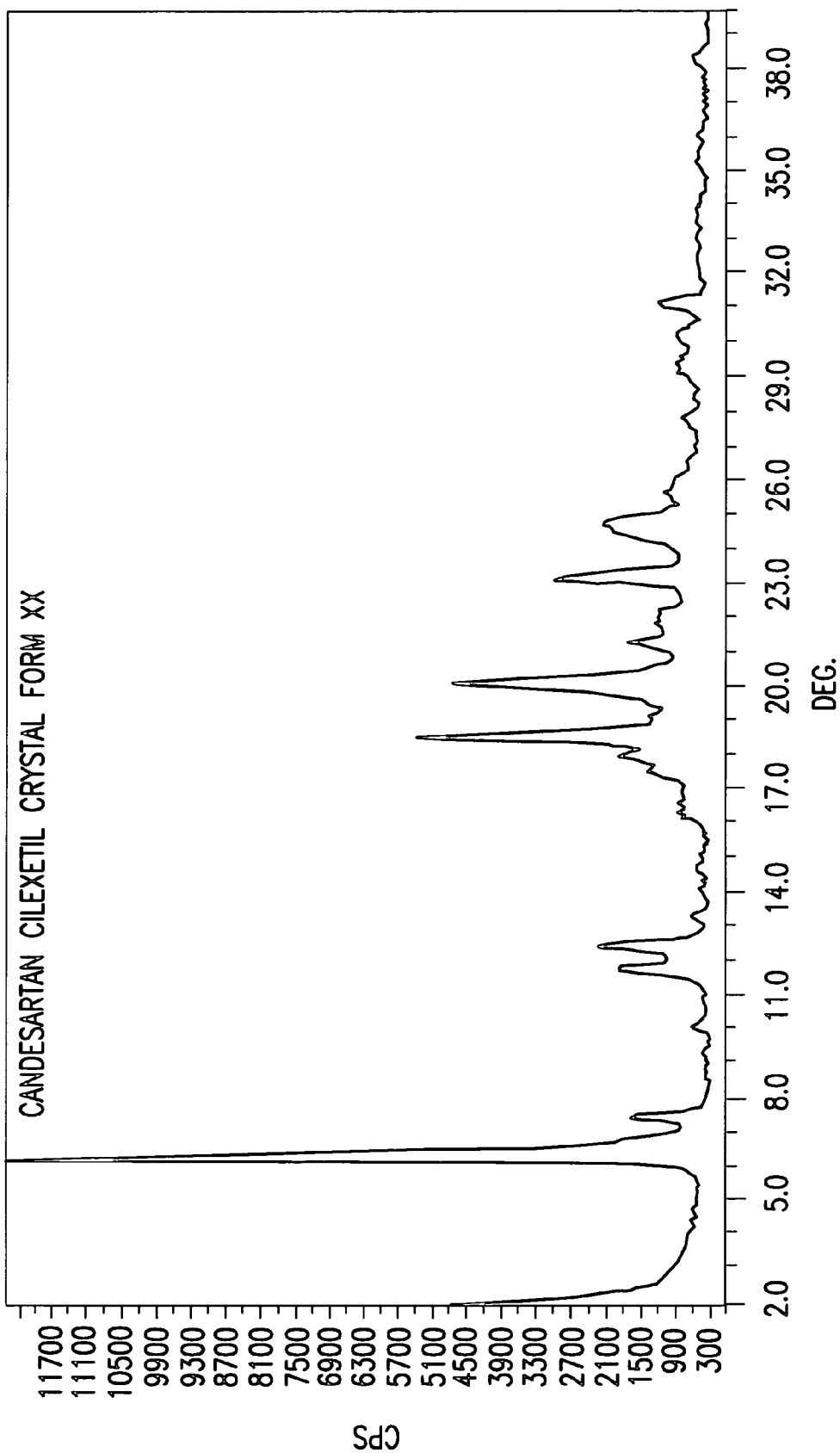
FIG. 18 illustrates the powder X-ray diffraction pattern for candesartan cilexetil Form XX.

Another embodiment of the invention encompasses another candesartan cilexetil form, herein defined as Form XX, which has about 0.1% water by weight, and the weight loss measured by TGA is about 16% by weight. Form XX may be a chloroform/acetonitrile solvate; with a L.O.D. by TGA of about 16% by weight. Form XX may be identified by an X-ray powder diffraction pattern with peaks at about 6.3, 12.5, 18.7, 20.3, and 23.3 degrees two-theta, ±0.2 degrees two-theta. Form XX may be identified further by X-ray powder diffraction peaks at about 7.4, 11.8, 21.5, 25.0, and 31.4 degrees two-theta, ±0.2 degrees two-theta. See FIG. 18.

Figure 19:
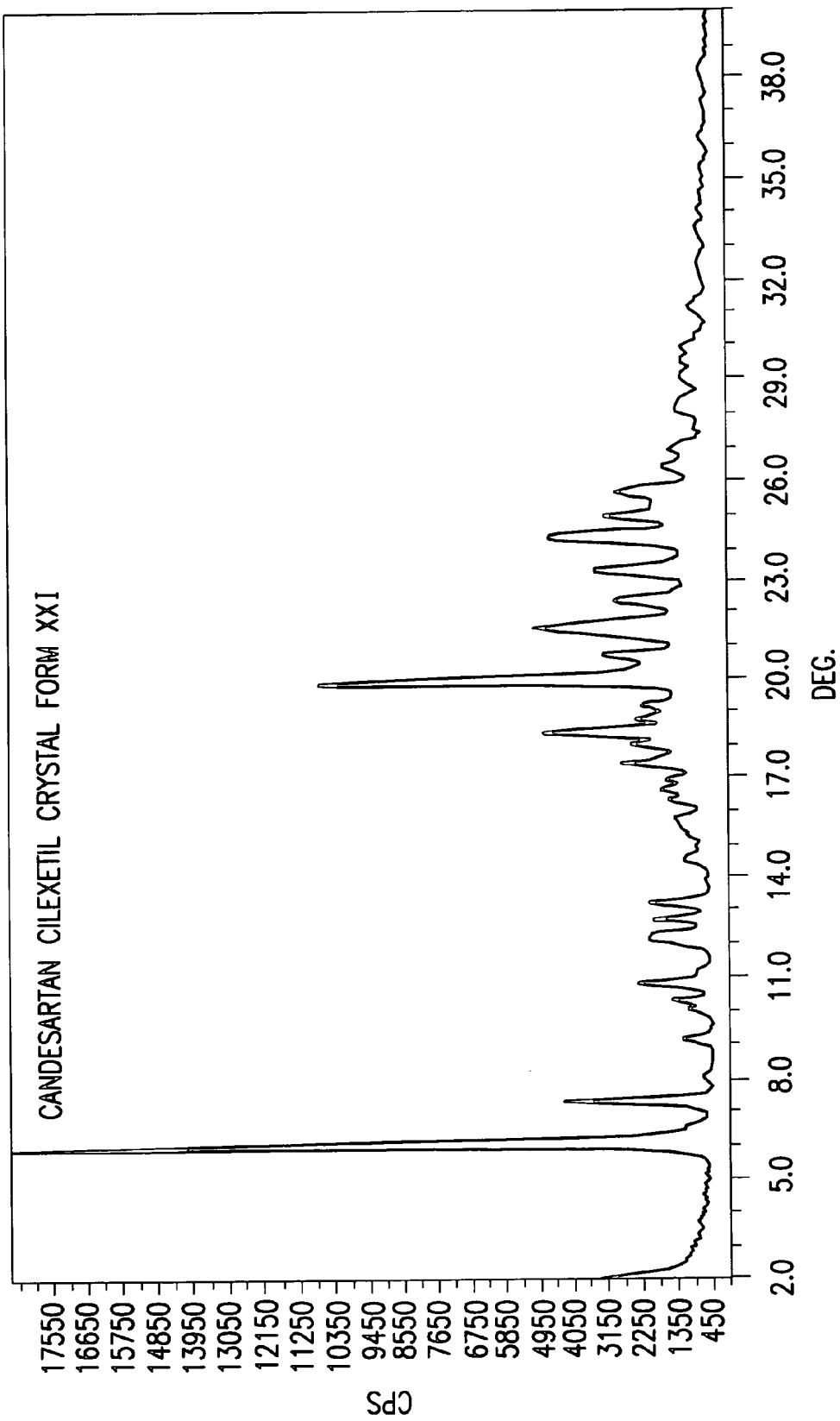
FIG. 19 illustrates the powder X-ray diffraction pattern for candesartan cilexetil Form XXI.
Figure 20:
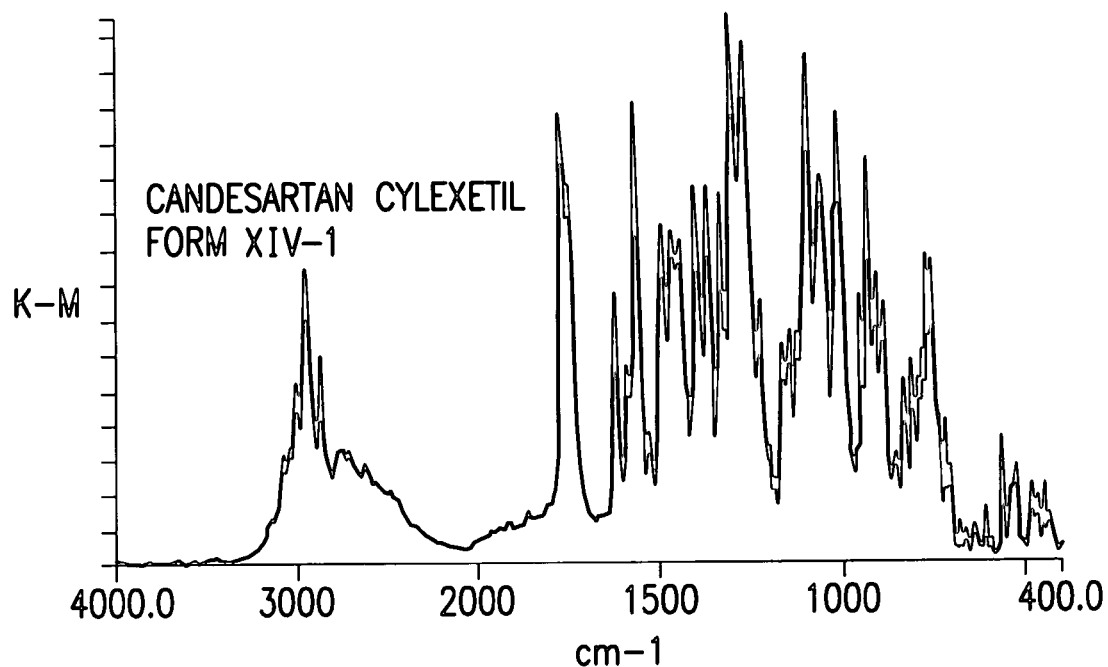
FIG. 20 illustrates the FTIR spectrum for candesartan cilexetil Form XIV-1.
Figure 21A:
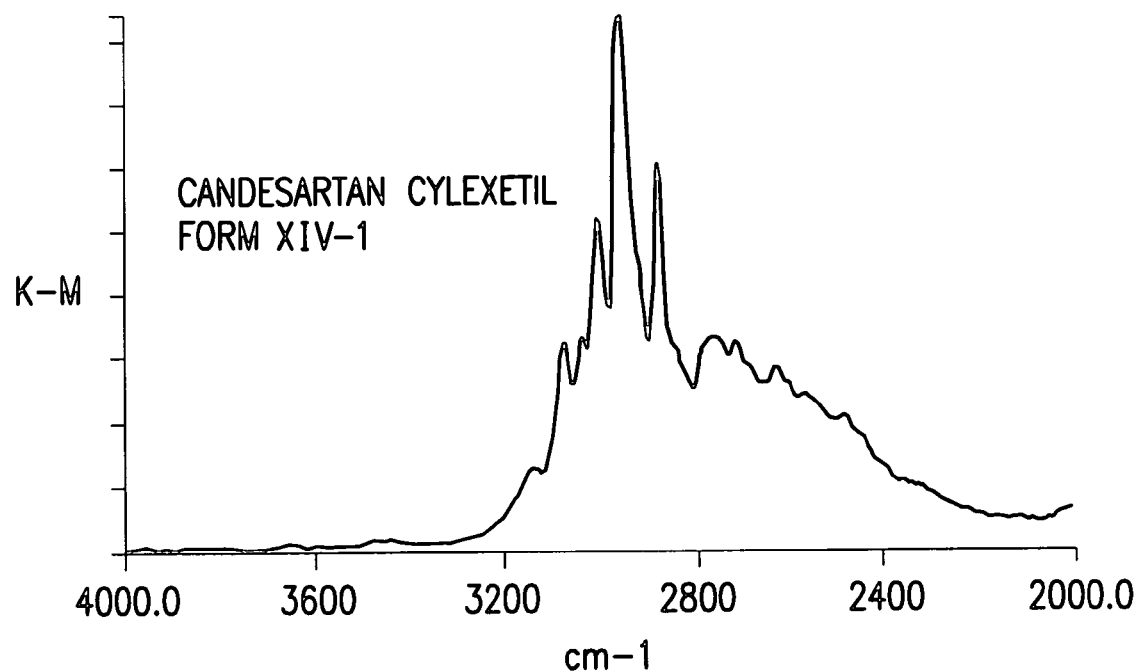
FIGS. 21a-c illustrate the expanded FTIR spectra for candesartan cilexetil Form XIV-1.
Figure 21B:
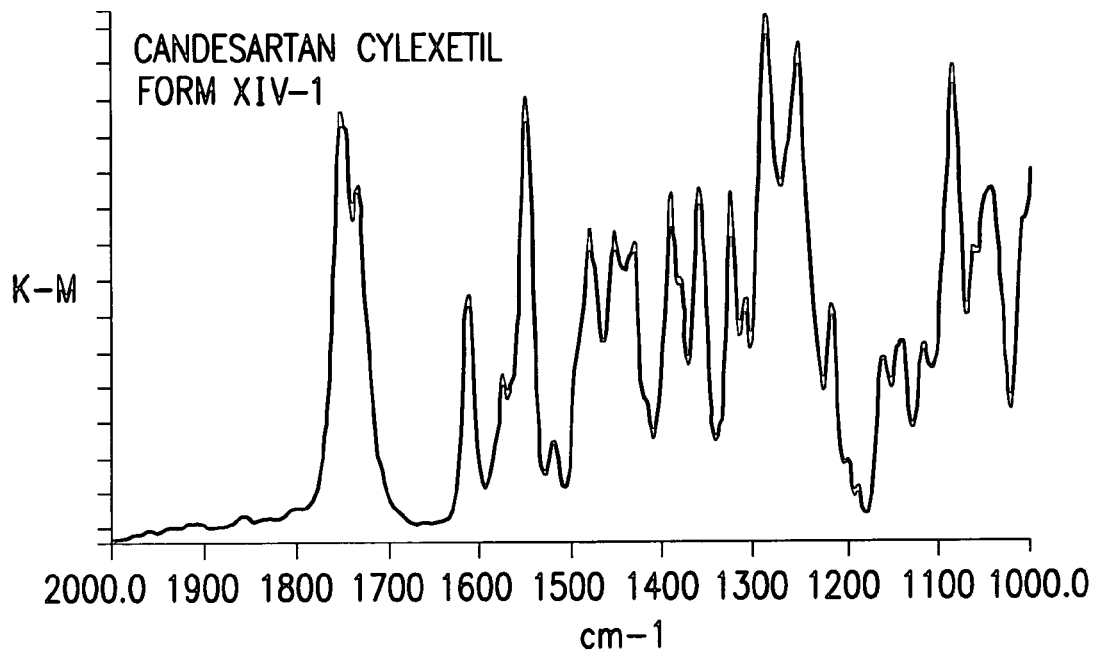
Figure 21C:
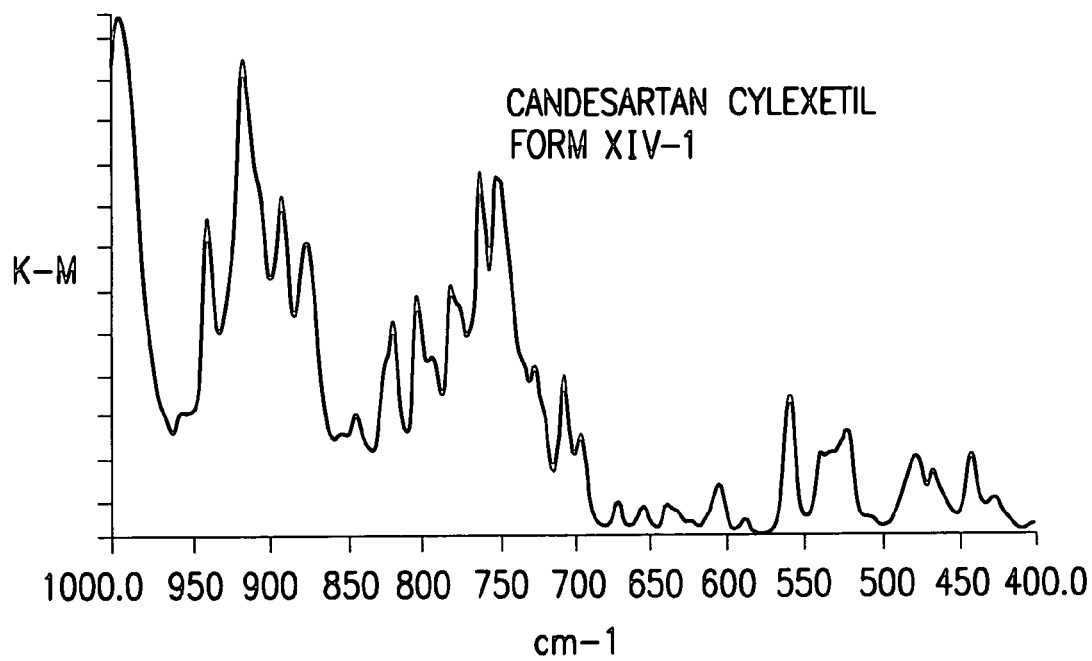

Yet another embodiment of the invention encompasses another candesartan cilexetil form, herein defined as Form XXI, which has about 0.1% water by weight, and the weight loss measured by TGA is about 6% by weight. Form XXI may be a solvate of tetrahydrofuran; with a L.O.D. by TGA of about 6% by weight. Form XXI may be identified by an X-ray powder diffraction pattern with peaks at about 6.1, 7.3, 20.0, 21.6, and 24.3 degrees two-theta, ±0.2 degrees two-theta. Form XXI may be identified further by X-ray powder diffraction peaks at about 10.8, 18.3, 22.4, 23.3, and 25.6 degrees two-theta, ±0.2 degrees two-theta. See FIG. 19.

Figure 22:
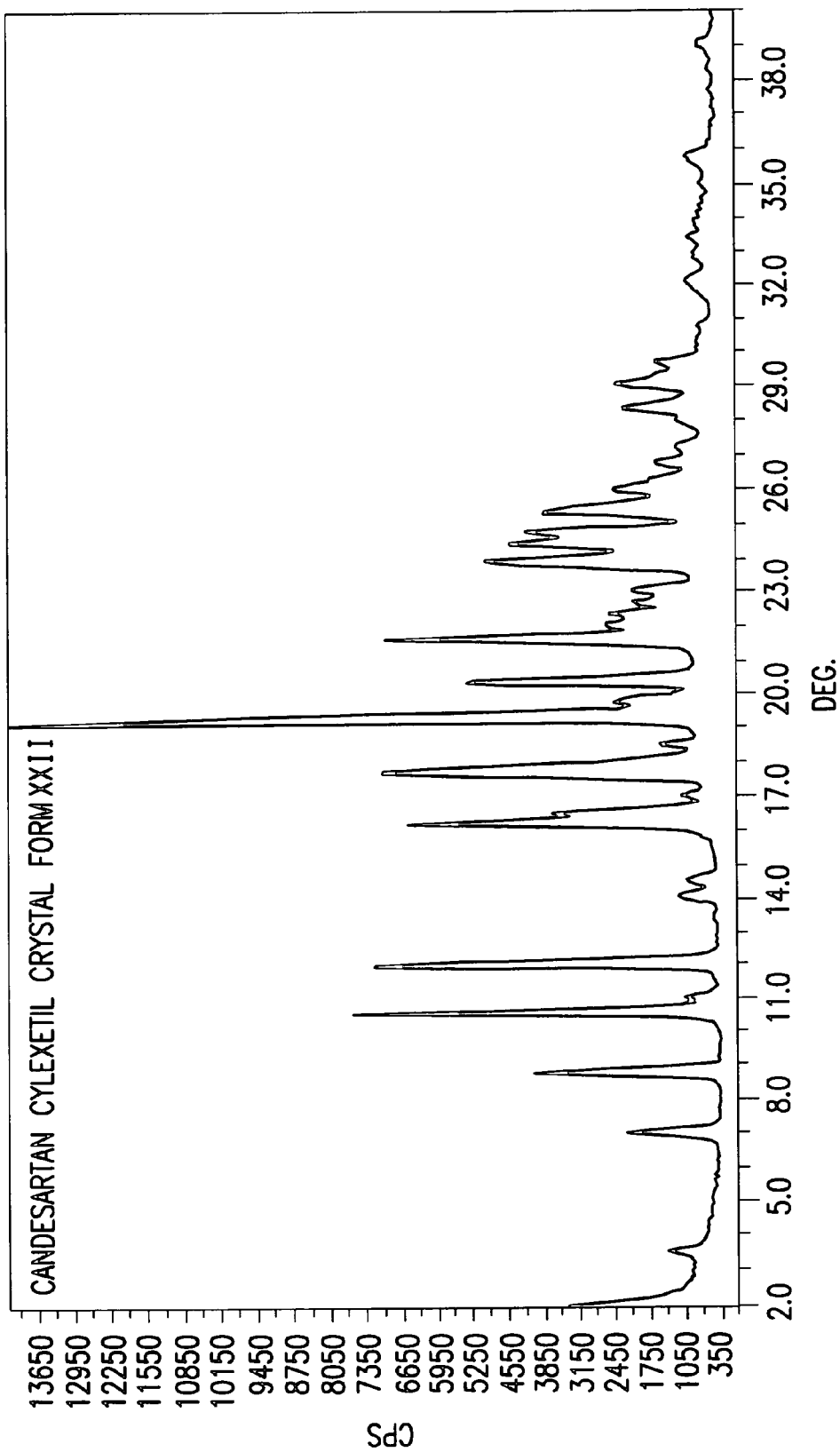
FIG. 22 illustrates the powder X-ray diffraction pattern for candesartan cilexetil Form XXII.
Figure 24A:
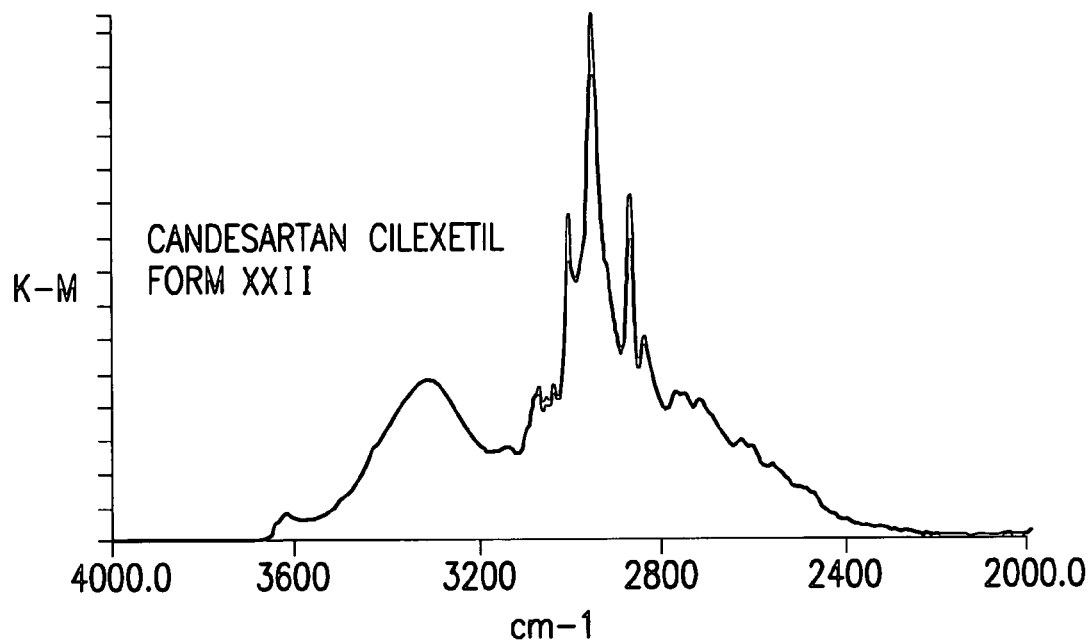
FIGS. 24a-c illustrate the expanded FTIR spectra for candesartan cilexetil Form XXII.
Figure 24B:
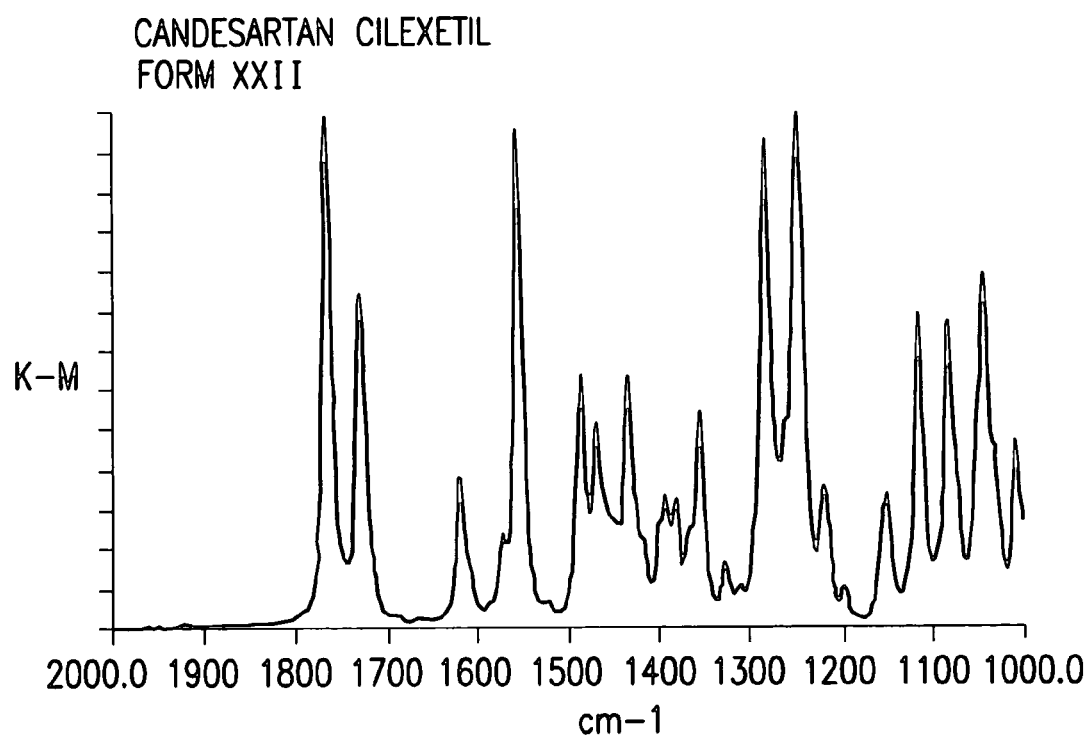
Figure 24C:
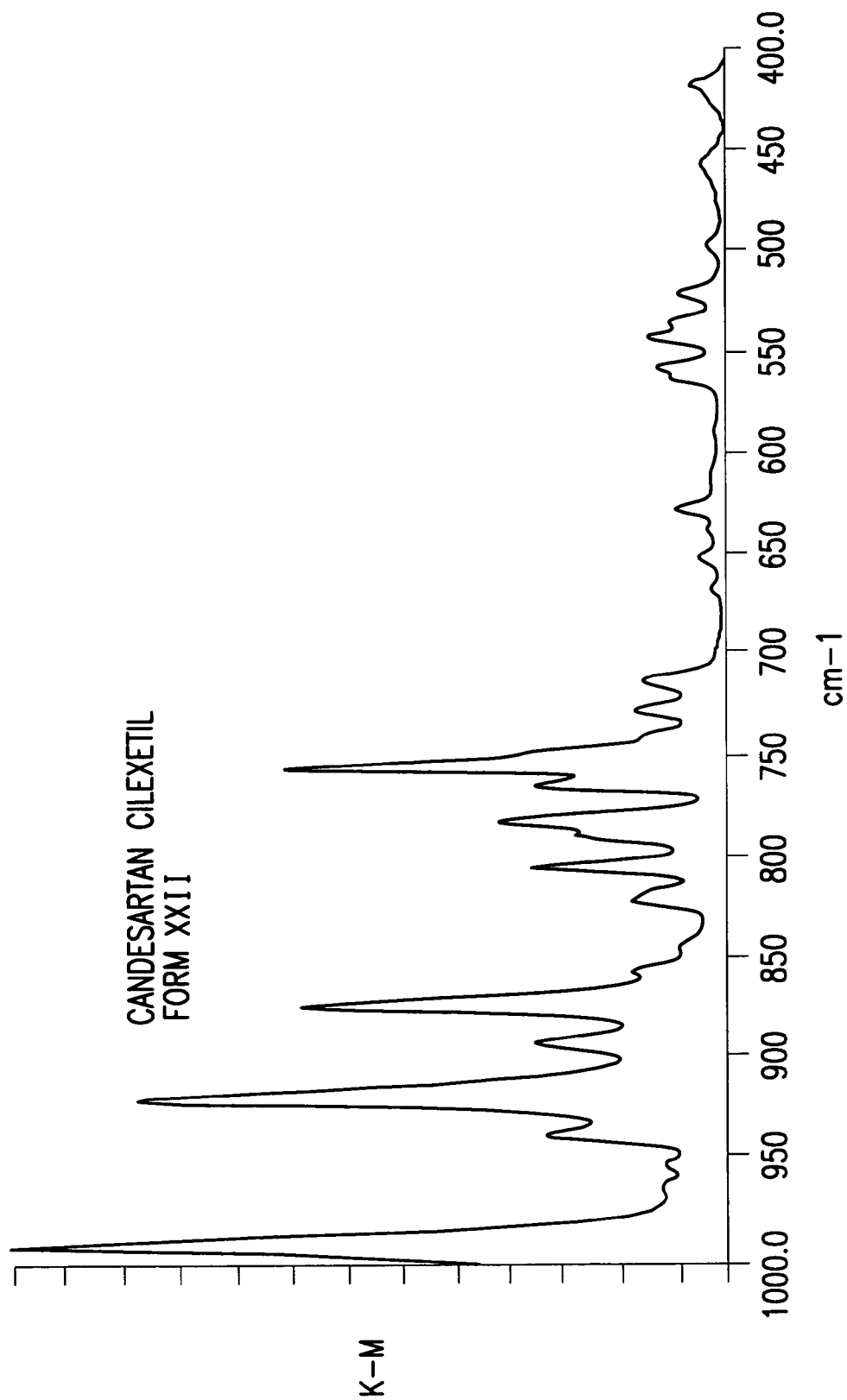

Another embodiment of the invention encompasses another candesartan cilexetil form, herein defined as Form XXII, which has about 0.5% moisture by weight, and the weight loss measured by TGA is about 4% to 20% by weight. Form XXII may be a solvate of methanol; with a L.O.D. by TGA of about 4% to about 20% by weight. Form XXII may be characterized by at least one of X-ray powder diffraction pattern or FTIR. Form XXII may be characterized by an X-ray powder diffraction pattern with peaks at about 10.6, 12.1, 17.8, 19.4, and 21.7 degrees two-theta, ±0.2 degrees two-theta. Form XXII may be further characterized by XRD peaks at about 7.1, 8.9, 16.3, 20.5, and 24.0 degrees two-theta, ±0.2 degrees two-theta. Form XXII X-ray powder diffraction spectrum is substantially depicted in FIG. 22. Form XXII may be characterized by an FTIR spectrum with characteristic absorption bands at about 1759, 1723, 1429, 1351, 1279, and 1082 cm$^{-1}$. The FTIR spectrum for Form XXII is substantially depicted in FIG. 23. An expanded FTIR of Form XXII is substantially depicted in FIGS. 24a-c.

Figure 25:
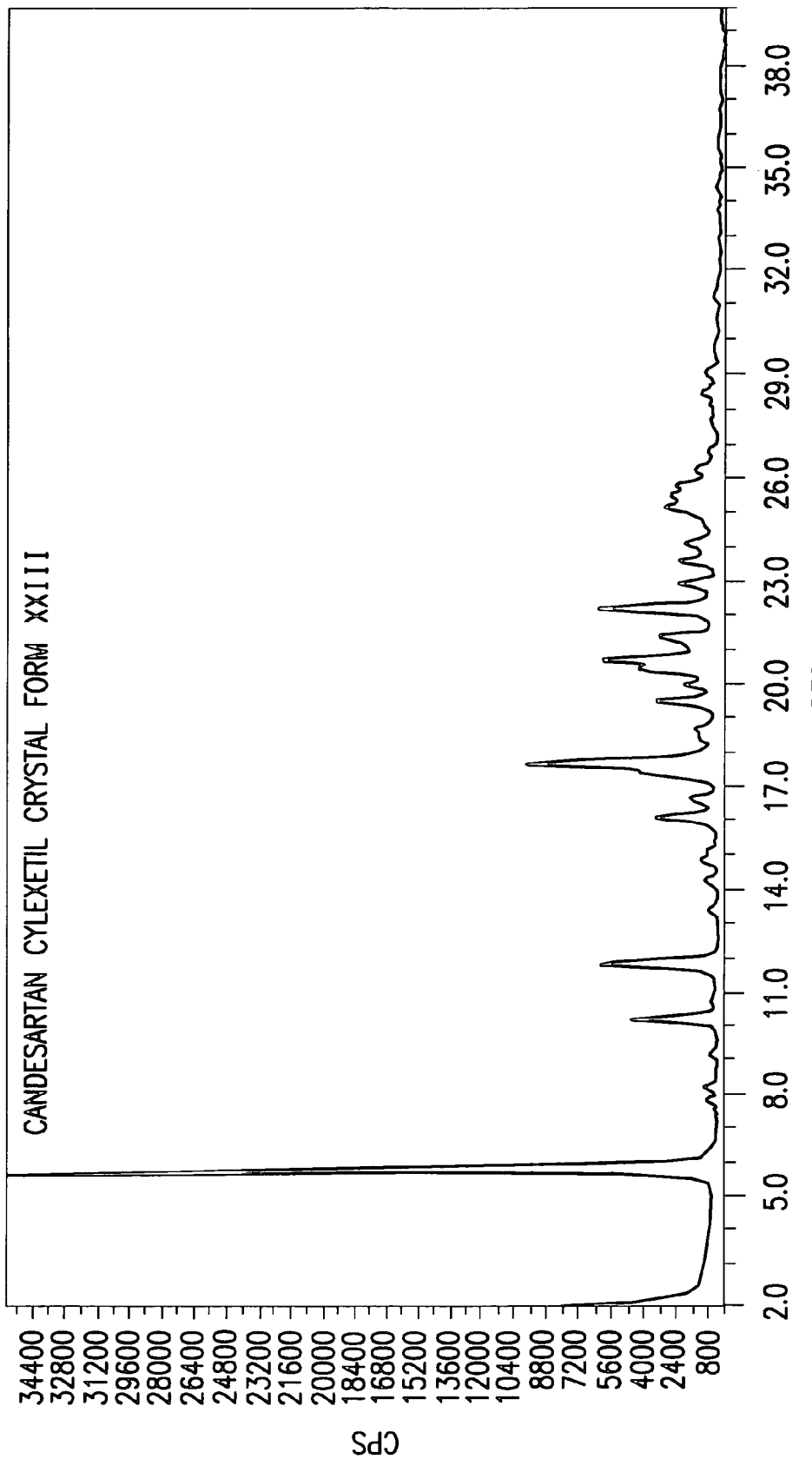
FIG. 25 illustrates the powder X-ray diffraction pattern for candesartan cilexetil Form XXIII.
Figure 26:
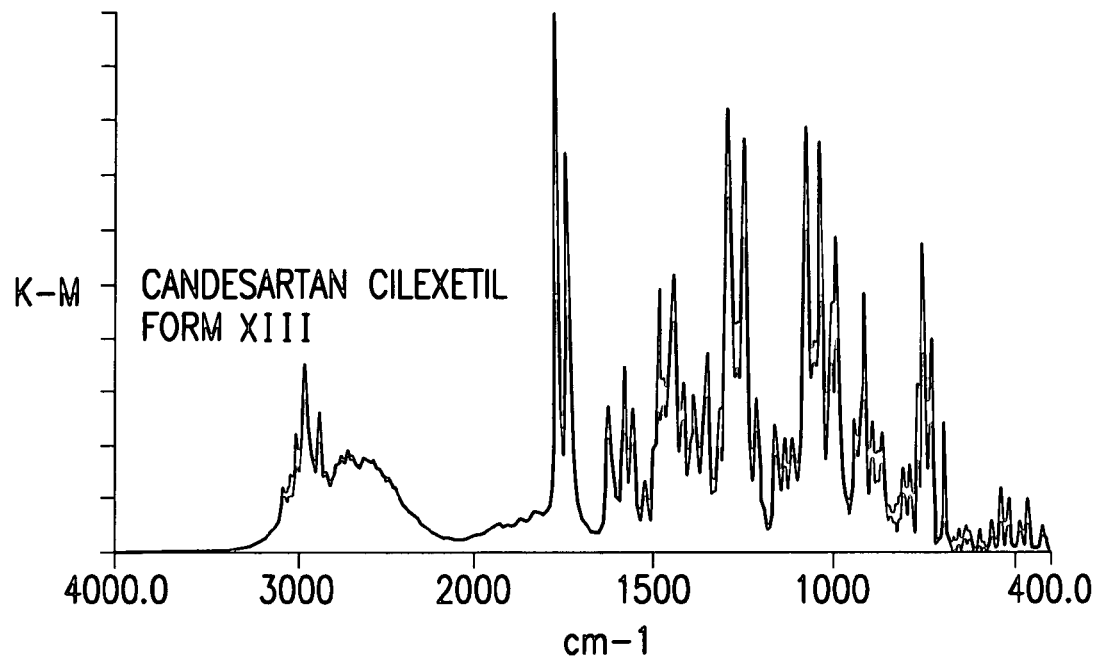
FIG. 26 illustrates the FTIR spectrum for candesartan cilexetil Form XXIII.
Figure 27A:
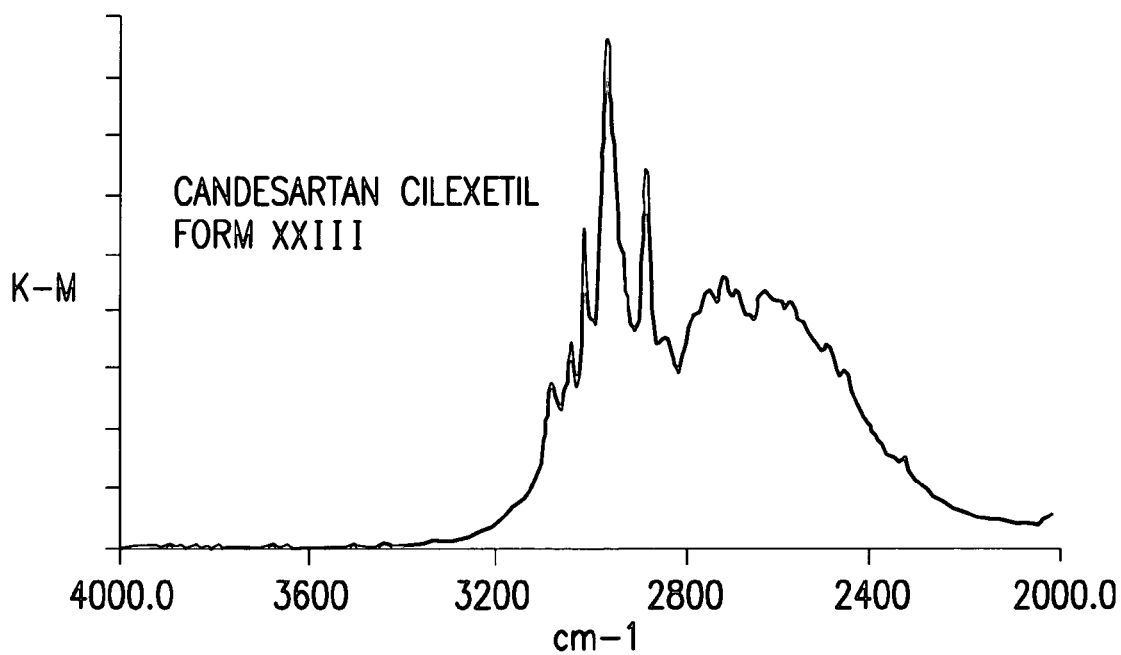
FIGS. 27a-c illustrate the expanded FTIR spectra for candesartan cilexetil Form XXIII.
Figure 27B:
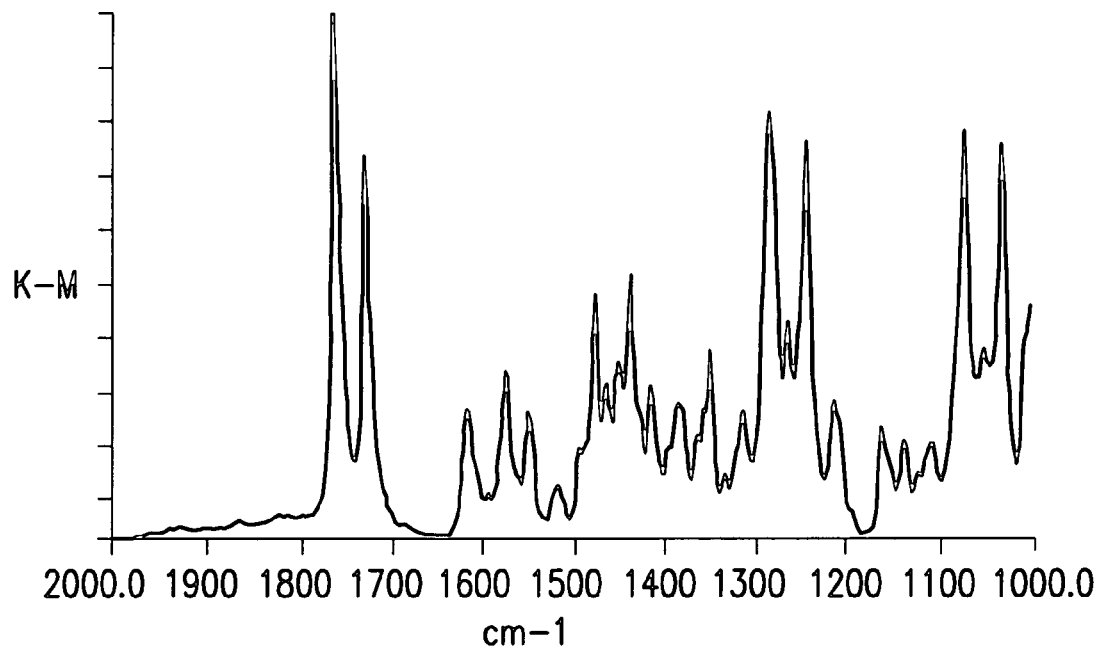
Figure 27C:
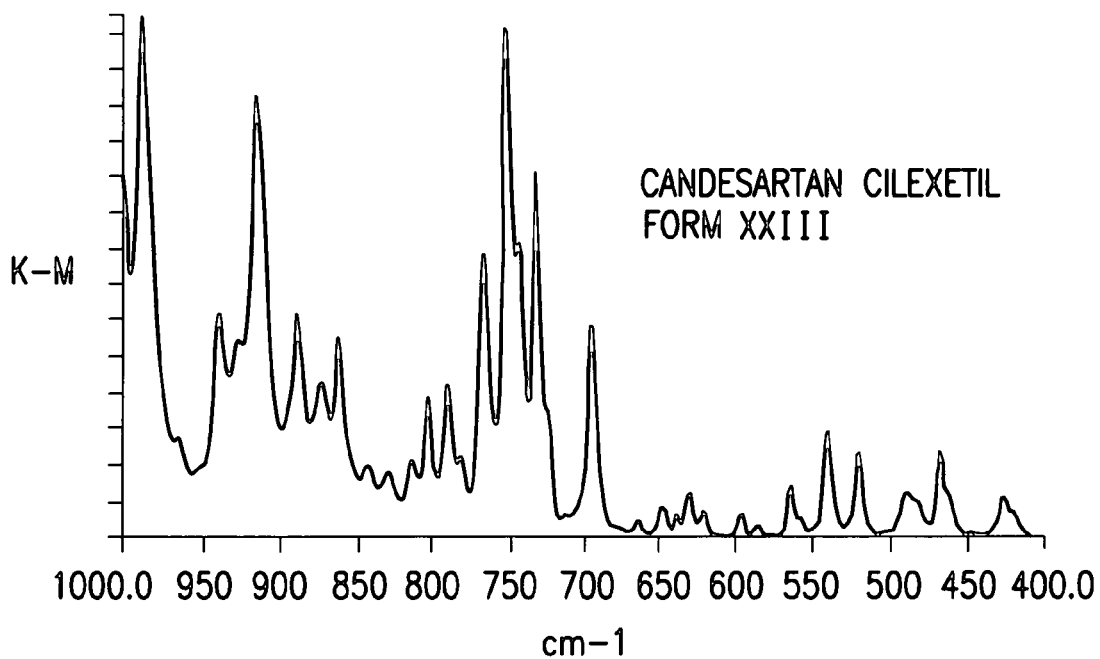

Yet another embodiment of the invention encompasses another candesartan cilexetil form, herein defined as Form XXIII, which has about 0.2% to about 0.4% moisture by weight, and the weight loss measured by TGA is about 5 to about 45% by weight. Form XXIII may be a toluene/methanol solvate; with a L.O.D. by TGA of about 5% to about 45% by weight. Form XXIII may be characterized by data from at least one of X-ray powder diffraction or FTIR. Form XXIII may be characterized by an X-Ray diffraction pattern having peaks at about 6.0, 12.0, 18.0, 21.0, and 22.4 degrees two-theta, ±0.2 degrees two-theta. Form XXIII may be further characterized by X-ray powder diffraction peaks at about 10.3, 16.3, 19.8, 21.6, and 23.1 degrees two-theta, ±0.2 degrees two-theta. The X-ray powder diffraction pattern for Form XXIII is substantially depicted in FIG. 25. Form XXIII may be characterized by an FTIR spectrum having absorption bands at about 1759, 1727, 1464, 1438, and 1071 cm$^{-1}$. The FTIR of Form XXIII is substantially depicted in FIG. 26. An expanded FTIR of Form XXIII is substantially depicted in FIGS. 27a-c.

The invention also encompasses polymorphically pure candesartan cilexetil Form III, IV, V, VI, VII, VIII, IX, X, XI, XIII, XIV, XIV-1, XV, XVI, XVII, XVIII, XIX, XX, XXI, XXII, or XXIII. The term "polymorphically pure" means that the candesartan cilexetil form contains other polymorphic forms in an amount of less than about 5% total weight. Preferably, the other polymorphic form is Form I.

The invention encompasses candesartan cilexetil polymorphs having an average particle size of no more than about 500 µm, preferably no more than about 300 µm, and more preferably no more than about 200 µm. Even more preferably, candesartan cilexetil polymorphs may have an average particle size of no more than about 100 µm, and most preferably, an average particle size of no more than about 50 µm.

The term "average particle size" refers to the average particle diameter, which may be measured by any of the methods commonly known in the art. The following methods, for example, may be used: sieves, sedimentation, electrozone sensing (coulter counter), microscopy, or Low Angle Laser Light Scattering (LALLS).

Candesartan cilexetil particles in sizes disclosed herein can be obtained by methods well known in the art. (See U.S. Pat. Nos. 4,151,273; 4,196,188; 4,302,446; 4,840,799; and 5,271,944.). One common technique to decrease particle size is by micronization. Micronization is a mechanical process that involves the application of force to a particle, thereby resulting in the break-up of the particle. Such force may be applied by collision of particles at high speeds. Micronization may be carried out, for example, by grinding or by an air-jet micronizer.

The invention also encompasses processes for preparing candesartan cilexetil forms of the invention.

In one embodiment of the invention, the processes for preparing candesartan cilexetil comprise heating a first form of candesartan cilexetil to obtain a second form of candesartan cilexetil. The process may further comprise heating at a reduced pressure. Preferably, the temperature is about 100° C., and if heating is conducted under reduced pressure, such as 20 mbar, the temperature is about 48° C. to about 50° C. Table 1 summarizes the transformations of the process.

TABLE 1

Transformation of Candesartan Cilexetil Forms

| Starting Form | Temp. (° C.) | Time | Pressure$^a$ | Product |
| --- | --- | --- | --- | --- |
| III, V, IX, XI, or XIV | 100 | 13 h | | amorphous |
| VII or VIII | 100 | 13 h | | IV |
| III | 48-50 | 30 min | 20 mbar | IV |
| III | 48-50 | aprox. 1 h$^b$ | 20 mbar | V |
| VI | 48-50 | $^b$ | 20 mbar | VII |
| X | 100 | 13 h | | IX |
| VI | 100 | 13 h | | XVI |
| XII or XV | 100 | 13 h | | XVI |

$^a$Unless otherwise indicated the reaction was run at atmospheric pressure.
$^b$Sufficient time to obtain a constant weight measurement of the candesartan cilexetil form.

Another process encompassed by the invention comprises dissolving candesartan cilexetil in a solvent to form a solution; allowing the solution to cool for a time to form a precipitate; and collecting the precipitate. Optionally, the process further comprises heating the solution. Optionally, the product may be dried at a specific temperature and at a reduced pressure. The solvent used in the dissolving step, the temperature to which the solvent is heated, the cooling temperature, and the time for the precipitate to form depend on the desired product. Examples 3, 4, 9, 15, 20, and 30 illustrate the process of the invention. The solvent includes, but is not limited to, at least one of acetone, acetonitrile, butanol, dichloromethane (DCM), dioxane, ethanol, ethyl acetate, isopropyl alcohol (IPA), methanol, or tetrahydrofuran (THF). The amount of the first solvent should be sufficient to substantially dissolve the candesartan cilexetil. The term "substantially dissolved" as used herein, means that about 80% of the candesartan cilexetil is dissolved. One of ordinary skill in the art with little or no experimentation can easily determine the sufficient amount of the solvent.

Another process encompassed by the invention comprises dissolving candesartan cilexetil in a first solvent and heating the mixture to form a solution; adding water to the solution, allowing the solution to cool for a time to form a precipitate; and collecting the precipitate. Water may be added to the solution dropwise, or the solution may be poured into water, wherein the water may be at room temperature (20° C. to 25° C.) or cooled in an ice bath. Optionally, the process may further comprise at least one step of cooling the solution for a second time, or drying the precipitate. The optional drying step may comprise drying the product at a specific temperature and at a reduced pressure. The solvent used in the dissolving step; the mode of water addition; the temperature to which the solvent is heated; the cooling temperature; and the time for the precipitate to form depend on the desired product. Examples 2, 5, 6, 19, 27, and 28 illustrate the process of the invention. The solvent includes, but is not limited to, at least one of acetone, acetonitrile, dimethylforamide (DMF), dioxane, ethanol, isopropyl alcohol (IPA), methanol, or tetrahydrofuran (THF).

Another process encompassed by the invention comprises dissolving candesartan cilexetil in a first solvent and heating the mixture to form a solution; adding a second solvent to the solution, allowing the solution to cool for a time to form a precipitate; and collecting the precipitate. The second solvent may be added to the solution dropwise. Optionally, the process may further comprise at least one step of heating the solution; cooling the solution for a second time; or drying the precipitate. The optional drying step may comprise drying the product at a specific temperature and at a reduced pressure. The solvent used in the dissolving step; the mode of second solvent addition; the temperature to which the solvent is heated; the cooling temperature; and the time for the precipitate to form depend on the desired product. Examples 12, 21-24, and 29 illustrate the process of the invention. The first solvent includes, but is not limited to, at least one of chloroform, or dichloromethane (DCM). The second solvent includes, but is not limited to, acetonitrile, butanol, cyclohexane, isoamyl acetate, heptane, tert-butyl methyl ether (TBME), or toluene.

Another process encompassed by the invention comprises dissolving candesartan cilexetil in a first solvent to form a solution; adding a second solvent to the solution, allowing the solution to cool to a first cooling temperature; adding a third solvent; cooling the solution to a second cooling temperature for a time to form a precipitate; and collecting the precipitate. The second solvent and third solvent may be added to the solution dropwise. Optionally, the process may further comprise drying the precipitate. The optional drying step may comprise drying the product at a specific temperature and at a reduced pressure. The solvents used in the dissolving step and second and third addition steps; the mode of second or third solvent addition; the first or second cooling temperature; and the time for the precipitate to form depend on the desired product. Example 17 illustrates the process of the invention.

Preferably, the second solvent is poured into the solution before allowing the solution to precipitate. The second or third solvent includes, but is not limited to, at least one of acetonitrile, tert-butyl methyl ether (TBME), or toluene.

Another process encompassed by the invention comprises triturating candesartan cilexetil in a solvent until a precipitate forms and collecting the precipitate. Optionally, the process may further comprise at least one step of heating the solution; cooling the solution; or drying the precipitate. The optional drying step may comprise drying the product at a specific temperature and at a reduced pressure. The solvent used in the triturating step; the temperature to which the solvent is heated; the cooling temperature; and the time for the precipitate to form depend on the desired product. Examples 8 and 14 illustrate the process of the invention.

Allowing the solution to precipitate can be performed continuously or stepwise.

For example, the cooling step can be performed continuously at about 20° C. to 27° C. The cooling step can also be performed stepwise, first at about 25° C. to 27° C. and then at about 0° C. to 5° C. Another example of stepwise cooling is allowing the solution to reach a first temperature of about 0° C. to 5° C. and then allowing the solution to reach a temperature of about 25° C. to 27° C. Preferably, the cooling step comprises allowing the solution to cool with stirring.

The process may further comprise drying the precipitate. In one embodiment of the invention, drying comprises drying the precipitate on the filter used for collecting the precipitate. In another embodiment of the invention, drying the precipitate can be performed at reduced pressure, 20 mbar for example, at about 40° C. to 50° C. to a constant weight. Drying the precipitate can be performed continuously or stepwise.

The following are processes for preparing each candesartan cilexetil form according to the invention.

One embodiment of the invention is directed towards a process for preparing candesartan cilexetil Form I, the process comprising dissolving candesartan cilexetil in a solvent to form a solution; heating the solution at a temperature of at least about 45° C.;

and precipitating candesartan cilexetil Form I. The solvent may include a $C_1$-$C_4$ alcohol, a $C_3$-$C_8$ ester, acetonitrile, or mixtures thereof. Preferably, the alcohol is at least one of butanol, methanol, isopropanol, or ethanol. Preferably, the ester is ethyl acetate.

The amount of solvent, including all other solvents disclosed herein, should be sufficient to substantially dissolve the candesartan cilexetil. The term "substantially dissolved" means that about 80% of the candesartan cilexetil is dissolved. One of ordinary skill in the art with little or no experimentation can easily determine the sufficient amount of the solvent.

The solution may be heated at a temperature of from about 45° C. to about 70° C. Preferably, the solution is heated at a temperature of from about 50° C. to about 64° C. Also preferably, when the solvent is methanol, the solution is heated at reflux. The solution is heated in order to facilitate the dissolution of candesartan cilexetil.

The solution may be cooled, preferably at room temperature, to form a precipitate. Since the solution was previously heated in order to completely dissolve candesartan cilexetil, no extreme cooling is necessary for crystallization to occur, and there is no decrease in the yield caused by easy dissolution. When a material dissolves easily, cooling to lower temperature is necessary in order to properly crystallize the material and increase the yield.

The recovered candesartan cilexetil Form I may optionally be dried at a temperature of from about 35° C. to about 60° C., preferably from about 40° C. to about 50° C. The candesartan cilexetil Form I may be dried under reduced pressure such as a pressure of less than about 50 mbar, preferably under a pressure of from about 20 mbar to about 30 mbar.

Another process for preparing candesartan cilexetil Form I comprises dissolving candesartan cilexetil in a solvent to form a solution; combining water with the solution to form a mixture; and precipitating from the mixture candesartan cilexetil Form I, wherein the solvent is at least one of a $C_1$-$C_4$ alcohol, a ketone, an alkyl amide, or acetonitrile. Preferably, the alcohol is at least one of methanol, isopropanol, or ethanol. Preferably, the ketone is acetone. Preferably, the alkyl amide is dimethylformamide.

The solution may be kept around room temperature, or it may be heated. The solution is preferably heated at a temperature of from about 45° C. to about 80° C., and more preferably at a temperature of from about 50° C. to about 75° C.

Preferably, the water is added dropwise to the solution. Where the solvent is acetone, the solution is preferably poured into water. Water in this process is used as an antisolvent.

The recovered candesartan cilexetil Form I may optionally be dried at a temperature of from about 35° C. to about 60° C., preferably from about 40° C. to about 50° C. The candesartan cilexetil Form I may be dried under reduced pressure such as a pressure of less than about 50 mbar, or a pressure about 30 mbar.

Another process for preparing candesartan cilexetil Form I comprises heating candesartan cilexetil Form VII or Form VIII. The Form VII or Form VIII may be heated at a temperature of from about 90° C. to about 120° C., preferably at about 100° C. The Form VII or Form VIII may be heated for at least about 10 hours, preferably for about 13 hours.

Another process for preparing candesartan cilexetil Form I comprises dissolving at least one of candesartan cilexetil Form XIV, XIV-1, XXII or XXIII in a $C_1$-$C_4$ alcohol to form a solution and precipitating from the solution candesartan cilexetil Form I. Preferably, the alcohol is ethanol.

The solution may optionally be cooled. If cooled, the solution is preferably cooled at a temperature of from about 0° C. to about 10° C., more preferably from about 4° C. to about 8° C.

The recovered candesartan cilexetil Form I may optionally be dried at a temperature of from about 40° C. to about 60° C., preferably at about 50° C. The candesartan cilexetil Form I may be dried under reduced pressure such as a pressure of less than about 50 mbar, preferably under a pressure of about 10 mbar.

Another process for preparing candesartan cilexetil Form I comprises preparing a slurry of candesartan cilexetil Form XIV, XIV-I, XXII, or XXIII in absolute ethanol; and isolating candesartan cilexetil Form I from the slurry.

Preferably, the mixture is cooled at a temperature of from about −20° C. to about 20° C., more preferably from about −10° C. to about 10° C.

One embodiment of the invention is directed towards a process for preparing candesartan cilexetil Form II, the process comprising triturating candesartan cilexetil in water until a precipitate forms, and collecting from the precipitate Form II. Preferably, the triturated candesartan cilexetil is Form V.

Trituration may be carried out at room temperature. The precipitate may be collected by filtration.

Another embodiment of the invention is directed towards a process for preparing candesartan cilexetil Form III, the process comprising dissolving candesartan cilexetil in a solvent to form a solution; heating the solution at a temperature of at least about 45° C.; and precipitating from the solution candesartan cilexetil Form III, wherein the solvent is at least one of a ketone or tetrahydrofuran. Preferably, the ketone is acetone.

The solution may optionally be heated. If heated, the solution is preferably heated at a temperature of from about 40° C. to about 60° C., more preferably from about 55° C. to about 56° C.

Another process for preparing candesartan cilexetil Form III comprises dissolving candesartan cilexetil in tetrahydrofuran to form a solution; combining water with the solution to form a precipitate; isolating the precipitate; and drying the precipitate to obtain candesartan cilexetil Form III.

The solution may optionally be heated before water is combined. If heated, the solution is preferably heated at a temperature of from about 40° C. to about 60° C., more preferably from about 55° C. to about 56° C.

After the addition of water, the mixture may optionally be cooled. If cooled, the mixture is preferably cooled at a temperature of from about 0° C. to about 10° C., more preferably from about 4° C. to about 8° C.

The precipitate may be dried at a temperature of from about 40° C. to about 60° C., preferably from about 50° C. to about 52° C. Preferably, the precipitate is dried under a pressure of less than about 50 mbar, more preferably under a pressure of about 10 mbar.

Another embodiment of the invention is directed towards a process for preparing candesartan cilexetil Form IV, the process comprising drying candesartan cilexetil Form III to a weight loss of about 8.9%.

Preferably, Form III is dried at a temperature of from about 40° C. to about 60° C., more preferably from about 48° C. to about 50° C. Preferably, Form III is dried under a pressure of less than about 50 mbar, more preferably under a pressure of about 20 mbar.

Another embodiment of the invention is directed towards a process for preparing candesartan cilexetil Form V, the process comprising drying candesartan cilexetil Form III to a weight loss of about 11%.

Preferably, Form III is dried at a temperature of from about 40° C. to about 60° C., more preferably from about 48° C. to about 50° C. Preferably, Form III is dried under a pressure of less than about 50 mbar, more preferably under a pressure of about 20 mbar.

Another process for preparing candesartan cilexetil Form VI comprises dissolving candesartan cilexetil in dichloromethane to form a solution; combining heptane with the solution to form a mixture; and precipitating from the mixture candesartan cilexetil Form VI.

The mixture may optionally be cooled after the addition of heptane. If cooled, the mixture is preferably cooled at a temperature of from about −5° C. to about 15° C., more preferably from about 0° C. to about 5° C.

Another embodiment of the invention is directed towards a process for preparing candesartan cilexetil Form VII, the process comprising drying candesartan cilexetil Form VI.

Preferably, Form VI is dried to a constant weight. The term "constant weight" means that the weight of the candesartan cilexetil form will not fluctuate for more than about 3% of the total weight during the drying process. Preferably, Form VI is dried at a temperature of from about 40° C. to about 60° C., more preferably from about 48° C. to about 50° C. Preferably, Form VI is dried under a pressure of less than about 50 mbar, more preferably under a pressure of about 20 mbar.

Another process for preparing candesartan cilexetil Form VII comprises triturating candesartan cilexetil in toluene until a precipitate forms and collecting the precipitate. Trituration may be carried out at an elevated temperature, preferably at from about 40° C. to about 60° C., more preferably at about 50° C. Preferably, the candesartan cilexetil is triturated for about 1 hour at a temperature of about 50° C. Preferably, the triturated candesartan cilexetil is Form I.

Also preferably, the candesartan cilexetil is triturated for about 24 hours at a temperature of from about 50° C. to about 70° C., more preferably from about 60° C. to about 62° C.

The precipitate may be collected by filtration. The precipitate may be dried at a temperature of from about 40° C. to about 60° C., preferably from about 50° C. to about 52° C. Preferably, the precipitate is dried under a pressure of less than about 50 mbar, more preferably under a pressure of about 30 mbar.

Another process for preparing candesartan cilexetil Form VII comprises dissolving candesartan cilexetil in dichloromethane to form a solution; combining butanol with the solution to form a mixture; and precipitating from the mixture candesartan cilexetil Form VII.

The mixture may optionally be cooled after the addition of butanol. If cooled, the mixture is preferably cooled at a temperature of from about −5° C. to about −20° C., more preferably from about −11° C. to about −14° C.

Another embodiment of the invention is directed towards a process for preparing candesartan cilexetil Form VIII, the process comprising dissolving candesartan cilexetil in methyl ethyl ketone solvent to form a solution; heating the solution at a temperature of at least about 45° C.; and precipitating from the solution candesartan cilexetil Form VIII.

The solution may be heated at a temperature of from about 50° C. to about 70° C. Preferably, the solution is heated at a temperature of from about 60° C. to about 62° C.

The solution may optionally be cooled to precipitate candesartan cilexetil Form VIII. If cooled, the solution is preferably cooled to room temperature, more preferably followed by cooling at a temperature of from about 0° C. to about 10° C., most preferably from about 4° C. to about 6° C.

Another embodiment of the invention is directed towards a process for preparing candesartan cilexetil Form IX, the process comprising dissolving candesartan cilexetil in dichloromethane to form a solution; combining a first portion of a solvent with the solution to form a first mixture; cooling the first mixture at a temperature of less than about 10° C.; combining a second portion of the solvent with the first mixture to form a second mixture; and precipitating from the second mixture candesartan cilexetil Form IX, wherein the solvent is at least one of acetonitrile, tert butyl methyl ether, or toluene.

Preferably, the first portion of the solvent is added dropwise.

Preferably, before the addition of the second portion of the solvent, the first mixture is cooled at a temperature of from about −10° C. to about 10° C., more preferably, the first mixture is cooled to about 0° C. on an ice bath.

The second mixture may optionally be cooled after the addition of a second portion of the solvent, preferably at a temperature of from about −25° C. to about 5° C., more preferably from about −15° C. to about 0° C.

The precipitate may optionally be dried at a temperature of from about 35° C. to about 60° C., preferably from about 40° C. to about 50° C. Preferably, the precipitate is dried under a pressure of less than about 50 mbar, more preferably under a pressure of about 30 mbar.

Another process for preparing candesartan cilexetil Form IX comprises dissolving candesartan cilexetil in chloroform to form a solution; combining toluene with the solution to form a mixture; and precipitating from the mixture candesartan cilexetil Form IX.

Preferably, the toluene is added dropwise. The mixture may optionally be cooled after the addition of toluene, preferably at a temperature of from about −25° C. to about 5° C., more preferably from about −15° C. to about 0° C.

The precipitate may optionally be dried at a temperature of from about 35° C. to about 60° C., preferably from about 40° C. to about 45° C. Preferably, the precipitate is dried under a pressure of less than about 50 mbar, more preferably under a pressure of about 30 mbar.

Another process for preparing candesartan cilexetil Form IX comprises heating candesartan cilexetil Form X. Form X may be heated at a temperature of from about 90° C. to about 120° C., preferably at about 100° C. Form X may be heated for at least about 10 hours, preferably for about 13 hours.

Another embodiment of the invention is directed towards a process for preparing candesartan cilexetil Form X, the process comprising dissolving candesartan cilexetil in dioxane to form a solution; combining water with the solution to form a mixture; and precipitating from the mixture candesartan cilexetil Form X.

Preferably, the water is added dropwise.

The solution may optionally be heated before water is combined. If heated, the solution is preferably heated at a temperature of from about 40° C. to about 60° C., more preferably at about 50° C. The mixture may optionally be cooled after the addition of water, preferably on an ice bath.

The precipitate may be dried at a temperature of from about 35° C. to about 50° C., preferably from about 40° C. to about 45° C. The precipitate may be dried under a pressure of less than about 50 mbar, preferably under a pressure of about 30 mbar.

Another process for preparing candesartan cilexetil Form X comprises dissolving candesartan cilexetil in dioxane to form a solution and precipitating from the solution candesartan cilexetil Form X.

Another embodiment of the invention is directed towards a process for preparing candesartan cilexetil Form XI, the process comprising dissolving candesartan cilexetil in chloroform to form a solution; combining a solvent with the solution to form a mixture; and precipitating from the mixture candesartan cilexetil Form XI, wherein the solvent is at least one of heptane, cyclohexane, or tert butyl methly ether.

Preferably, the solvent is added dropwise. The mixture may optionally be cooled after the addition of the solvent, preferably at a temperature of from about −10° C. to about 10° C., more preferably at about 0° C.

The precipitate may optionally be dried at a temperature of from about 35° C. to about 60° C., preferably from about 40° C. to about 50° C. Preferably, the precipitate is dried under a pressure of less than about 50 mbar, more preferably under a pressure of about 30 mbar.

Another process for preparing candesartan cilexetil Form XI comprises dissolving candesartan cilexetil in dichloromethane to form a solution; combining cyclohexane with the solution to form a mixture; and precipitating from the mixture candesartan cilexetil Form XI.

Preferably, the cyclohexane is added dropwise. The mixture may optionally be cooled after the addition of cyclohexane, preferably at a temperature of from about −10° C. to about 10° C., more preferably at about 0° C.

The precipitate may optionally be dried at a temperature of from about 40° C. to about 60° C., preferably at about 50° C.

The precipitate may be dried under a pressure of less than about 50 mbar, preferably under a pressure of about 30 mbar.

Another embodiment of the invention is directed towards a process for preparing candesartan cilexetil Form XIII, the process comprising dissolving candesartan cilexetil in dichloromethane to form a solution; combining isoamyl acetate with the solution to form a mixture; and precipitating from the mixture candesartan cilexetil Form XIII.

Preferably, the isoamyl acetate is added dropwise. The mixture may optionally be cooled after the addition of isoamyl acetate, and preferably at a temperature of about 0° C.

The precipitate may optionally be dried at a temperature of from about 40° C. to about 60° C., preferably at about 50° C. Preferably, the precipitate is dried under a pressure of less than about 50 mbar, more preferably under a pressure of about 30 mbar.

Another embodiment of the invention is directed towards a process for preparing candesartan cilexetil Form XIV, the process comprising dissolving candesartan cilexetil in dichloromethane to form a solution; combining toluene with the solution to form a mixture; and precipitating from the mixture candesartan cilexetil Form XIV.

Preferably, the toluene is added dropwise. Optionally, the toluene may be added in two portions, wherein the mixture is cooled, preferably in an ice bath, after the addition of a first portion of toluene, and followed by the addition of a second portion of toluene. The mixture may optionally be cooled again to precipitate Form XIV, preferably at a temperature of from about <20° C. to about 0° C., more preferably at about −10° C. Preferably, the precipitate is dried by filtration.

Candesartan cilexetil Form XIV may be converted to candesartan cilexetil Form I by dissolving Form XIV in a $C_1$-$C_4$ alcohol to form a solution and precipitating from the solution candesartan cilexetil Form I.

Candesartan cilexetil Form XIV can also be converted to candesartan cilexetil Form I by preparing a slurry of candesartan cilexetil Form XIV in absolute ethanol; and isolating candesartan cilexetil Form I from the slurry.

Another embodiment of the invention is directed towards a process for preparing candesartan cilexetil Form XIV-1, the process comprising preparing a solution of trityl candesartan cilexetil in a first portion of toluene or dichloromethane, and a first $C_1$-$C_4$ alcohol, acid, or both to deprotect the trityl candesartan cilexetil and obtain candesartan cilexetil; concentrating the solution into a residue; combining a second portion of toluene or dichloromethane, and a second $C_1$-$C_4$ alcohol with the residue to form a mixture; and precipitating from the mixture candesartan cilexetil Form XIV-1.

Concentration may be by evaporation. Evaporation may be carried out at a temperature of from about 50° C. to about 70° C., more preferably at about 60° C. Evaporation may be carried out under a pressure of less than about 50 mbar, more preferably under a pressure of about 30 mbar. The residue may be in the form of a viscous oil.

Optionally, water may be added to the solution of trityl candesartan cilexetil. Preferably, the toluene or dichloromethane used to prepare the trityl candesartan cilexetil solution is toluene. Preferably, the first $C_1$-$C_4$ alcohol is methanol. Preferably, the second $C_1$-$C_4$ alcohol is methanol. Preferably, the first and second $C_1$-$C_4$ alcohol are the same, more preferably methanol. Preferably, the acid is selected from the group consisting of formic acid, trifluoroacetic acid, methane sulfonic acid, a mixture of hydrobromic acid with acetic acid, and a mixture of hydrochloric acid and sulfuric acid. More preferably, the acid is formic acid.

Preferably, the reaction time is at least about 10 hours. Reaction time may easily be determined by monitoring the reaction progress and/or completion by HPLC.

Preferably, after dissolving the residue, candesartan cilexetil Form XIV-1 is precipitated by cooling the mixture at a temperature of from about 0° C. to about 10° C., preferably at a temperature of from about 4° C. to about 8° C.

Candesartan cilexetil Form XIV-1 may be converted to candesartan cilexetil Form I by dissolving Form XIV-1 in a $C_1$-$C_4$ alcohol to form a solution and precipitating from the solution candesartan cilexetil Form I.

Candesartan cilexetil Form XIV-1 can also be converted to candesartan cilexetil Form I by preparing a slurry of candesartan cilexetil Form XIV-1 in absolute ethanol; and isolating candesartan cilexetil Form I from the slurry.

Another embodiment of the invention is directed towards a process for preparing candesartan cilexetil Form XV, the process comprising dissolving candesartan cilexetil in chloroform to form a solution; combining acetonitrile with the solution to form a precipitate; isolating the precipitate; and drying the precipitate to recover candesartan cilexetil Form XV.

Preferably, the acetonitrile is added dropwise. The mixture may optionally be cooled after the addition of acetonitrile, preferably in an ice bath until a precipitate forms.

Preferably, the precipitate is dried at a temperature of from about 40° C. to about 60° C., more preferably at about 45° C. Preferably, the precipitate is dried under a pressure of less than about 50 mbar, more preferably under a pressure of about 30 mbar.

Another embodiment of the invention is directed towards a process for preparing candesartan cilexetil Form XVI, the process comprising heating candesartan cilexetil Form VI. Form VI may be heated at a temperature of from about 90° C. to about 120° C., preferably at about 100° C. Form VI may be heated for at least about 10 hours, preferably for about 13 hours.

Another embodiment of the invention is directed towards a process for preparing candesartan cilexetil Form XVII, the process comprising heating candesartan cilexetil Form XIII or Form XV. The Form XIII or Form XV may be heated at a temperature of from about 90° C. to about 120° C., preferably at about 100° C. The Form XIII or Form XV may be heated for at least about 10 hours, preferably for about 13 hours.

Another embodiment of the invention is directed towards a process for preparing candesartan cilexetil Form XVIII, the process comprising dissolving candesartan cilexetil in tetrahydrofuran to form a solution; pouring the solution into water to form a mixture; and precipitating from the mixture candesartan cilexetil Form XVIII.

The solution may optionally be heated before being poured into water. If heated, the solution is preferably heated at a temperature of from about 50° C. to about 70° C., more preferably from about 60° C. to about 62° C.

The water may be at a temperature of from about −10° C. to about 10° C., more preferably at about 5° C. The mixture may optionally be cooled after the addition of water, preferably at a temperature of from about −5° C. to about 10° C., more preferably from about 5° C. to about 7° C.

Another embodiment of the invention is directed towards a process for preparing candesartan cilexetil Form XIX, the process comprising dissolving candesartan cilexetil in acetonitrile to form a solution; pouring the solution into water to form a mixture; and precipitating from the mixture candesartan cilexetil Form XIX.

The solution may optionally be heated before being poured into water. If heated, the solution is preferably heated at a temperature of from about 50° C. to about 70° C., more preferably about 60° C. to about 64° C.

The water may be at a temperature of from about −10° C. to about 10° C., more preferably from about 0° C. about 5° C. The mixture may optionally be cooled after the addition of water, preferably at a temperature of from about −10° C. to about 10° C., more preferably from about 0° C. to about 5° C.

Another embodiment of the invention is directed towards a process for preparing candesartan cilexetil Form XX, the process comprising dissolving candesartan cilexetil in chloroform to form a solution; combining acetonitrile with the solution to form a mixture; and precipitating from the mixture candesartan cilexetil Form XX.

Preferably, the acetonitrile is added dropwise. The mixture may optionally be cooled after the addition of acetonitrile, preferably in an ice bath until a precipitate forms. Preferably, the precipitate is collected by filtration.

Another embodiment of the invention is directed towards a process for preparing candesartan cilexetil Form XXI, the process comprising dissolving candesartan cilexetil in tetrahydrofuran to form a solution; and precipitating from the solution candesartan cilexetil Form XXI.

Preferably, the candesartan cilexetil Form XXI is precipitated after at least about 7 days, more preferably after about 3 weeks.

Another embodiment of the invention is directed towards a process for preparing candesartan cilexetil Form XXII, the process comprising dissolving crude candesartan in a $C_1$-$C_4$ alcohol at a temperature of at least about 45° C. to form a solution; and precipitating candesartan cilexetil Form XXII. Preferably, the alcohol is methanol.

Preferably, the solution is heated at a temperature of from about 50° C. to about 60° C., preferably at a temperature of about 50° C.

The candesartan cilexetil Form XXII may be precipitated by cooling the solution, preferably at a temperature of from about −10° C. to about 20° C., more preferably at a temperature of about −5° C. to about 5° C., for about 6 hours to about 16 hours, preferably for about 16 hours, until a precipitate forms.

The precipitate may optionally be dried at a temperature of from about 40° C. to about 60° C., preferably at about 50° C. Preferably, the precipitate is dried under a pressure of less than about 50 mbar, more preferably under a pressure of about 10 mbar.

Candesartan cilexetil Form XXII may be converted to candesartan cilexetil Form I by dissolving Form XXII in a $C_1$-$C_4$ alcohol to form a solution and precipitating from the solution candesartan cilexetil Form I.

Candesartan cilexetil Form XXII can also be converted to candesartan cilexetil Form I by preparing a slurry of candesartan cilexetil Form XXII in absolute ethanol; and isolating candesartan cilexetil Form I from the slurry.

Another embodiment of the invention is directed towards a process for preparing candesartan cilexetil Form XXIII, the process comprising preparing a solution of trityl candesartan cilexetil in a first portion of toluene or dichloromethane, a first $C_1$-$C_4$ alcohol, and water to deprotect the trityl candesartan cilexetil and obtain candesartan cilexetil; concentrating the solution into a residue; combining a second portion of toluene or dichloromethane, and a second $C_1$-$C_4$ alcohol with the residue to form a mixture; and precipitating from the mixture candesartan cilexetil Form XXIII.

Preferably, the toluene or dichloromethane used to prepare the trityl candesartan cilexetil solution is toluene. Preferably, the first $C_1$-$C_4$ alcohol is methanol. Preferably, the second $C_1$-$C_4$ alcohol is methanol. Preferably, the first and second $C_1$-$C_4$ alcohol are the same, more preferably methanol. Preferably, the solution of trityl candesartan cilexetil is maintained at a reflux temperature for about 2.5 to about 6 hours, preferably for about 3 hours.

Concentration may be by evaporation. Evaporation may be carried out at a temperature of from about 30° C. to about 60° C., more preferably at about 45° C. Evaporation may be carried out under a pressure of less than about 100 mbar, more preferably under a pressure of about 90 mbar. The residue may be in the form a viscous oil.

Preferably, the residue is combined with the second portion of dichloromethane or toluene and the second $C_1$-$C_4$ alcohol at a temperature of from about 45° C. to about 55° C., more preferably at a temperature of about 50° C. The resulting mixture may optionally be cooled at a temperature of from about 35° C. to about 45° C.; and further cooled at a temperature of from about −15° C. to about 15° C., preferably at from about −5° C. to about 5° C. for about 1-12 hours, until a precipitate is obtained. Optionally, the mixture may be seeded with candesartan cilexetil Form XXII to obtain candesartan cilexetil Form XXIII.

The precipitate may optionally be dried at a temperature of from about 40° C. to about 60° C., preferably at about 50° C. The precipitate may be dried under a pressure of less than about 50 mbar, preferably under a pressure of about 10 mbar.

Candesartan cilexetil Form XXIII may be converted to candesartan cilexetil Form I by dissolving Form XXIII in a $C_1$-$C_4$ alcohol to form a solution and precipitating from the solution candesartan cilexetil Form I.

Candesartan cilexetil Form XXIII can also be converted to candesartan cilexetil Form I by preparing a slurry of candesartan cilexetil Form XXIII in absolute ethanol; and isolating candesartan cilexetil Form I from the slurry.

Another embodiment of the invention is directed towards a process for preparing amorphous candesartan cilexetil, the process comprising heating candesartan cilexetil Form III, V, IX, XI, or XIV at about 100° C. for about 13 hours.

Another process for preparing amorphous candesartan cilexetil comprises dissolving candesartan cilexetil in dioxane to form a solution; pouring the solution into water to form a mixture; and precipitating from the mixture amorphous candesartan cilexetil.

Preferably, the solution is heated at a temperature of from about 50° C. to about 70° C., more preferably from about 60° C. to about 62° C. Preferably, after the solution is poured into water, the resulting mixture is stirred and cooled. Preferably, the mixture is cooled at a temperature of from about −15° C. to about 15° C., more preferably at about −10° C. to about 0° C.

Candesartan cilexetil forms of the invention can be used in the form of pharmaceutical composition. The invention encompasses a pharmaceutical composition prepared by combining at least one pharmaceutically-acceptable excipient with at least one candesartan cilexetil form of the invention. The invention also encompasses a pharmaceutical composition comprising at least one pharmaceutically-acceptable excipient and at least one candesartan cilexetil form of the invention. In another embodiment, the invention encompasses a method of preparing a pharmaceutical composition comprising combining at least one candesartan cilexetil form of the invention with at least one pharmaceutically-acceptable excipient.

The invention further encompasses a method of treating circulatory system diseases comprising administering a therapeutically effective amount of the pharmaceutical composition of the invention to a mammal in need thereof.

The pharmaceutical composition can include at least one diluent or excipient, such as carriers, fillers, bulking agents, binders, wetting agents, disintegrating agents, surface active agents, lubricants, and the like. Any excipient commonly known and used widely in the art can be used in the pharmaceutical composition. Carriers include, but are not limited to, lactose, white sugar, sodium chloride, glucose, urea, starch, calcium carbonate, kaolin, crystalline cellulose, and silicic acid. Binders include, but are not limited to, water, ethanol, propanol, simple syrup, glucose solutions, starch solutions, gelatin solutions, carboxymethyl cellulose, shelac, methyl cellulose, potassium phosphate, and polyvinylpyrrolidone. Disintegrating agents include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, and lactose. Disintegration inhibitors include, but are not limited to, white sugar, stearin, coconut butter, and hydrogenated oils. Absorption accelerators include, but are not limited to, quaternary ammonium base, and sodium laurylsulfate. Wetting agents include, but are not limited to, glycerin, and starch. Adsorbing agents include, but are not limited to, starch, lactose, kaolin, bentonite, and colloidal silicic acid. Lubricants used include, but are not limited to, purified talc, stearates, boric acid powder, and polyethylene glycol. Tablets can be further coated with commonly known coating materials such as sugar coated tablets, gelatin film coated tablets, tablets coated with enteric coatings, tablets coated with films, double layered tablets, and multi-layered tablets.

One embodiment of the invention is directed towards a method of preparing a pharmaceutical composition comprising combining at least one pharmaceutically-acceptable excipient with any of the forms encompassed by the invention. Various types of dosage forms can be prepared from this method, depending on the therapeutic purpose, for example tablets, pills, powders, liquids, solutions, suspensions, emulsions, granules, capsules, suppositories, injection preparations (solutions and suspensions), and the like.

When tableting the pharmaceutical composition, any commonly known excipient used in the art can be used. For example, carriers include, but are not limited to, lactose, starch, coconut butter, hardened vegetable oils, kaolin, and talc. Binders include, but are not limited to, gum arabic powder, tragacanth gum powder, gelatin, and ethanol. Disintegrating agents include, but are not limited to, agar, and laminalia.

For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added. If necessary, coloring agents, preservatives, perfumes, seasoning agents, sweetening agents, and other medicines may also be added to the desired preparations during the treatment of circulatory system diseases.

Methods of administration of a pharmaceutical composition for treating circulatory system diseases of the present invention are not specifically restricted, and can be administered in various preparations depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations are administered singly intramuscularly, intracutaneously, subcutaneously or intraperitoneally. Suppositories may be administered into the rectum.

The therapeutically-effective amount of candesartan cilexetil contained in a pharmaceutical composition for treating circulatory system diseases according to the present invention should be a dose sufficient to treat, ameliorate, or reduce the symptoms associated with the circulatory system disease. The dosage of a pharmaceutical composition for treating circulatory system diseases according to the present invention will depend on the method of use, the age, sex, and condition of the patient. Typically, about 4 mg to 32 mg of candesartan cilexetil may be contained in an administration form unit.

Having described the invention with reference to certain preferred embodiments, other embodiments will become apparent to one skilled in the art from consideration of the specification. The invention is further defined by reference to the following examples describing in detail the polymorph forms and processes for making them. It will be apparent to those skilled in the art that many modifications, both to materials and methods, may be practiced without departing from the scope of the invention.

EXAMPLES

The candesartan cilexetil forms were identified using Scintag X-ray powder diffractometer model X'TRA, Cu-tube solid state detector. The sample holder was a round standard aluminum sample holder with rough zero background quartz plate with a cavity of 25 (diameter)*0.5 mm (depth). The scanning parameters were range: 2-40 and in some cases 2-30 degrees two-theta; scan mode: continuous scan; step size: 0.05 deg.; and a rate of 3 deg/min.

Typically to determine the Loss on Dry (L.O.D.) by Thermal Gravimetric Analysis (TGA), a sample was heated from about 25° C. to about 200° C. at a heating rate of about 10° C. per minute, while purging with nitrogen gas at a flow rate of 40 ml/min.

Example 1

Preparation of Amorphous Candesartan Cilexetil

Candesartan cilexetil Form II (0.5 g) was placed in a glass container and heated in a static oven at about 100° C. for about 13 hours to obtain amorphous candesartan cilexetil. The process was also performed with Forms V, IX, XI, and XIV to obtain amorphous candesartan cilexetil.

Example 2

Preparation of Amorphous Candesartan Cilexetil

Candesartan cilexetil (5 g) was dissolved in dioxane (15.5 g) and heated to about 60° C. to 62° C. to form a solution. When the solution was poured into water (50 g, about 20° C. to 25° C.), a solid formed as a sticky mass. Subsequently, the solution was stirred and cooled first to about 5° C. to 7° C. for about 30 minutes and then to about −10° C. to 0° C. for about 30 minutes, a precipitate formed within the solution. The precipitate was collected by filtration and dried on the filter for about 2 hours and a wet amorphous form (7 g) was obtained. A portion of the wet amorphous form (4.63 g) was dried at reduced pressure, 20 mbar, at about 50° C. to 52° C. for about 2 hours to obtain amorphous form (3.41 g).

Example 3

Preparation of Candesartan Cilexetil Form I

Candesartan cilexetil (5 g) was dissolved in butanol (64.7 g) under argon and heated to about 62° C. to 64° C. to form a solution. The solution was cooled to 20° C. to 25° C. and stirred for about 12 hours after which a precipitate formed. The precipitate was collected by filtration to obtain (wet) Form I.

Example 4

Preparation of Candesartan Cilexetil Form I

The procedure of Example 3 was repeated using a variety of solvents and temperatures. Generally, the process comprises dissolving candesartan cilexetil Form I (C) (5 g) in a solvent, heating the mixture to a temperature to form a solution, cooling the solution to a temperature of 20° C. to 25° C. and maintaining the temperature until a precipitate formed (time), collecting the precipitate by filtration, and drying the precipitate. Optionally, if necessary the precipitate may be washed. The results are summarized in Table 1.

TABLE 1

Preparation of candesartan cilexetil Form I

| Solvent | Temp. (° C.) | Time (hr) | Drying conditions | % Yield |
| --- | --- | --- | --- | --- |
| Acetonitrile (80 ml) | 50 | 6 | 40° C., 1 hr$^a$ | 84% |
| methanol (21.5 g) | 65 | 4 | 40° C. to 50° C., 1 hr$^a$ | 88% |
| methanol (21.5 g) | reflux | 4 | | $^c$ |
| IPA (70 g) | 60 to 62 | 2 | 40° C. to 50° C., 1 hr$^a$ | 80% |
| butanol (64.6 g) | 62 to 64 | 12 | 40° C. to 50° C., 1 hr$^a$ | 74% |
| ethyl acetate (60 g)$^b$ | 60 to 62 | 16 | 46° C. to 48° C., 20 mbar | 22% |
| ethanol (43 g) | 60 to 62 | 2 | 46° C. to 48° C., 20 mbar | 82.6% |

$^a$Drying was carried out at a reduced pressure of about 30 mbar.
$^b$A portion of the wet form I (1.34 g) was dried under reduced pressure (20 mbar) to the constant weight to obtain Form I (1.13 g).
$^c$The solution was hot filtered, cooled to 25° C. to 27° C., and the collected precipitate was not dried.

Example 5

Preparation of Candesartan Cilexetil Form I

Candesartan cilexetil Form I (C) (5 g) was dissolved in a solvent and heated to form a solution. Water was added dropwise to the heated solution until a precipitate started to form. The solution was cooled to about 20° C. to 25° C. and stirred (time 1). Subsequently, the solution was cooled to about 0° C. with ice water and stirred (time 2). The precipitate was collected by filtration and dried under reduced pressure (30 mbar) to obtain Form I. Optionally, the precipitate may be washed with water (20 ml) before drying. The results are summarized in Table 2.

TABLE 2

Preparation of candesartan cilexetil Form I

| Solvent (ml) | Temp (° C.) | Water (ml) | Time 1 (h) | Time 2 (h) | Drying conditions | % Yield |
| --- | --- | --- | --- | --- | --- | --- |
| Acetone (55) | 50 to 55 | 36 | 0.5 | 1 | 40° C. to 45° C., 1 hr | 80% |
| Methanol (45) | 60 to 65 | 14 | 0.5 | 2 | 40° C. to 45° C., 1 hr | 80% |
| DMF (10) | 20 to 25 | 4 | 0.75 | 1 | 50° C., 1 hr | 90% |
| Acetonitrile (100) | 70 to 75 | 65 | 1 | 1 | 50° C., 4 hrs | 90% |
| IPA (300) | 60 | 370 | 1.5 | 2 | 50° C., 5 hrs | 90% |
| Ethanol (16) | 60 to 64 | 12 | $^a$ | 2 | 50 to 52° C., 4.5 hrs | |

$^a$The solution was cooled to 5° C. to 7° C. instead of 0° C.

Example 6

Preparation of Candesartan Cilexetil Form I

Candesartan cilexetil Form I (C) (5 g) was dissolved in acetone and heated to 62° C. to 64° C. to form a solution. The solution was poured into water (50 g, about 20° C. to 25° C.) to form a precipitate. The solution was stirred for about 30 minutes to obtain a sticky mass, then cooled to 0° C. for about 30 minutes. The precipitate was collected by filtration and dried on the filter for about 0.5 to 1 hours to obtain the wet sample Form I, which was dried at 20 mbar and 50° C. to 52° C. to a constant weight to obtain Form I.

Example 7

Preparation of Candesartan Cilexetil Form I

Candesartan cilexetil Form VII (0.5 g) was placed in a glass container and heated in a static oven at about 100° C. for about 13 hours to obtain candesartan cilexetil Form I. The process was also performed with Form VIII.

Example 8

Preparation of Candesartan Cilexetil Form II

Candesartan cilexetil Form V (3.26 g) was triturated with water (60 g) at about 20° C. to 25° C. for about 24 hours to form a precipitate. The precipitate was collected by filtration and dried on the filter for about 30 minutes to obtain Form II.

Example 9

Preparation of Candesartan Cilexetil Form III

Candesartan cilexetil Form I (C) (5 g) was dissolved in a solvent under argon and heated to 55° C. to 56° C. to form a solution. The solution was filtered, cooled to about 25° C. to 27° C., and stirred for about 2 hours during which time a precipitate formed. The precipitate was collected by filtration, washed, and dried on the filter for about 15 minutes to obtain Form III. When the solvent was acetone (17.4 g), after the first cooling, the solution was stirred at about 0° C. to 5° C. for about 1 hour. The process yielded Form III (5.35 g). When the solvent was THF (7 g), the process yielded Form III (4.7 g).

The process was repeated with THF but water (5 g) was added to the solution and the solution was cooled with stirring first to about 20° C. to 25° C. and then to about 5° C. to 7° C. for about 1 hour, and subsequently at 4° C. to 8° C. for about 44 hours. A precipitate formed and was collected by filtration, and dried on the filter for about 30 minutes to obtain Form II and Form III. The precipitate mixture was dried under reduced pressure (10 mbar) at about 50° C. to 52° C. to obtain Form III.

Example 10

Preparation of Candesartan Cilexetil Form IV

Candesartan cilexetil Form III (1.78 g) was dried at about 48° C. to 50° C. under reduced pressure (20 mbar) to a constant weight (about 30 minutes) to obtain Form IV (1.62 g).

Example 11

Preparation of Candesartan Cilexetil Form V

Candesartan cilexetil Form II (2.09 g) was dried at about 48° C. to 50° C. under reduced pressure (20 mbar) to a constant weight (about 1 hour) to obtain Form V (1.86 g).

Example 12

Preparation of Candesartan Cilexetil Form VI

Candesartan cilexetil Form I (C) (5 g) was dissolved in DCM (6.6 ml) under argon at about 20° C. to 25° C. to form a solution. Heptane (9 ml) was slowly added to the solution, the solution was cooled to about 0° C. to 5° C., and stirred for about 15 minutes until a precipitate formed. The solution was warmed to about 25° C. to 27° C. The precipitate was collected by filtration, washed with heptane (10 ml), and dried on the filter for about 30 minutes to obtain Form VI.

Example 13

Preparation of Candesartan Cilexetil Form VII

Candesartan cilexetil Form VI (2.05 g) was dried at about 48° C. to 50° C. under reduced pressure (20 mbar) to a constant weight (about 1 hour) to obtain Form VII (1.90 g).

Example 14

Preparation of Candesartan Cilexetil Form VII

Candesartan cilexetil Form I (C) (5 g) was triturated with toluene (30 ml) at 50° C. for 1 hour. The suspension was cooled to about 20° C. to 25° C. and a precipitate formed. The precipitate was collected by filtration and dried on the filter for about 30 minutes to obtain Form VII.

The procedure was repeated by dissolving Form I in toluene (50 ml) and heating to about 60° C. to 62° C. for about 24 hours. The precipitate was collected and dried on the filter to obtain wet Form VII (4.26 g). A portion of the wet Form VII (1.73 g) was dried under reduced pressure (30 mbar) at about 50° C. to 52° C. to the constant weight to obtain dry Form VII (1.73 g).

Example 15

Preparation of Candesartan Cilexetil Form VII

Candesartan cilexetil (1 g) was dissolved in DCM (1.9 g) at about 20° C. to 25° C. to form a solution, followed by the addition of butanol (8.1 g). The solution was kept at about −11° C. to −14° C. for six days until a precipitate formed. The precipitate was collected by filtration (about 5 hours) and dried on the filter for about 30 minutes to obtain Form VII.

Example 16

Preparation of Candesartan Cilexetil Form VIII

Candesartan cilexetil Form I (C) (5 g) was dissolved in MEK (21.1 g) under argon and heated to about 60° C. to 62° C. to form a solution. The hot solution was filtered, first allowed to cool to about 25° C. to 27° C., and subsequently allowed to cool to about 4° C. to 6° C. for about 48 hours after which a precipitate formed. The precipitate was collected by filtration and dried on the filter for about 30 minutes to obtain Form VIII (2.88 g).

Example 17

Preparation of Candesartan Cilexetil Form IX

Candesartan cilexetil Form I (C) (5 g) was dissolved in a first solvent to form a solution, and a second solvent was added dropwise at about 25° C. The solution was cooled to 0° C. in an ice bath, and a third solvent was added. The solution was kept cool until a precipitate formed. The precipitate was collected by filtration, and dried under reduced pressure (30 mbar) to obtain Form IX. The results are summarized in Table 3 below.

TABLE 3

| Preparation of candesartan cilexetil Form IX | | | | | |
|---|---|---|---|---|---|
| First solvent (ml) | Second solvent (ml) | Third solvent (ml) | Precipitation conditions | Drying conditions | % Yield |
| DCM (6.6) | acetonitrile (18) | acetonitrile (2) | 0° C., 30 min. | 30 to 40 min. at 40° C. | 70% |
| DCM (6.6) | TBME (30) | TBME (20) | −10 to −15° C., 2 hrs | 2 hrs at 45° C. | 64% |

TABLE 3-continued

Preparation of candesartan cilexetil Form IX

| First solvent (ml) | Second solvent (ml) | Third solvent (ml) | Precipitation conditions | Drying conditions | % Yield |
|---|---|---|---|---|---|
| DCM[a] (6.6) | toluene (15) | toluene (3) | −10° C., 2 hrs | 8 hrs at 50° C. | 95% |
| chloroform[b] (8.5) | toluene (15) | | 25° C. for 30 min., 0° C. for 3 hrs; −10 to −15° C. for 18 hrs | 1 hr 40-45° C. | 92% |

[a]The precipitate was washed with toluene (25 ml) prior to drying.
[b]The precipitate was washed with toluene (10 ml) prior to drying.

Example 18

Preparation of Candesartan Cilexetil Form IX

Candesartan cilexetil Form X (0.5 g) was placed in a glass container and heated in a static oven at about 100° C. for about 13 hours to obtain candesartan cilexetil Form IX.

Example 19

Preparation of Candesartan Cilexetil Form X

Candesartan cilexetil Form I (C) (5 g) was dissolved in dioxane (25 ml), heated to about 50° C., and water (15 ml) was added dropwise to the solution until a precipitate started to form. The solution was stirred and allowed to cool to about 25° C. for about 30 minutes and then, cooled with ice water and stirred for about 1 hour. The precipitate was collected by filtration, washed on the filter with water (10 ml), and dried under reduced pressure (30 mbar) at 40° C. to 45° C. for about 2 hours to obtain Form X.

Example 20

Preparation of Candesartan Cilexetil Form X

Candesartan cilexetil was dissolved in dioxane to form a solution. The solution was kept at about 20° C. to 25° C. for about 1 to 3 weeks to form a precipitate. The precipitate was collected by filtration and dried on the filter to obtain Form X. Candesartan cilexetil Form I (C) (2 g) yielded Form X after 1 week at 25° C. in 65.5%. When left for 3 weeks, candesartan cilexetil (4 g) in dioxane (25.4 g) yielded Form X (2.87 g).

Example 21

Preparation of Candesartan Cilexetil Form XI

Candesartan cilexetil Form I (C) (5 g) was dissolved in a first solvent and a second solvent was added dropwise at 25° C. to the solution. The solution was allowed to cool in an ice bath and a precipitate formed. The precipitate was collected by filtration and dried under reduced pressure (30 mbar) at 50° C. to obtain Form XI. The results are summarized in Table 4 below.

TABLE 4

Preparation of candesartan cilexetil Form XI

| First solvent (ml) | Second solvent (ml) | Cooling conditions | Drying conditions | % Yield |
|---|---|---|---|---|
| chloroform (8) | heptane[a] (15) | 0° C., 1 hr | 40° C. to 45° C., 1 hr | 98% |
| DCM (6.5) | cyclo-hexane (28) | 0° C. for 30 min, then 20° C. to 25° C. for 2 hrs | 50° C., 2.5 hrs | 84% |
| chloroform (8.5) | cyclo-hexane (28) | 20° C. to 25° C. for 30 min, then 0° C. for 1 hr | 40° C., 1 hr | 98% |
| chloroform (7.5) | TBME (40) | 0° C., 2 hrs | 50° C., 1 hr | 73% |

[a]The precipitate was washed on the filter with heptane (30 ml) before drying.

Example 22

Preparation of Candesartan Cilexetil Form XIII

Candesartan cilexetil Form I (C) (2.5 g) was dissolved in DCM (3.5 ml) at about 25° C. to form a solution, and isoamyl acetate (35 ml) was added dropwise. The solution was cooled in an ice bath and stirred for about 3 hours to obtain a precipitate. The precipitate was collected by filtration and dried under reduced pressure (30 mbar) at 50° C. for about 7.5 hours to obtain Form XIII.

Example 23

Preparation of Candesartan Cilexetil Form XIV

Candesartan cilexetil Form I (C) (5 g) was dissolved in DCM (6.6 ml) at 25° C., and toluene (15 ml) was added dropwise. The solution was cooled in an ice bath, and then toluene (3 ml) was slowly added until a precipitate formed.

The solution was cooled to about −10° C. for about 2 hours. The precipitate was collected by filtration, washed on the filter with toluene (5 ml), and dried on the filter for about 30 minutes to obtain Form XIV.

Example 24

Preparation of Form I from Form XIV by Crystallization

Form XIV (43.75 g wet) was dissolved in absolute ethanol (215-363 mL, 6-10 volumes) at 40-60° C. The solution was filtered and returned to the reactor, cooled to −15° C. to 5° C., and kept at this temperature for about 2-24 hours. The precipitated solids were filtered off, washed with cold absolute ethanol (23-35 mL) and dried at 50° C./10 mbar to constant weight to give Form I.

Example 25

Preparation of Form I from Form XIV by Re-slurry

Form XIV (40 g on dry basis, L.O.D.<15%) was re-slurried at 25° C. in absolute ethanol (244 mL, 6 ml/g) for 1-20 hours. The solution was cooled to −10° C. to 10° C., and kept at this temperature for 1-72 hours. The precipitated solids were filtered off, washed with cold absolute ethanol (80 mL) and dried at 50° C./10 mbar to constant weight to give Form I.

Example 26

Preparation of Candesartan Cilexetil Form XV

Candesartan cilexetil Form I (C) (5 g) was dissolved in chloroform (7.5 ml) at 25° C. to form a solution, and acetonitrile (55 ml) was added dropwise. The solution was cooled in an ice bath until a precipitate started to form. The solution was stirred for about 2 hours. The precipitate was collected by filtration, washed on the filter with cold acetonitrile (5 ml), and dried under reduced pressure (30 mbar) at 45° C. for about 1 hour to obtained Form XV (3.7 g).

Example 27

Preparation of Candesartan Cilexetil Form XVI

Candesartan cilexetil Form VI (0.5 g) was placed in a glass container and heated in a static oven at about 100° C. for about 13 hours to obtain candesartan cilexetil Form XVI.

Example 28

Preparation of Candesartan Cilexetil Form XVII

Candesartan cilexetil Form XIII (0.5 g) was placed in a glass container and heated in a static oven at about 100° C. for about 13 hours to obtain candesartan cilexetil Form XVII. The procedure was also performed with Form XV.

Example 29

Preparation of Candesartan Cilexetil Form XVIII

Candesartan cilexetil Form I (C) (5 g) was dissolved in THF (8.9 g) and heated to about 60° C. to 62° C. to form a solution. The solution was poured into cold water (50 g, about 5° C.) to form a precipitate. The solution was cooled to about 5° C. to 7° C. and stirred for about 1 hour. The precipitate was collected by filtration and dried on the filter for about 30 minutes to obtain Form XVIII.

Example 30

Preparation of Candesartan Cilexetil Form XIX

Candesartan cilexetil (5 g) was dissolved in acetonitrile (86.5 g) and heated to about 60° C. to 64° C. to form a solution. The solution was poured into cold water (250 g, about 0° C. to 5° C.) to form a precipitate. The solution was stirred at 0° C. to 5° C. for about 1 hour. The precipitate was collected by filtration and dried on the filter for about 30 minutes to obtain wet Form XIX (5.83 g). A portion of the wet Form XIX (3.16 g) was dried under reduced pressure (20 mbar) at about 50° C. to 52° C. to a constant weight to obtain Form XIX (2.63 g).

Example 31

Preparation of Candesartan Cilexetil Form XX

Candesartan cilexetil (5 g) was dissolved in chloroform (7.5 ml) at about 25° C. to form a solution, and acetonitrile (55 ml) was added dropwise. The solution was cooled in an ice bath until a precipitate started to form, and the solution was stirred for about 2 hours. The precipitate was collected by filtration, washed on the filter with cold acetonitrile (5 ml) to obtain Form XX.

Example 32

Preparation of Candesartan Cilexetil Form XXI

Candesartan cilexetil (2 g) was dissolved in THF (5.2 g) at about 20° C. to 25° C. to form a solution. The solution was filtered and kept for about 3 weeks at about 20° C. to 25° C. to form a precipitate. The precipitate was collected by filtration and dried on the filter for about 30 minutes to obtain Form XXI (2.12 g).

Example 33

Preparation of Candesartan Cilexetil Form XXII

Crude candesartan (31 g) was dissolved at 50° C. in methanol (198 ml), the solution was filtered and returned to a reactor, then the solution was cooled to a temperature of −5° C. to 5° C. and kept at the temperature for about 16 h, the solids were collected by filtration, and washed with cold methanol (18.6 ml) to give Form XXII which was dried at 50° C. at 10 mbar until the weight was constant to give (25.4 g, 81.1%) Form XXII.

As used herein, "crude candesartan" refers to candesartan containing traces of toluene, wherein toluene is present in an amount one of skill in the art would recognize as an impurity.

Example 34

Preparation of Form I from Form XXII by Crystallization

Form XXII (25 g wet) was dissolved at 40-60° C. in absolute ethanol (90-280 mL, 5-10 volumes). The solution was filtered and returned to the reactor, cooled to −15° C. to 5° C., and kept at this temperature for about 2-24 h. The precipitated solids were filtered off, washed with cold absolute ethanol (20-35 mL) to give a white solid which was dried at 50° C./10 mbar to constant weight to give Form I.

Example 35

Preparation of Form I from Form XXII by Re-slurry

Form XXIII (20 g on dry basis, L.O.D.<15%) was re-slurried at 25° C. in absolute ethanol (100 mL, 5 ml/g) for 1-20 hours. The solution was cooled to −10° C. to 10° C. and kept at this temperature for 1-72 hours. The precipitated solids were filtered off, washed with cold absolute ethanol (20 mL) to give Form I.

Example 36

Preparation of Candesartan Cilexetil Form XXIII

A solution of trityl candesartan cilexetil (TCS, 350 g, 410.3 mmol), toluene (1050 ml), methanol (2100 ml), and water (17.5 ml) was refluxed for about 3 h (HPLC control). The solvents were evaporated at 45° C. at 90 mbar to give a residue as a viscous oil, the residue was dissolved at 50° C. in a mixture of toluene/methanol (1041 g, 95:5 w/w) to give 1391 g of a clear solution.

230 g of the solution was cooled to 35° C. to about 45° C. and then seeded with CNS crystalline dry. The mixture was cooled to a temperature of −5° C. to 5° C.; the solution was kept at this temperature for about 1 h; the precipitated solids were collected by filtration, washed with a cold mixture of toluene and methanol (35 ml, 95:5 w/w) to give Form XXIII which was dried at 50° C. at 10 mbar until the weight was constant to give a white solid (33.66 g, 89.1%) Form XXIII.

Example 37

Preparation of Form I from Form XXIII by Crystallization

Form XXIII (33 g wet) was dissolved at 40-60° C. in absolute ethanol (170-280 mL, 6-10 volumes). The solution was filtered and returned to the reactor, cooled to −15° C. to 5° C., and kept at this temperature for about 2-24h. The precipitated solids were filtered off, washed with cold absolute ethanol (23-35 mL), and dried at 50° C./10 mbar to constant weight to give Form I.

Example 38

Preparation of Form I from Form XXIII by Re-slurry

Form XXIII (40 g on dry basis, L.O.D.<15%) was re-slurried at 25° C. in absolute ethanol (241 mL, 6 ml/g) for 1-20 hours. The solution was cooled to −10° C. to 10° C. and kept at this temperature for 1-72 hours. The precipitated solids were filtered off, washed with cold absolute ethanol (40 mL), and dried at 50° C./10 mbar to constant weight to give Form I.

Example 39

Preparation of Candesartan Cilexetil Form XIV-1

A solution of trityl candesartan cilexetil (TCC, 30.0 g, 35.17 mmol), toluene (180 mL), methanol (180 mL), and water (1.6 mL) was refluxed for about 13 h (HPLC control), and the solvents were evaporated at 60° C./30 mbar to give a residue as a viscous oil.

Part of the residue (10.4 g) was dissolved at 50° C. in a mixture of toluene/methanol (20.8 g, 9:1, w/w). the solution was kept at 4-8° C. for about 17 h, the precipitated solids were filtered off, washed on the filter with a cold mixture of toluene/methanol (5.0 g, 9:1, w/w), and dried at 50° C./10 mbar to constant weight to give as a white solid (5.5 g, 78.6%) Form XIV-I.

Example 40

Preparation of Candesartan Cilexetil Form XIV-1

A solution of trityl candesartan cilexetil (TCC, 30.0 g, 35.17 mmol), toluene (180 mL), methanol (180 mL) and formic acid (1.6 g) was refluxed for about 10 h (HPLC control), the solvents were evaporated at 60° C./30 mbar to give a residue as a viscous oil.

The residue was dissolved in a mixture of toluene/methanol (73.0 g, 9: 1 w/w) and kept at 4-8° C. for about 22 h. The precipitated solids were filtered off, washed on the filter with a cold mixture of toluene/methanol (15.0 g, 9:1 w/w) and dried at 50° C./10 mbar to the constant weight to give Form XIV-I as a white solid (16.9 g, 78.6%).

Example 41

Preparation of Candesartan Cilexetil Form XIV-1

A solution of trityl candesartan cilexetil (TCC, 30.0 g, 35.17 mmol), toluene (180 mL), methanol (180 mL), formic acid (1.6 g) and water (0.63 g) was refluxed for about 10 h (HPLC control), the solvents were evaporated at 60° C./30 mbar to give a residue as a viscous oil, (about 31 g, theoretical yield of candesartan cilexetil is 21.47 g).

A part of the residue (10.8 g) was dissolved at 50° C. in a mixture of toluene/methanol (21.6 g, 8 : 2, w/w) and the solution was kept at 4-8° C. for about 17 h. The precipitated solids were filtered off, washed on the filter with a mixture of toluene/methanol (5.0 g, 8:2, w/w) and dried at 50° C./10 mbar to the constant weight to give as a white solid (4.7 g, 63.0%), 97.66% pure by HPLC, Form XIV-I.

A part of the residue (10.1.g) was dissolved at 50° C. in a mixture of toluene/methanol (20.2 g, 7.5:2.5 w/w), the solution was kept at 4-8° C. for about 17 h and after this at −11° C. to −13° C. for about 6 h. The precipitated solids were filtered off, washed on the filter with a mixture of toluene/methanol (5.0 g, 7.5:2.5 w/w) and dried at 50° C./10 mbar to the constant weight to give a white solid (4.8 g, 67.0%) Form XIV-I.

Example 42

Preparation of Form I from Form XIV-1 by Crystallization

Form XIV-1 (35 g wet) was dissolved at 40-60° C. in absolute ethanol (170-280 mL, 6-10 volumes). The solution was cooled to −15° C. to 5° C. and kept at this temperature for about 2-24 h. The precipitated solids were filtered off, washed with cold absolute ethanol (23-35 mL), and dried at 50° C./10 mbar to constant weight to give Form I.

Example 43

Preparation of Form I from Form XIV-1 by Re-slurry

Form XIV-1 (445 g on dry basis, L.O.D.<17%) was re-slurried at 25° C. in absolute ethanol (2670 mL, 6 ml/g) for 1-20 hours. The solution was cooled to −10C to 10° C. and kept at this temperature for 1-72 hours. The precipitated solids were filtered off, washed with cold absolute ethanol (450 mL), and dried at 50° C./10 mbar to the constant weight to give Form I.

What is claimed is:

1. A process for preparing candesartan cilexetil Form I comprising the steps of:
   (a) preparing a slurry of the candesartan cilexetil Form XIV, Form XIV-1, Form XXII, or Form XXIII in a $C_1$-$C_4$ alcohol;
   (b) cooling the slurry to precipitate candesartan cilexetil:
   (c) isolating the precipitated candesartan cilexetil; and
   (d) drying the precipitated candesartan cilexetil to constant weight to obtain candesartan cilexetil Form I, wherein Form XIV has x-ray diffraction peaks at 6.1, 7.3, 8.1, 10.4, 14.2, 15.3, 17.5, 20.5, 22.4, and 25.3 degrees two-theta, ±0.2 degrees two theta, Form XIV-1 has x-ray diffraction peaks at 6.4, 7.3, 8.2, 9.3, 14.3, 16.7, 20.5, 23.8, 25.3, and 28.0 degrees two-theta, ±0.2 degrees two theta, Form XXII has x-ray diffraction peaks at 7.1, 8.9, 10.6, 12.1, 16.3, 17.8, 19.4, 20.5, 21.7, and 24.0 degrees two-theta, ±0.2 degrees two theta and Form XXIII has x-ray diffraction peaks at 6.0, 10.3, 12.0, 16.3, 18.0, 19.8, 21.0, 21.6, 22.4, and 23.1 degrees two-theta, ±0.2 degrees two theta.

2. The process of claim 1, wherein the slurry is cooled at a temperature of from about −20° C. to about 20° C.

3. The process of claim 1, wherein the isolating is by filtering.

4. The process of claim 1, further comprising washing the precipitate from step (c) with an alcohol.

5. The process of claim 4, wherein the alcohol is ethanol.

* * * * *